United States Patent
Mjalli et al.

[11] Patent Number: 5,965,558
[45] Date of Patent: Oct. 12, 1999

[54] MODULATORS OF PROTEINS WITH PHOSPHOTYROSINE RECOGNITION UNITS

[75] Inventors: Adnan Mjalli, Escondido; Sepehr Sarshar, Cardiff by the Sea; Xiaodong Cao, Carlsbad; Farid Bakir, San Diego, all of Calif.

[73] Assignee: Ontogen Corporation, Carlsbad, Calif.

[21] Appl. No.: 08/960,637

[22] Filed: Oct. 29, 1997

Related U.S. Application Data

[60] Division of application No. 08/766,114, Dec. 16, 1996, Pat. No. 5,753,687, which is a continuation-in-part of application No. 08/543,630, Oct. 16, 1995.
[60] Provisional application No. 60/017,610, Jun. 19, 1995.

[51] Int. Cl.[6] .................. A61K 31/495; C07D 241/38
[52] U.S. Cl. .................. 514/249; 514/238.8; 514/241; 514/248; 514/253; 514/255; 514/256; 514/365; 514/369; 514/374; 514/376; 514/396; 514/397; 514/529; 514/546; 514/547; 544/106; 544/215; 544/216; 544/264; 544/265; 544/298; 544/335; 544/336; 544/350; 544/355; 548/204; 548/236; 548/311.1; 548/335.1; 548/343.5; 560/42; 562/567; 562/577; 568/307
[58] Field of Search .......................... 544/355; 514/249

[56] References Cited

U.S. PATENT DOCUMENTS 5,206,392   4/1993   Dean .................................... 549/261

OTHER PUBLICATIONS

Cao, X. et al., Bioorganic & Medicinal Chemistry Letters, vol. 5, No. 24, pp. 2953–2958, (1995).

(List continued on next page.)

*Primary Examiner*—Johann Richter
*Assistant Examiner*—Jane C. Oswecki
*Attorney, Agent, or Firm*—Frank S. Chow

[57] ABSTRACT

Y—X—C(R')=C(R")COOR'''

(A1)

The present invention relates to novel protein tyrosine phosphatase modulating compounds having the general structure shown in Formula (A1), to methods for their preparation, to compositions comprising the compounds, to their use for treatment of human and animal disorders, to their use for purification of proteins or glycoproteins, and to their use in diagnosis. The invention relates to modulation of the activity of molecules with phosphotyrosine recognition units, including protein tyrosine phosphatases (PTPases) and proteins with Src-homology-2 domains, in in vitro systems, microorganisms, eukaryoic cells, whole animals and human beings. R' and R" are independently selected from the group consisting of hydrogen, halo, cyano, nitro, trihalomethyl, alkyl, arylalkyl. R''' is selected from the group consisting of hydrogen, alkyl, substituted alkyl, aryl, arylalkyl. X is aryl. Y is selected from hydrogen or

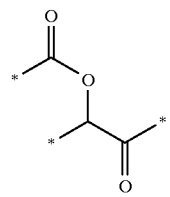

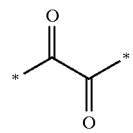

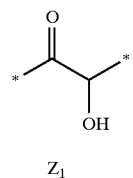

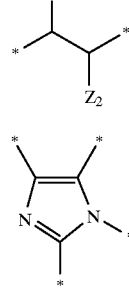

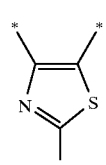

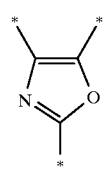

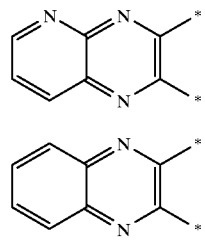

wherein (*) indicates a potential point of attachment to X.

16 Claims, No Drawings

OTHER PUBLICATIONS

Arena, G. et al., J. Chem. Soc. Perkin 2, (1993), (10) pp. 1941–1945.

Crump, R.A.N.C. et al, J. Chem. Soc. Perkin 1, (1992) (24) pp. 3277–3294.

Levitzki et al., "Tyrosine Kinase Inhibition: An Approach to Drug Development," Science, vol. 267, pp. 1782–1788, Mar. 24, 1995.

MODULATORS OF PROTEINS WITH PHOSPHOTYROSINE RECOGNITION UNITS

This is a division of application Ser. No. 08/766,114, filed Dec. 16, 1996 now U.S. Pat. No. 5,753,687; which is a continuation in part of Ser. No. 08/543,630, filed Oct. 16, 1995; which claims the benefit of Provisional Application No. 60/017,610 filed Jun. 19, 1995.

FIELD OF THE INVENTION

The present invention relates to novel protein tyrosine phosphatase modulating compounds, to methods for their preparation, to compositions comprising the compounds, to their use for treatment of human and animal disorders, to their use for purification of proteins or glycoproteins, and to their use in diagnosis. The invention relates to modulation of the activity of molecules with phosphotyrosine recognition units, including protein tyrosine phosphatases (PTPases) and proteins with Src-homology-2 domains, in in vitro systems, microorganisms, eukaryoic cells, whole animals and human beings.

BACKGROUND OF THE INVENTION

Reversible phosphorylation of proteins is a prevalent biological mechanism for modulation of enzymatic activity in living organisms. Tonks et al., *J. Biol. Chem.*, 263(14):6722–30 (1988). Such reversible phosphorylation requires both a protein kinase (PK), to phosphorylate a protein at a particular amino acid residue, and a protein phosphatase (PP), to remove the phosphate moieties. See generally, Hunter, *Cell*, 80:225–236 (1995). Recently, it has been estimated that humans have as many as 2000 conventional PK genes, and as many as 1000 PP genes. Id.

One major class of PK's/PP's—the protein serine/threonine kinases and protein serine/threonine phosphatases—have been shown to play critical roles in the regulation of metabolism. See generally, Cohen, *Trends Biochem. Sci.*, 17:408–413 (1992); Shenolikar, *Ann. Rev. Cell Biol.*, 10:55–86 (1994); Bollen et al., *Crit. Rev. Biochem. Mol. Biol.*, 27:227–81 (1992). As their name suggests, these enzymes phosphorylate and dephoshphorylate serine or threonine residues of substrate proteins. Inhibitors of protein serine/threonine phosphatases and kinases have been described. See, e.g., MacKintosh and MacKintosh, *TIBS*, 19:444–448 (1994).

The protein tyrosine kinases/phosphatases comprise a second, distinct family of PK/PP enzymes of significant interest, and have been implicated in the control of normal and neoplastic cell growth and proliferation. See Fisher et al., *Science*, 253:401–406 (1991). Protein tyrosine kinase (PTK) genes are ancient in evolutionary origin and share a high degree of inter-species conservation. See generally Hunter and Cooper, *Ann. Rev. Biochem.*, 54:897–930 (1985). PTK enzymes exhibit high specificity for tyrosine, and ordinarily do not phosphorylate serine, threonine, or hydroxyproline.

More than 75 members of the PTPase family have been identified in eukaryotes, prokaryotes, and even viruses. Tonks and Neel, *Cell* 87:365–368. Protein tyrosine phosphatases (PTPases) were originally identified and purified from cell and tissue lysates using a variety of artificial substrates, and therefore their natural functions and substrates were not obvious. However, their roles in cellular processes, including cell-cell contact and cell adhesion, and growth factor and antigen signaling events, have begun to be elucidated.

PTPases are generally grouped into two categories: those which have both an extracellular domain and an intracellular catalytic domain, the receptor PTPases (R-PTPases); and those which are entirely intracellular. For R-PTPases much effort has been directed at determining the function of the extracellular domain. Most of the R-PTPases contain extracellular domains which are structurally similar to domains found in known adhesion molecules; these domains include fibronectin type III repeats, immunoglobulin domains, and cadherin extracellular repeats. See generally Brady-Kalnay and Tonks, *Curr. Opin. Cell. Biol.* 7:650–657 (1995); Streuli, *Curr. Opin. Cell. Biol.* 8:182–188 (1996). This homology with proteins known to be involved in adhesion suggested a role for these R-PTPases in regulating or mediating adhesion events. For several of the R-PTPases, this has now been demonstrated.

Cells form specialized structures at the sites of cell-cell contact (adherens junctions) and cell-extracellular matrix contact (focal adhesion). Multiple signal transduction molecules are recruited to these sites, including several PTK's; and these sites are characterized by increased protein tyrosine phosphorylation. These sites are impermanent, and are created and destroyed as required for cell mobility. As enhanced tyrosine phosphorylation is characteristic of the formation of adherens junctions and focal adhesions, it is likely that protein tyrosine dephosphorylation by PTPases serves to regulate the creation and destruction of the sites. Supporting this, several studies have shown that treatment with a general PTPase inhibitor (vanadate) resulted in increased focal adhesion formation and increased cell spreading. Volberg et al., *The EMBO J.* 11:1733–1742 (1992); Bennett et al., *J. Cell Sci.* 106:891–901 (1993). Importantly, the broadly-expressed LAR R-PTPase has been demonstrated to localize to focal adhesions, apparently via the LAR-interacting protein LIP.1. Serra-Pages et al., *The EMBO J.* 14:2827–2838 (1995). As PTPδ and PTPσ, both R-PTPases, also associate with LIP.1 [Pulido et al., *Proc. Natl. Acad. Sci.* 92:11686–11690 (1995)], it is likely that these two phosphatases can also localize to focal adhesions. Most significantly, LAR only localized to the portion of the focal adhesion which is proximal to the nucleus, and is thought to be undergoing disassembly. Thus it is likely that these phosphatases act to negatively regulate focal adhesion formation, acting to enhance the destruction of the focal adhesion site.

R-PTPases may also act to positively regulate adhesion. Adherens junctions contain, among others, adhesion receptors termed cadherins which mediate cell-cell contact through homophilic binding; the cadherins associate with α-, β-, and γ- catenins, intracellular proteins which interact with cortical actin. Association between cadherins and catenins serves to stabilize the adherens junction and to strengthen cell-cell contact. See generally Cowin, *Proc. Natl. Acad. Sci.* 91:10759–10761 (1994). Association of cadherin with β-catenin is decreased by tyrosine phosphorylation of β-catenin [Kinch et al., *J. Cell. Biol.* 130:461–471 (1995); Behrens et al., *J. Cell. Biol.* 120:757–766 (1993)]; moreover, treatment with the PTPase inhibitor vanadate inhibits cadherin-dependent adhesion [Matsuyoshi et al., *J. Cell. Biol.* 118:703–714 (1992)]. Collectively, these data indicate that PTPase activity is critical in maintaining cadherin-mediated cell aggregation. The R-PTPases PTPμ and PTPκ associate intracellularly with cadherins, and colocalize with cadherins and catenins to adherens junctions [Brady-Kalnay et al., *J. Cell. Biol.* 130:977–986 (1995); Fuchs et al., *J. Biol. Chem.* 271:16712–16719 (1996)]; thus PTPμ and PTPκ are likely to enhance cadherin function by limiting catenin phosphorylation.

In addition to their catalytic function in regulating adhesion events, several R-PTPases have direct roles in mediating adhesion through their extracellular domains. PTPκ and PTPμ mediate cellular aggregation through homophilic binding [Brady-Kalnay et al., *J. Cell. Biol.* 122:961–972 (1993); Gebbink et al., *J. Biol. Chem.* 268:16101–16104 (1993); Sap et al., *Mol. Cell. Biol.* 14:1–9 (1994)]. The neuronal PTPζ (which has also been called R-PTPβ) binds to contactin, a neuronal cell recognition molecule; binding of PTPζ to contactin increases cell adhesion and neurite outgrowth. Peles et al., *Cell* 82:251–260 (1995). A secreted splice variant of PTPζ (also known as phosphacan) binds the extracellular matrix protein tenascin [Barnea et al. *J. Biol. Chem.* 269:14349–14352 (1994)], and the neural cell adhesion molecules N-CAM and Ng-CAM [Maurel et al., *Proc. Natl. Acad. Sci.* 91:2512–2516 (1994)]. As the expression of PTPζ is restricted to radial glial cells in the developing central nervous system, which are though to form barriers to neuronal migration during embryogenesis, it is likely that the interaction of PTPζ with contactin, tenascin, N-CAM, and/or Ng-CAM acts to regulate neuronal migration. This has been demonstrated for a related R-PTPase, DLAR, in Drosophila [Krueger et al. *Cell* 84:611–622 (1996)].

Because tyrosine phosphorylation by PTK enzymes usually is associated with cell proliferation, cell transformation and cell differentiation, it was assumed that PTPases were also associated with these events. For several of the intracellular PTPases, this function has now been verified.

SHP1 (which has also been called SHPTP1, SHP, HCP, and PTP-1C [see Adachi et al., *Cell* 85:15 (1996)]), an intracellular PTPase which contains two amino-terminal phosphotyrosyl binding Src Homology 2 (SH2) domains followed by the catalytic PTPase domain, has been demonstrated to be an important negative regulator of growth factor signaling events. See generally Tonks and Neel, supra; Streuli, supra. In mice, loss of SHP1 function (the motheaten and viable motheaten phenotypes) causes multiple hematopoietic defects resulting in immunodeficiency and severe autoimmunity; culminating in lethality by 2–3 weeks or 2–3 months depending on the severity of SHP1 deficiency. Although these mice have reduced numbers of hematopoietic cells, suggesting defects in development and maturation, those cells which survive and enter the periphery are characterized by hyper-responsiveness to growth factors and antigen. This observation suggested a role for SHP1 in negative regulation of hematopoietic signaling events.

This has now been well-established for the erythropoietin receptor (EpoR), a member of the cytokine receptor family (which also includes the receptors for interleukins 2, 3, 4, 5, 6, 7; granulocyte-macrophage colony stimulating factor, and macrophage colony stimulating factor). SHP1 associates via its SH2 domains with tyrosine-phosphorylated EpoR, causing dephosphorylation and inactivation of the EpoR-associated Janus kinase 2 and termination of the cellular response to erythropoietin. Klingmuller et al., *Cell* 80:729–738 (1995). Mutation of the tyrosine on the EpoR to which SHP1 binds results in enhanced cell proliferation to erythropoietin in vitro [Klingmuller, supra]. In humans, mutation of the EpoR resulting in loss of association with SHP1 causes autosomal dominant benign erythrocytosis, which is characterized by increased numbers of erythrocytes in the periphery and increased hematocrit. de la Chapelle et al., *Proc. Natl. Acad. Sci.* 90:4495–4499 (1993).

SHP1 also appears to be a negative regulator of the cellular response to colony stimulating factor-1 (CSF-1, a major macrophage mitogenic cytokine), as cells from viable motheaten and motheaten mice, which have reduced or absent SHP1 function, are hyper-responsive to CSF-1 in vitro. Reduced SHP1 expression also results in increased cellular response to interleukin 3 [Yi et al., *Mol. Cell. Biol.* 13:7577–7586 (1993)]. Collectively, these observations suggest that SHP1 functions to limit the cellular response to cytokines and growth factors by reversing the tyrosine phosphorylation of key signaling intermediates in these pathways.

PTPases appear to play a homologous role in the insulin signaling pathway. Treatment of adipocytes with the PTPase inhibitor vanadate results in increased tyrosine phosphorylation and tyrosine kinase activity of the insulin receptor (InsR), and enhances or mimics the cellular effects of insulin including increased glucose transport. See, e.g., Shisheva and Shechter, *Endocrinology* 133:1562–1568 (1993); Fantus, et al., *Biochemistry* 28:8864–8871 (1989); Kadota, et al., *Biochem. Biophys. Res. Comm.* 147:259–266 (1987); Kadota, et al., *J. Biol. Chem.* 262:8252–8256 (1987). Transiently induced reduction in expression of two PTPases, the intracellular PTPase PTP-1B and the R-PTPase LAR, resulted in similar increases in the cellular response to insulin. Kulas, et al., *J. Biol. Chem.* 270:2435–2438 (1995); Ahmad et al., *J. Biol. Chem.* 270:20503–20508 (1995). Conversely, increased cellular expression of several PTPases (PTPα, PTPε, CD45) in vitro has been demonstrated to result in diminished InsR signaling [see, e.g., Moller, et al., *J. Biol. Chem.* 271:23126–23131 (1995); Kulas et al., *J. Biol. Chem.* 271:755–760 (1996)]. Finally, increased expression of LAR was observed in adipose tissue from obese human subjects [Ahmad, et al., J. Clin. Invest. 95:2806–2812 (1995)]. These data provide clear evidence that PTPases negatively regulate the insulin signaling pathway.

While many of the PTPases function to negatively regulate cellular metabolism and response, it is becoming increasingly evident that PTPases provide important positive signaling mechanisms as well. Perhaps the best example of such a positive regulator is the hematopoietic R-PTPase CD45. See generally Streuli, supra; Okumura and Thomas, supra; Trowbridge, *Annu. Rev. Immunol.* 12:85–116 (1994). CD45 is abundantly expressed on the cell surface of all nucleated hematopoietic cells, in several alternative splice variants. T and B lymphocytes which lack CD45 expression are incapable of responding normally to antigen, suggesting that CD45 is required for antigen receptor signaling. Genetically engineered mice which lack expression of CD45 exhibit severe defects in T lymphocyte development and maturation, indicating an additional role for CD45 in thymopoiesis. The major substrates for CD45 appear to be members of the Src family of PTK's, particularly Lck and Fyn, whose kinase activity is both positively and negatively regulated by tyrosine phosphorylation. Lck and Fyn isolated from CD45-deficient cells are hyperphosphorylated on negative regulatory tyrosine residues, and their PTK activity is reduced. As CD45 can dephosphorylate and activate purified Lck and Fyn in vitro, these data suggest that CD45 maintains the activity of Lck and Fyn in vivo through dephosphorylation of these negative regulatory tyrosines and that this is an important mechanism for maintaining lymphocyte homeostasis.

A second PTPase which is now believed to play an important positive role in signal transduction is the intracellular, SH2-domain-containing SHP2 (which has also been called SHPTP-2, SHPTP-3, syp, PTP2c, and PTP-1D [Adachi, et al., supra]). See generally Saltiel, *Am. J. Physiol.* 270:E375–385 (1996); Draznin, *Endocrinology* 137:2647–2648. SHP2 associates, via its SH2 domains, with the receptor for platelet-derived growth factor (PDGF-R), the receptor for epidermal growth factor (EGF-R), with the insulin receptor, and with the predominant substrate of the InsR, insulin receptor substrate 1 (IRS1). Bennett, et al., *Proc. Natl. Acad. Sci.* 91:7335–7339 (1994); Case, et al., *J. Biol. Chem.* 269:10467–10474 (1994); Kharitonenkov, et al., *J. Biol. Chem.* 270:29189–29193 (1995); Kuhne, et al., *J. Biol. Chem.* 268:11479–11481 (1993). SHP2 PTPase activity is required for cellular response to EGF and insulin, as competitive expression of inactive forms of SHP2 results in diminished signaling events and reduced cellular responses to EGF and insulin. Milarski and Saltiel, *J. Biol. Chem.* 269:21239–21243 (1994); Xiao et al., *J. Biol. Chem.* 269:21244–21248 (1994); Yamauchi et al., *Proc. Natl. Acad. Sci.* 92:664–668 (1995). The relevant substrate(s) for the PTPase domain of SHP2 is not known.

Due to the fundamental role that PTPases play in normal and neoplastic cellular growth and proliferation, a need exists in the art for agents capable of modulating PTPase activity. On a fundamental level, such agents are useful for elucidating the precise role of protein tyrosine phosphatases and kinases in cellular signalling pathways and cellular growth and proliferation. See generally MacKintosh and MacKintosh, *TIBS,* 19:444–448 (1994).

More importantly, modulation of PTPase activity has important clinical significance. For example, PTP-1B overexpression has been correlated with breast and ovarian cancers [Weiner et al., *J. Natl. Cancer Inst.,* 86:372–8 (1994); Weiner et al., *Am J. Obstet. Gynecol.,* 170:1177–883 (1994)], and thus agents which modulate PTP-1B activity would be helpful in elucidating the role of PTP-1B in these conditions and for the development of effective therapeutics against these disease states. The important role of CD45 in hematopoietic development and T lymphocyte function likewise indicates a therapeutic utility for PTPase inhibitors in conditions that are associated with autoimmune disease, and as a prophylaxis for transplant rejection. The antibiotic suramin, which also appears to possess anti-neoplastic indications, has recently been shown to be a potent, irreversible, non-competitive inhibitor of CD45. See Ghosh and Miller, *Biochem. Biophys. Res. Comm.* 194:36–44 (1993). The negative regulatory effects of several PTPases on signaling through receptors for growth factors and cytokines, which are implicated in normal cell processing as well as disease states such as cancer and atherosclerosis, also indicate a therapeutic potential for PTPase inhibitors in diseases of hematopoietic origin.

The PTPase Yop2b is an essential virulence determinant in the pathogenic bacterium Yersinia, responsible for bubonic plague. Bliska et al., *Proc. Natl. Acad Sci. USA,* 88:1187–91 (1991), and thus an antimicrobial indication exists for PTPase inhibitor compounds, as well.

PTPases have been implicated in diabetic conditions. Experiments with one family of PTPase inhibitors, vanadium derivatives, indicate a therapeutic utility for such compounds as oral adjuvants or as alternatives to insulin for the treatment of hyperglycemia. See Posner et al., *J. Biol. Chem.,* 269:4596–4604 (1994). However, such metal-containing PTPase inhibitors act in a fairly non-specific fashion and act with similar potencies against all PTPase enzymes.

In addition to vanadium derivatives, certain organic phosphotyrosine mimetics are reportedly capable of competitively inhibiting PTPase molecules when such mimetics are incorporated into polypeptide artificial PTPase substrates of 6–11 amino acid residues. For example, a "natural" (phosphorylated tyrosine) PTPase substrate, which may be depicted by the Formula:

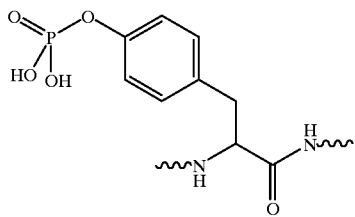

has been mimicked by eleven-mer oligopeptides containing phosphonomethyl phenylalanine (Pmp), as depicted by the schematic Formula:

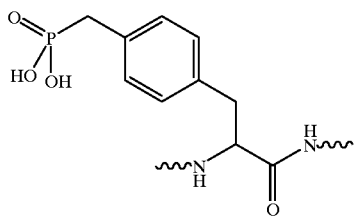

See Chatterjee et al., "Phosphopeptide substrates and phosphonopeptide inhibitors of protein tyrosine phosphatases," in *Peptides: Chemistry and Biology* (Rivier and Smith, Eds.), 1992, Escom Science Publishers: Leiden, Netherlands, pp. 553–55; Burke et al., *Biochemistry,* 33:6490–94 (1994). More recently, Burke et al., *Biochem. Biophys. Res. Comm.* 204(1):129–134 (1994) reported that a particular hexameric peptide sequence comprising a Pmp moiety or, more preferably, a phosphonodifluoromethyl phenylalanine ($F_2$Pmp) moiety, as depicted by the schematic Formula:

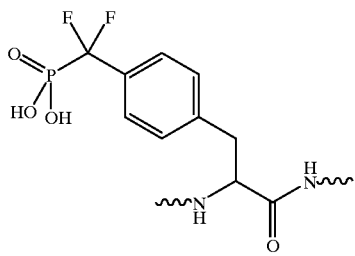

competitively inhibited PTP-1B. However, such hexapeptide inhibitors nonetheless possess drawbacks for PTPase modulation in vivo. More particularly, the hexapeptide inhibitors described by Burke et al. are sufficiently large and anionic to potentially inhibit efficient migration across cell membranes, for interaction with the catalytic domains of transmembrane and intracellular PTPase enzymes which lie within a cell membrane. A need exists for small, organic-molecule based PTPase inhibitors having fewer anionic moieties, to facilitate migration across cell membranes.

For all of the foregoing reasons, a need exists in the art for novel compounds effective for modulating, and especially inhibiting, the phosphatase activity of protein tyrosine phosphatase molecules.

SUMMARY OF THE INVENTION

The invention provides compounds and derivatives thereof useful for modulating, and especially inhibiting, the phosphatase activity of one or more protein tyrosine phosphatase (PTPase) and/or dual specificity phosphatase enzymes. In one aspect, the present invention relates to compounds having the general structure shown in Formula (A1):

wherein R', R", R"', X and Y are defined below. The inventions further provides salts, esters, prodrugs, solvates, and the like of the compounds, and compositions comprising these compounds.

DEFINITIONS

In the specification and claims, the term "derivatives" means: aryl acrylic acids with structure depicted in Formula (A1) having substitution (with, e.g., hydrogen, hydroxy, halo, amino, carboxy, nitro, cyano, methoxy, etc.) at one or more atoms of the aryl ring. Moreover, "derivatives" includes compounds of the Formula (A1) having substitution at the alkene carbons with, e.g., an electron withdrawing group (e.g., Cl, F, Br, $CF_3$, phenyl) or an electron donating group (e.g., $CH_3$, alkoxy).

As used herein, the term "attached" signifies a stable covalent bond, certain preferred points of attachment being apparent to those skilled in the art.

The terms "halogen" or "halo" include fluorine, chlorine, bromine, and iodine.

The term "alkyl" includes $C_1$–$C_{11}$ straight chain saturated and $C_2$–$C_{11}$ unsaturated aliphatic hydrocarbon groups, $C_1$–$C_{11}$ branched saturated and $C_2$–$C_{11}$ unsaturated aliphatic hydrocarbon groups, $C_3$–$C_8$ cyclic saturated and $C_5$–$C_8$ unsaturated aliphatic hydrocarbon groups, and $C_1$–$C_{11}$ straight chain or branched saturated and $C_2$–$C_{11}$ straight chain or branched unsaturated aliphatic hydrocarbon groups substituted with $C_3$–$C_8$ cyclic saturated and unsaturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, octyl, nonyl, decyl, undecyl, ethenyl, propenyl, butenyl, penentyl, hexenyl, heptenyl, octenyl, nonenyl, decenyl, undecenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cycloheptyl, cyclooctyl, cyclopentenyl, cyclohexenyl, cycloheptenyl, cyclooctenyl, methylcyclopropyl, ethylcyclohexenyl, butenylcyclopentyl, and the like.

The term "substituted alkyl" represents an alkyl group as defined above wherein the substitutents are independently selected from halo, cyano, nitro, trihalomethyl, carbamoyl, $C_{0-11}$alkyloxy, aryl$C_{0-11}$alkyloxy, $C_{0-11}$alkylthio, aryl$C_{0-11}$alkylthio, $C_{0-11}$alkylamino, aryl$C_{0-11}$alkylamino, di(aryl$C_{0-11}$alkyl)amino, $C_{1-11}$alkylcarbonyl, aryl$C_{1-11}$alkylcarbonyl, $C_{1-11}$alkylcarboxy, aryl$C_{1-11}$alkylcarboxy, $C_{1-11}$alkylcarbonylamino, aryl $C_{1-11}$alkylcarbonylamino, tetrahydrofuryl, morpholinyl, piperazinyl, hydroxypyronyl, —$C_{0-11}$alkylCOOR$_1$, —$C_{0-11}$alkylCONR$_2$R$_3$ wherein R$_1$I, R$_2$ and R$_3$ are independently selected from hydrogen, $C_1$–$C_{11}$alkyl, aryl$C_0$–$C_{11}$alkyl, or R$_2$ and R$_3$ are taken together with the nitrogen to which they are attached forming a cyclic system containing 3 to 8 carbon atoms with at least one $C_1$–$C_{11}$alkyl, aryl$C_0$–$C_{11}$alkyl substituent.

The term "alkyloxy" (e.g. methoxy, ethoxy, propyloxy, allyloxy, cyclohexyloxy) represents an alkyl group as defined above having the indicated number of carbon atoms attached through an oxygen bridge. The term "alkyloxyalkyl" represents an alkyloxy group attached through an alkyl group as defined above having the indicated number of carbon atoms.

The term "alkylthio" (e.g. methylthio, ethylthio, propylthio, cyclohexenylthio and the like) represents an alkyl group as defined above having the indicated number of carbon atoms attached through a sulfur bridge. The term "alkylthioalkyl" represents an alkylthio group attached through an alkyl group as defined above having the indicated number of carbon atoms.

The term "alkylamino" (e.g. methylamino, diethylamino, butylamino, N-propyl-N-hexylamino, (2-cyclopentyl) propylamino, hexenylamino, pyrrolidinyl, piperidinyl and the like) represents one or two alkyl groups as defined above having the indicated number of carbon atoms attached through an amine bridge. The two alkyl groups maybe taken together with the nitrogen to which they are attached forming a cyclic system containing 3 to 11 carbon atoms with at least one $C_1$–$C_{11}$alkyl, aryl$C_0$–$C_{11}$alkyl substituent. The term "alkylaminoalkyl" represents an alkylamino group attached through an alkyl group as defined above having the indicated number of carbon atoms.

The term "alkylcarbonyl" (e.g. cyclooctylcarbonyl, pentylcarbonyl, 3-hexenylcarbonyl) represents an alkyl group as defined above having the indicated number of carbon atoms attached through a carbonyl group. The term "alkylcarbonylalkyl" represents an alkylcarbonyl group attached through an alkyl group as defined above having the indicated number of carbon atoms.

The term "alkylcarboxy" (e.g. heptylcarboxy, cyclopropylcarboxy, 3-pentenylcarboxy) represents an alkylcarbonyl group as defined above wherein the carbonyl is in turn attached through an oxygen. The term "alkylcarboxyalkyl" represents an alkylcarboxy group attached through an alkyl group as defined above having the indicated number of carbon atoms.

The term "alkylcarbonylamino" (e.g. hexylcarbonylamino, cyclopentylcarbonyl-aminomethyl, methylcarbonylaminophenyl) represents an alkylcarbonyl group as defined above wherein the carbonyl is in turn attached through the nitrogen atom of an amino group. The nitrogen group may itself be substituted with an alkyl or aryl group. The term "alkylcarbonylaminoalkyl" represents an alkylcarbonylamino group attached through an alkyl group as defined above having the indicated number of carbon atoms. The nitrogen group may itself be substituted with an alkyl or aryl group.

The term "aryl" represents an unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4-imidazolyl). The aryl substituents are independently selected from the group consisting of halo, nitro, cyano, trihalomethyl, hydroxypyronyl, $C_{1-11}$alkyl, aryl$C_{1-11}$alkyl, $C_{0-11}$alkyloxy$C_{0-11}$alkyl, aryl$C_{0-11}$alkyloxy$C_{0-11}$alkyl, $C_{0-11}$alkylthio$C_{0-11}$alkyl, aryl$C_{0-11}$alkylthio$C_{0-11}$alkyl, $C_{0-11}$alkylamino$C_{0-11}$alkyl, aryl$C_{0-11}$alkylamino$C_{0-11}$alkyl, di(aryl$C_{1-11}$alkyl)amino$C_{0-11}$alkyl, $C_{1-11}$alkylcarbonyl$C_{0-11}$alkyl, aryl$C_{1-11}$alkylcarbonyl $C_{0-11}$alkyl, $C_{1-11}$alkylcarboxy$C_{0-11}$alkyl, aryl$C_{1-11}$alkylcarboxy$C_{0-11}$alkyl, $C_{1-11}$alkylcarbonylamino$C_{0-11}$alkyl, aryl$C_{1-11}$alkylcarbonylamino$C_{0-11}$alkyl, —$C_0$-

11alkylCOOR$_4$, —C$_{0-11}$alkylCONR$_5$R$_6$ wherein R$_4$, R$_5$ and R$_6$ are independently selected from hydrogen, C$_1$–C$_{11}$alkyl, arylC$_0$–C$_{11}$alkyl, or R$_5$ and R$_6$ are taken together with the nitrogen to which they are attached forming a cyclic system containing 3 to 8 carbon atoms with at least one C$_1$–C$_{11}$alkyl, arylC$_0$–C$_{11}$alkyl substituent.

The definition of aryl includes but is not limited to phenyl, biphenyl, naphthyl, dihydronaphthyl, tetrahydronaphthyl, indenyl, indanyl, azulenyl, anthryl, phenanthryl, fluorenyl, pyrenyl, thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, indolyl, isoindolyl, indolizinyl, indazolyl, imidazolyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, pyrazolyl, triazolyl, tetrazolyl, thiazolyl, isothiazolyl, benzthiazolyl, oxazolyl, isoxazolyl, benzoxazolyl, oxadiazolyl, thiadiazolyl.

The term "arylalkyl" (e.g. (4-hydroxyphenyl)ethyl, (2-aminonaphthyl)hexenyl, pyridylcyclopentyl) represents an aryl group as defined above attached through an alkyl group as defined above having the indicated number of carbon atoms.

The term "arylcarbonyl" (e.g. 2-thiophenylcarbonyl, 3-methoxyanthrylcarbonyl, oxazolylcarbonyl) represents an aryl group as defined above attached through a carbonyl group.

The term "arylalkylcarbonyl" (e.g. (2,3-dimethoxyphenyl)propylcarbonyl, (2-chloronaphthyl)pentenylcarbonyl, imidazolylcyclopentylcarbonyl) represents an arylalkyl group as defined above wherein the alkyl group is in turn attached through a carbonyl.

The term "signal transduction" is a collective term used to define all cellular processes that follow the activation of a given cell or tissue. Examples of signal transduction include but are not in any way limited to cellular events that are induced by polypeptide hormones and growth factors (e.g. insulin, insulin-like growth factors I and II, growth hormone, epidermal growth factor, platelet-derived growth factor), cytokines (e.g. interleukines), extracellular matrix components, and cell-cell interactions.

Phosphotyrosine recognition units/tyrosine phosphate recognition units/phosphotyrosine recognition units are defined as areas or domains of proteins or glycoproteins that have affinity for molecules containing phosphorylated tyrosine residues (pTyr). Examples of pTyr recognition units include but are not in any way limited to: PTPases, SH2 domains and PTB domains.

PTPases are defined as enzymes with the capacity to dephosphorylate pTyr-containing proteins or glycoproteins. Examples of PTPases include but are not in any way limited to: intracellular PTPases (e.g. PTP-1B, TC-PTP, PTP-1C, PTP-1D,PTP-D1, PTP-D2), receptor-type PTPases (e.g. PTPα, PTPε, PTPβ, PTPγ, CD45, PTPκ, PTPμ), dual specificity phosphatases (e.g. VH1, VHR, cdc25) and other PTPases such as LAR, SHP-1, SHP-2, PTP-1H, PTPMEGI, PTP-PEST, PTPζ, PTPS31, IA-2 and HePTP and the like.

Modulation of cellular processes is defined as the capacity of compounds of the invention to 1) either increase or decrease ongoing, normal or abnormal, signal transduction, 2) initiate normal signal transduction, and 3) initiate abnormal signal transduction.

Modulation of pTyr-mediated signal transduction/modulation of the activity of molecules with pTyr recognition units is defined as the capacity of compounds of the invention to 1) increase or decrease the activity of proteins or glycoproteins with pTyr recognition units (e.g. PTPases, SH2 domains or PTB domains) or to 2) decrease or increase the association of a pTyr-containing molecule with a protein or glycoprotein with pTyr recognition units either via a direct action on the pTyr recognition site or via an indirect mechanism. Examples of modulation of pTyr-mediated signal transduction/modulation of the activity of molecules with pTyr recognition units, which are not intended in any way limiting to the scope of the invention claimed, are: a) inhibition of PTPase activity leading to either increased or decreased signal transduction of ongoing cellular processes; b) inhibition of PTPase activity leading to initiation of normal or abnormal cellular activity; c) stimulation of PTPase activity leading to either increased or decreased signal transduction of ongoing cellular processes; d) stimulation of PTPase activity leading to initiation of normal or abnormal cellular activity; e) inhibition of binding of SH2 domains or PTB domains to proteins or glycoproteins with pTyr leading to increase or decrease of ongoing cellular processes; f) inhibition of binding of SH2 domains or PTB domains to proteins or glycoproteins with pTyr leading to initiation of normal or abnormal cellular activity.

A subject is defined as any mammalian species, including humans.

DETAILED DESCRIPTION

This application relates to compounds having the general structure shown in Formula (A1):

wherein (i) R' and R" are independently selected from the group consisting of hydrogen, halo, cyano, nitro, trihalomethyl, alkyl, arylalkyl, (ii) R'" is selected from the group consisting of hydrogen, alkyl, substituted alkyl, aryl, arylalkyl (iii) X is aryl, (iv) Y is selected from hydrogen or

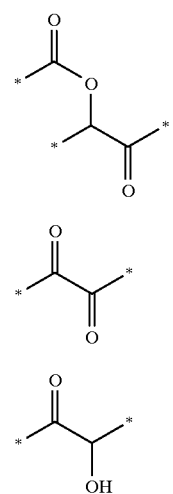

-continued

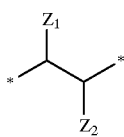

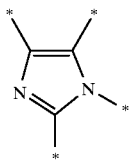

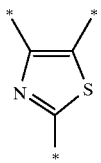

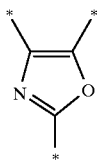

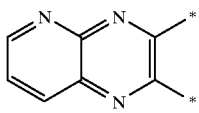

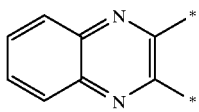

wherein (*) indicates a potential point of attachment to X and all other positions are substituted as described below.

(1) According to the invention, a class of preferred PTPase activity-modulating compounds have the general structural Formula depicted in (A2):

(A2)

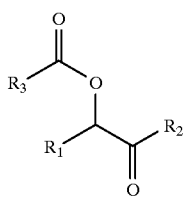

wherein at least one of $R_1$, $R_2$ and $R_3$ substituents has the general structure depicted in Formula (B)

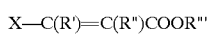 (B)

wherein R', R", R''' and X are defined as above in Formula (A1), and wherein the remaining of $R_1$, $R_2$ and $R_3$ are independently selected from the group consisting of hydrogen, alkyl, substituted alkyl, aryl, arylalkyl.

(2) According to the invention, a class of preferred PTPase activity-modulating compounds have the general structural Formula depicted in (A3):

(A3)

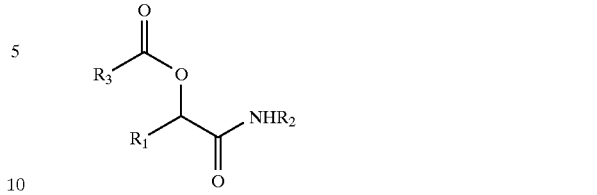

wherein at least one of $R_1$, $R_2$ and $R_3$ substituents has the general structure depicted in Formula (B)

 (B)

wherein R', R", R''' and X are defined as above in Formula (A1), and wherein the remaining of $R_1$, $R_2$ and $R_3$ are independently selected from the group consisting of: hydrogen, alkyl, substituted alkyl, alkylcarbonyl, substituted alkylcarbonyl, aryl, arylalkyl, arylcarbonyl, arylalkylcarbonyl.

(3) According to the invention, a class of preferred PTPase activity-modulating compounds have the general structural Formula depicted in (A4):

(A4)

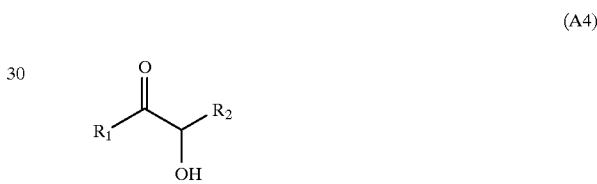

wherein at least one of $R_1$, $R_2$ substituents has the general structure depicted in Formula (B)

 (B)

wherein R', R", R''' and X are defined as above in Formula (A1), and wherein the remaining of $R_1$, $R_2$ is defined as above in Formula (A2).

(4) According to the invention, a class of preferred PTPase activity-modulating compounds have the general structural Formula depicted in (A5):

(A5)

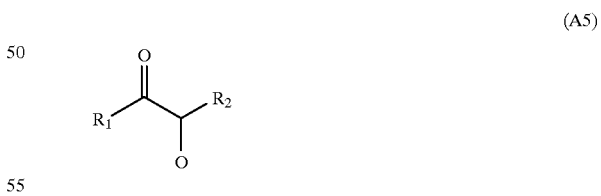

wherein at least one of $R_1$ and $R_2$ substituents has the general structure depicted in Formula (B)

 (B)

wherein R', R", R''' and X are defined as above in Formula (A1), and wherein the remaining of $R_1$ and $R_2$ is defined as above in Formula (A2).

(5) According to the invention, a class of preferred PTPase activity-modulating compounds have the general structural Formula depicted in (A6):

(A6)

[Structure: imidazole with R3, R4 on carbons, R1 on N, R2 on C2]

wherein at least one of $R_1$, $R_2$, $R_3$ and $R_4$ substituents has the general structure depicted in Formula (B)

$$X—C(R')=C(R'')COOR''' \qquad (B)$$

wherein R', R", R''' and X are defined as above in Formula (A1), and wherein the remaining of $R_1$, $R_2$, $R_3$ and $R_4$ have the same definition as $R_1$, $R_2$ and $R_3$ in Formula (A2), with the proviso that when $R_3$ and $R_4$ are selected from substituted phenyl or substituted furyl then the phenyl and furyl substituents exclude hydroxy, halo, trifluoromethyl, $C_{1-6}$alkyl, $C_{1-6}$alkyloxy, $C_{1-6}$alkylthio, amino, $C_{1-6}$alkylamino, di($C_{1-6}$alkyl)amino, phenyl$C_{1-6}$alkylamino and di(phenyl$C_{1-6}$alkyl)amino.

(6) According to the invention, a class of preferred PTPase activity-modulating compounds have the general structural Formula depicted in (A6):

(A6)

[Structure: imidazole]

wherein $R_4$ is selected from $—COR_5$, $—COOR_6$, $—CONR_7R_8$ wherein $R_5$ thru $R_8$ are selected from hydrogen, alkyl, substituted alkyl, aryl, arylalkyl, or $R_7$ and $R_8$ are taken together with the nitrogen to which they are attached forming a cyclic system containing 3 to 8 carbon atoms with at least one alkyl, aryl, arylalkyl substituent, and wherein at least one of $R_1$, $R_2$, and $R_3$ substituents has the general structure depicted in Formula (B)

$$X—C(R')=C(R'')COOR''' \qquad (B)$$

wherein R', R", R''' and X are defined as above in Formula (A1), and wherein the remaining of $R_1$, $R_2$ and $R_3$ are defined as above in Formula (A2).

(7) According to the invention, a class of preferred PTPase activity-modulating compounds have the general structural Formula depicted in (A6):

(A6)

[Structure: imidazole]

wherein $R_1$, $R_2$, $R_3$ and $R_4$ are defined as above in (6).

(8) According to the invention, a class of preferred PTPase activity-modulating compounds have the general structural Formula depicted in (A7):

(A7)

[Structure: oxazole with R3, R2, R1]

wherein $R_2$ is selected from $—COR_5$, $—COOR_6$, $—CONR_7R_8$ wherein $R_5$ thru $R_8$ are defined as above in (6) and wherein at least one of $R_1$ and $R_3$ substituents has the general structure depicted in Formula (B)

$$X—C(R')=C(R'')COOR''' \qquad (B)$$

wherein R', R", R''' and X are defined as above in Formula (A1), and wherein the remaining of $R_1$ and $R_3$ are defined as above in Formula (A2).

(9) According to the invention, a class of preferred PTPase activity-modulating compounds have the general structural Formula depicted in (A8):

(A8)

[Structure: quinoxaline with R1, R2, and $(R_3)_m$]

wherein at least one of $R_1$ and $R_2$ substituents has the general structure depicted in Formula (B)

$$X—C(R')=C(R'')COOR''' \qquad (B)$$

wherein R', R", R''' and X are defined as above in Formula (A1), and wherein the remaining of $R_1$ and $R_2$ is defined as above in Formula (A2), and wherein m is an integer between 0 and 4 and each $R_3$ is independently selected from the group consisting of halo, nitro, cyano, trihalomethyl, hydroxypyronyl, alkyl, arylalkyl, $C_{0-11}$alkyloxy$C_{0-11}$alkyl, aryl$C_{0-11}$alkyloxy$C_{0-11}$alkyl, $C_{0-11}$alkylthio$C_{0-11}$alkyl, aryl$C_{0-11}$alkylthio$C_{0-11}$alkyl, $C_{0-11}$alkylamino$C_{0-11}$alkyl, aryl$C_{0-11}$alkylamino$C_{0-11}$alkyl, di(aryl$C_{1-11}$alkyl)amino$C_{0-11}$alkyl, $C_{1-11}$alkylcarbonyl$C_{0-11}$alkyl, aryl$C_{1-11}$alkylcarbonyl$C_{0-11}$alkyl, $C_{1-11}$alkylcarboxy$C_{0-11}$alkyl, aryl$C_{1-11}$alkylcarboxy$C_{0-11}$alkyl, $C_{1-11}$alkylcarbonylamino$C_{0-11}$alkyl, aryl$C_{1-11}$alkylcarbonylamino$C_{0-11}$alkyl, $—C_{0-11}$alkylCOOR$_4$, $—C_{0-11}$alkylCONR$_5$R$_6$ wherein $R_4$, $R_5$ and $R_6$ are independently selected from hydrogen, $C_1$–$C_{11}$alkyl, aryl$C_0$–$C_{11}$alkyl, or $R_5$ and $R_6$ are taken together with the nitrogen to which they are attached forming a cyclic system containing 3 to 8 carbon atoms with at least one $C_1$–$C_{11}$alkyl, aryl$C_0$–$C_{11}$alkyl substituent.

(10) According to the invention, a class of preferred PTPase activity-modulating compounds have the general structural Formula depicted in (A8):

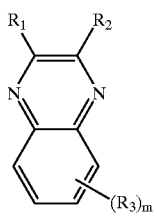
(A8)

wherein $R_1$ is selected from —$COR_5$, —$COOR_6$, —$CONR_7R_8$ wherein $R_7$ thru $R_8$ are defined as above in (6) and wherein $R_2$ has the general structure depicted in Formula (B)

$$X—C(R')=C(R")COOR''' \qquad (B)$$

wherein R', R", R''' and X are defined as above in Formula (A1), and wherein m is an integer between 0 and 4 and each $R_3$ is defined as above in (9).

(11) According to the invention, a class of preferred PTPase activity-modulating compounds have the general structural Formula depicted in (A9):

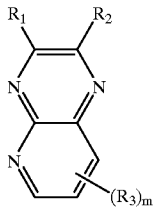
(A9)

wherein m is an integer between 0 and 3 and wherein $R_1$, $R_2$ each $R_3$ is defined as above in (9).

(12) According to the invention, a class of preferred PTPase activity-modulating compounds have the general structural Formula depicted in (A9):

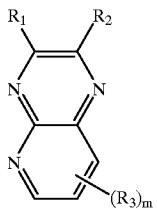
(A9)

wherein either $R_1$ or $R_2$ is selected from —$COR_5$, —$COOR_6$, —$CONR_7R_8$ wherein $R_7$ thru $R_8$ are defined as in (6) and wherein the remainder of $R_1$ and $R_2$ is defined as above in (9), and wherein m is an integer between 0 and 3 and each $R_3$ is defined as above in (9)

(13) According to the invention, a class of preferred PTPase activity-modulating compounds have the general structural Formula depicted in (A10):

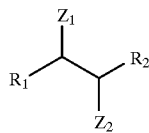
(A10)

wherein $Z_1$ and $Z_2$ are independently selected from the group consisting of $OR_3$, $SR_4$, $NR_5R_6$ and wherein at least one of $R_1$, $R_2$ substituents has the general structure depicted in Formula (B)

$$X—C(R')=C(R")COOR''' \qquad (B)$$

wherein R', R", R''' and X are defined as above in Formula (A1), and wherein the remaining of $R_1$, $R_2$ is defined as above in Formula (A2), and wherein $R_3$, $R_4$, $R_5$, $R_6$ are independently selected from hydrogen, alkyl, substituted alkyl, alkylcarbonyl, substituted alkylcarbonyl, aryl, arylalkyl, arylcarbonyl, arylalkylcarbonyl.

(14) According to the invention, a class of preferred PTPase activity-modulating compounds have the general structural Formula depicted in (A11):

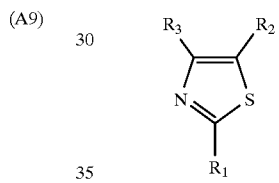
(A11)

wherein at least one of $R_1$, $R_2$, and $R_3$ substituents has the general structure depicted in Formula (B)

$$X—C(R')=C(R")COOR''' \qquad (B)$$

wherein R', R", R''' and X are defined as above in Formula (A1), and wherein the remaining of $R_1$, $R_2$ and $R_3$ are defined as above in Formula (A2).

Preferred compositions of the invention include compositions comprising compounds as defined above in structural formula (A1), (A2), (A3), (A4), (A5), (A6), (A7), (A8), (A9), (A10), (A11) (or pharmaceutically acceptable salts, prodrugs, esters, or solvates of these compounds) in admixture with a pharmaceutically acceptable diluent, adjuvent, or carrier.

Provided according to the invention, therefore, are novel compounds which modulate the activity of PTPase or other molecules with pTyr recognition unit(s) as well as previously known aryl acrylic acid compounds which modulate the activity of PTPase or other molecules with pTyr recognition unit(s).

Another aspect of the present invention provides compositions comprising PTPase modulating compounds of the invention suitable for administration to a mammalian host.

In a preferred embodiment the compounds of the invention act as inhibitors of PTPases, e.g. protein tyrosine phosphatases involved in the regulation of tyrosine kinase signaling pathways. Preferred embodiments include modulation of receptor-tyrosine kinase signaling pathways via interaction with regulatory PTPases, e.g. the signaling pathways of the insulin receptor, the IGF-I receptor and other members of the insulin receptor family, the EGF-receptor family, the platelet-derived growth factor family, the nerve growth factor receptor family, the hepatocyte growth factor receptor family, the growth hormone receptor family and members of other receptor-type tyrosine kinase families. Further preferred embodiments of the invention is modulation of non-receptor tyrosine kinase signaling through modulation of regulatory PTPases, e.g. modulation of members of the Src kinase family. One type of preferred embodiments of the invention relates to modulation of the activity of PTPases that negatively regulate signal transduction pathways. Another type of preferred embodiments of the inventions relate to modulation of the activity of PTPases that positively regulate signale transduction pathways.

In a preferred embodiment compounds of the inventions act as modulators of the active site of PTPases. In another preferred embodiment the compounds of the invention modulate the activity of PTPases via interaction with structures positioned outside the active sites of the enzymes, preferably SH2 domains. Further preferred embodiments include modulation of signal transduction pathways via binding of the compounds of the invention to SH2 domains or PTB domains of non-PTPase signaling molecules.

Other preferred embodiments include use of the compounds of the invention for modulation of cell-cell interactions as well as cell-matrix interactions.

As a preferred embodiment, the compounds of the invention may be used as therapeutics to inhibit PTPases involved in the regulation of the insulin recptor tyrosine kinase signaling pathway in patients with type I diabetes, type II diabetes, impaired glucose tolerance, insuline resistance and obesity. Further preferred embodiments include use of the compounds of the invention for treatment of disorders with general or specific dysfunction of PTPase activity, e.g. proliferative disorders including neoplastic diseases and psoriasis. As another embodiment, the compounds of the invention may be used in pharmaceutical preparations for treatment of osteoporosis.

Preferred embodiments of the invention further include use of compounds of the invention in pharmaceutical preparations to increase the secretion or action of growth hormone and its analogs or somatomedins including IGf-I and IGF-2 by modulating the activity of PTPases or other signal transduction molecules with affinity for phosphotyrosine involved controlling or inducing the action of these hormones or any regulating molecule.

To those skilled in the art, it is well known that the current and potential uses of growth hormone in humans are varied and muti-tudinous. Thus, compounds of the invention can be administered for purposes of stimulating the release of growth hormone from the pituitary or increase its action on target tissues thereby leading to similar effects or uses as growth hormone itself. The uses of growth hormone maybe summarized as follows: stimulation of growth hormone release in the elderly; prevention of catabolic side effects of glucocorticoids; treatment of osteoporosis, stimulation of the immune system; treatment of retardation, accelaration of wound healing; accelerating bone fracture repair; treatment of growth retardation; treating renal failure or insufficiency resulting in growth retardation; treatment of physiological short stature including growth hormone deficient children and short stature associated with chronic illness; treatment of obesity and growth retardation associated with obesity; treating growth retardation associated with the Pader-Willi syndrom and Turner's syndrom; accelerating the recovery and reducing hospitalization of burn patients; treatment of intrauterine growth retardation, skeletal dysplasia, hypercor-tisolism and Cushings syndrome; induction of pulsatile growth hormone release; replacement of growth hormone in stressed patients; treatment of osteochondro-dysplasis, Noonans syndrome, schizophrenia, depressions, Alzheimer's disease, delayed wound healing and psychosocial deprivation; treatment of pulmonary dysfunction and ventilator dependency; attenuation of protein catabolic responses after major surgery; reducing cachexia and protein loss due to chronic illness such as cancer or AIDS; treatment of hyperinsulinemia including nesidio-blastosis; adjuvant treatment for ovulation induction; stimulation of thymic development and prevention of age related decline or thymic function; treatment of immunosuppresed patients; improvement in muscle strength, mobility, maintenance of skin thickness, metabolic homeostasis, renal homeostasis in the frail elderly; stimulation of osteoblasts, bone remodelling and cartilage growth; stimulation of the immune system in companion animals and treatment of disorder of aging in companion animals; growth promotant in livestock and stimulation of wool growth in sheep.

The compounds of the invention may be used in pharmaceutical preparations for treatment of various disorders of the immune system, either as stimulant or suppresor of normal or perturbed immune functions, including autoimmune reactions.

Further embodiments of the invention for treatment of allergic reactions, e.g. asthma, dermal reactions, conjunctivitis.

In another embodiment, compounds of the invention may be used in pharmaceutical preparations for prevention or induction of platelet aggregation.

In yet another embodiment, compounds of the invention may be used in pharmaceutical preparations for treatment of infectious disorders. In particular, the compounds of the invention may be used for treatment of infectious disorders caused by Yersinia and other bacteria as well as disorders caused by viruses or other micro-organisms.

Compounds of the invention may additionally be used for treatment or prevention of diseases in animals, including commercially important animals.

Also included in the present invention is a process for isolation of PTPases via affinity purification procedures based on the use of immobilized compounds of the invention using procedures well-known to those skilled in the art.

The invention is further directed to a method for detecting the presence of PTPases in cell or in a subject comprising (a) contacting said cell or an extract thereof with labeled compounds of the invention.

(b) detecting the binding of the compounds of the invention or measuring the quantity bound, thereby detecting the presence or measuring the quantity of certain PTPases.

The invention further relates to analysis and identification of the specific functions of certain PTPases by modulating their activity by using compounds of the invention in cellular assay systems or in whole animals.

The invention further provides methods for making compounds (A1), (A2), (A3), (A4), (A5), (A6), (A7), (A8), (A9), (A10), (A11) of the present invention having PTPase-modulatory/inhibitory activity. In preferred methods, compounds of the invention are synthesized in a multi-component combinatorial array, which permits rapid synthesis of numerous, structurally related compounds for subsequent evaluation. In preferred synthesis protocols, the acrylic acid moiety of a compound is protected during synthesis by, e.g., esterification with a tert-butyl protecting group. Thus, a preferred method of making compounds of the invention comprises use of a protected acrylic acid reagent and removal of the protective group by, e.g., treatment of a precursor ester compound with acid. Optionally, such a method includes further esterifying or salifying the acrylic acid product thereby obtained.

The compounds of formula (A1), (A2), (A3), (A4), (A5), (A6), (A7), (A8), (A9), (A10), (A11) may be prepared by procedures known to those skilled in the art from known compounds or readily preparable intermediates. General synthetic procedures and examples are as follow:

General Method for the Removal of Tert-butyl Esters

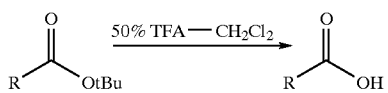

Unless otherwise stated, tert-butyl esters were converted to their corresponding carboxylic acids via treatment with a solution of 50% trifluoroacetic acid in dichloromethane for 1 hour at 23° C. The solvent was removed in vacuo and the residue was azeotroped with toluene or acetonitrile to yield the corresponding carboxylic acid.

General Method for the Synthesis of Compounds (A1) and (A5)

Method 1

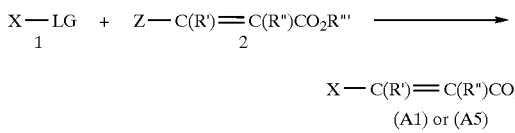

By allowing a compound of formula (1) wherein LG is a suitable leaving group such as bromo, iodo, or triflate to react with compound of formula (2) wherein Z is hydrogen (Heck reaction: *J. Org. Chem.*, 1977, 42, 3903), or trialkyltin (Stille reaction: *J. Am. Chem. Soc.*, 1991, 113, 9585), or B(OH)$_2$ (Suzuki reaction: *J. Am. Chem. Soc.*, 1989, 111, 314) and wherein R', R", R"' and X are defined as above for formula (A1).

These reactions may be carried out neat or in a solvent such as dimethylformamide (DMF), tetrahydrofuran (THF), or toluene, in the presence of a catalyst (e.g. Pd(OAc)$_2$, Pd(PPh$_3$)$_4$, Pd$_2$dba$_3$), a ligand (e.g. Ph$_3$P, Ph$_3$As, (o-tolyl)$_3$P) and a base (e.g. K$_2$CO$_3$, CsCO$_3$, Et$_3$N) at temperatures ranging from 23° C. to 130° C., for 1 to 60 hours.

Examples

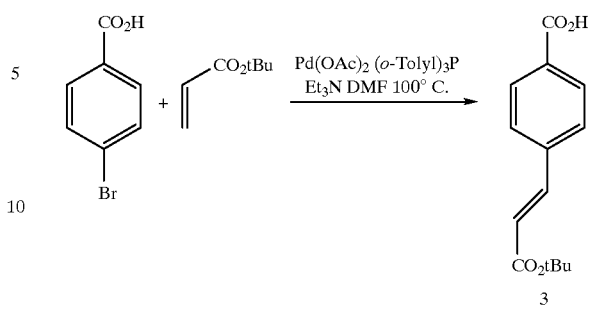

Prepared according to Patel et al (*J. Org. Chem.*, 1977, 42, 3903). $^1$H NMR of 3 (400 MHz, CDCl$_3$) δ 1.5 (s, 9H), 6.4 (d, 1H), 7.6 (m, 3H), 8.05 (d, 2H).

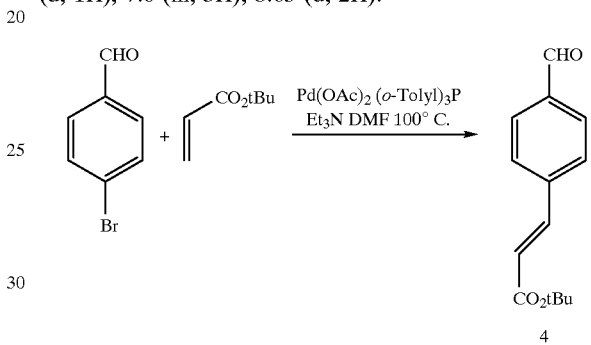

Prepared according to Patel et al (*J. Org. Chem.*, 1977, 42, 3903). $^1$H NMR of 4 (400 MHz, CDCl$_3$) δ 1.5 (s, 9H), 6.4 (d, 1H), 7.55 (d, 1H), 7.6 (d, 2H), 7.8 (d, 2H), 9.95 (s, 1H).

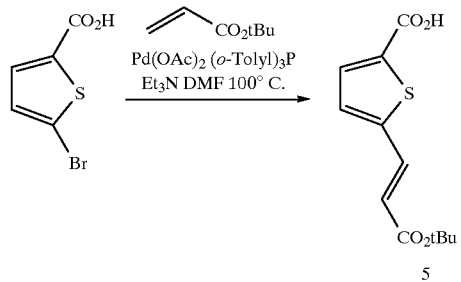

Prepared according to Patel et al (*J. Org. Chem.*, 1977, 42, 3903). $^1$H NMR of 5 (400 MHz, CDCl$_3$) δ 1.44 (s, 9H), 6.26 (d, 1H), 7.18 (d, 1H), 7.56 (d, 1H), 7.74 (d, 1H).

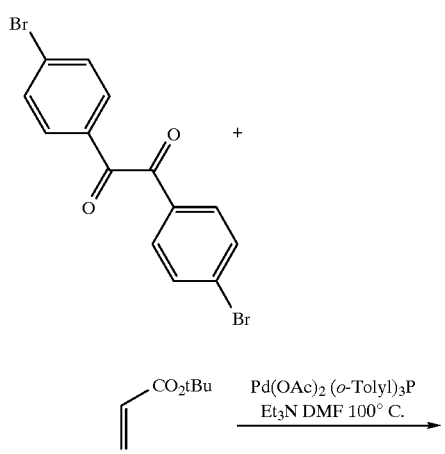
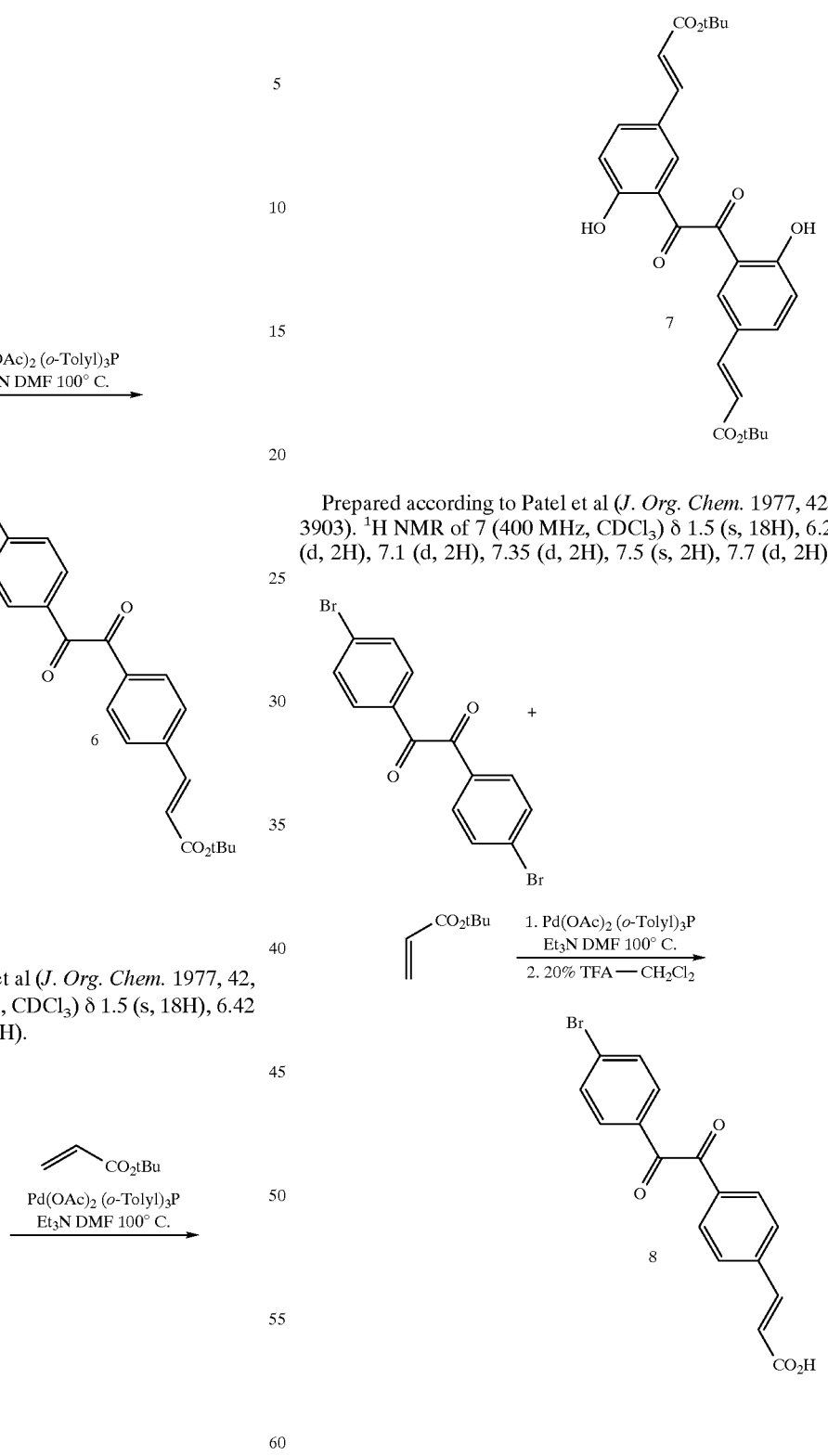
Prepared according to Patel et al (*J. Org. Chem.* 1977, 42, 3903). ¹H NMR of 7 (400 MHz, CDCl$_3$) δ 1.5 (s, 18H), 6.2 (d, 2H), 7.1 (d, 2H), 7.35 (d, 2H), 7.5 (s, 2H), 7.7 (d, 2H).
Prepared according to Patel et al (*J. Org. Chem.* 1977, 42, 3903). ¹H NMR of 6 (400 MHz, CDCl$_3$) δ 1.5 (s, 18H), 6.42 (d, 2H), 7.6 (m, 6H), 7.9 (d, 4H).

To 11 g of 4,4'-dibromobenzil (30 mmol, 1.0 equiv), 67 mg of palladium (II) acetate (0.3 mmol, 0.01 equiv), 365 mg of tri-o-tolylphosphine (1.2 mmol, 0.04 equiv) was added 200 mL of dimethylformamide followed by 4.2 mL (30 mmol, 1.0 equiv) of triethylamine. The mixture was placed in a 100° C. preheated bath and 4.4 mL of tert-butylacrylate (30 mmol, 1.0 equiv) in 30 mL of dimethylforamide was added dropwise over 1 hour. The reaction mixture was heated at 100° C. for 12 hours, cooled to 23° C. and the solvent was removed in vacuo. Ethyl acetate was added and the organic layer was washed with water and dried over sodium sulfate. The solvent was removed and the residue (mixture of dibromobenzil, mono and bis-tert-butylacrylate benzil) was recrystallized from hot 30% dichloromethane in hexane. The solid which crashed out (mixture of dibromobenzil and mono-tert-butylacrylate benzil) was filtered off and treated with 20% trifluoroacetic acid in dichloromethane. After 20 minutes, the mono-tert-butylacrylate benzil 8 was filtered off and washed with 20% trifluoroacetic acid in dichloromethane (1.4 g isolated). The mother liquor (mixture of mono and bis-tert-butylacrylate benzil) was recovered and purified by flash chromatography (ethyl acetate-hexane eluant) to yield 2.4 g of the mono-tert-butylacrylate dione which was treated with 20% trifluoroacetic acid in dichloromethane to give 2.2 g of 8. The combined total yield of 8 was 3.6 g (34%). $^1$H NMR of 8 (400 MHz, $d_6$-DMSO) δ 6.7 (d, 1H), 7.6 (d, 1H), 7.8 (s, 4H), 7.9 (s, 4H).

$^1$H NMR of 9 (400 MHz, $d_6$-DMSO) δ 6.7 (d, 2H), 7.6 (d, 2H), 7.9 (s, 8H).

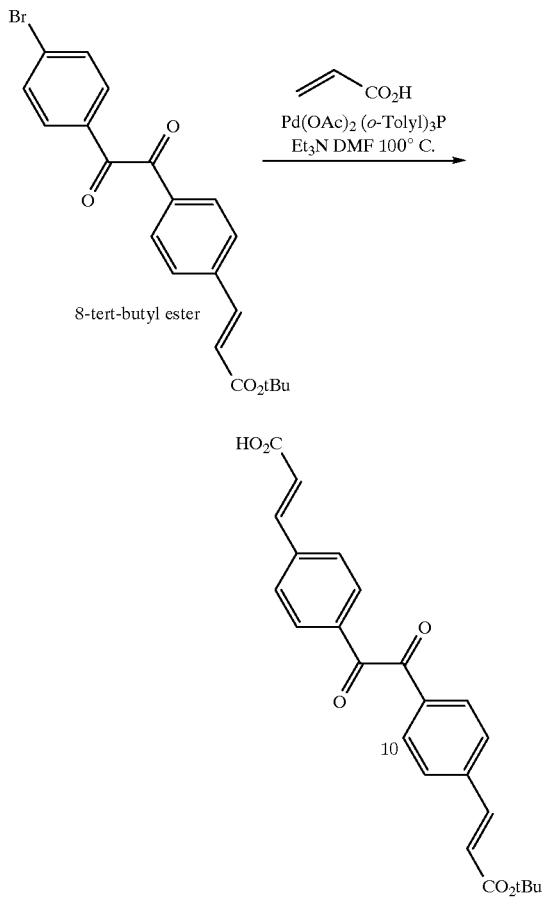

Prepared according to Patel et al (*J. Org. Chem.*, 1977, 42, 3903). $^1$H NMR of 10 (400 MHz, $CDCl_3$-$CD_3OD$ 9:1) δ 1.45 (s, 9H), 6.42 (d, 1H), 6.5 (d, 1H), 7.55 (d, 1H), 7.6 (dd, 4H), 7.68 (d, 1H), 7.92 (dd, 4H).

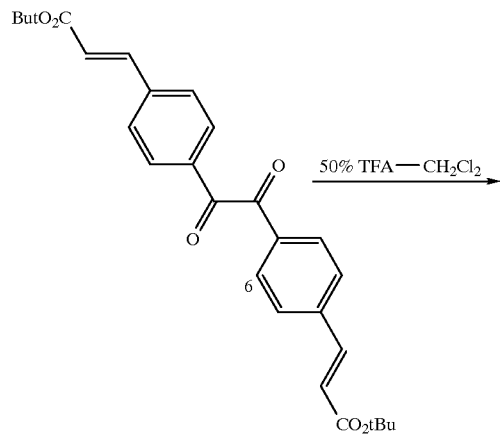

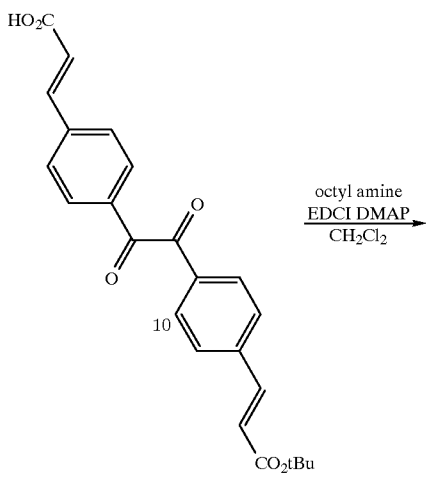

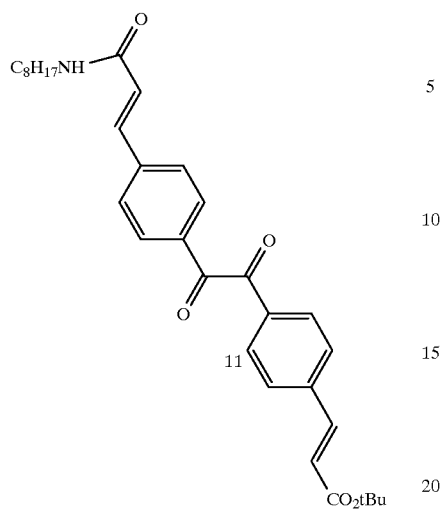

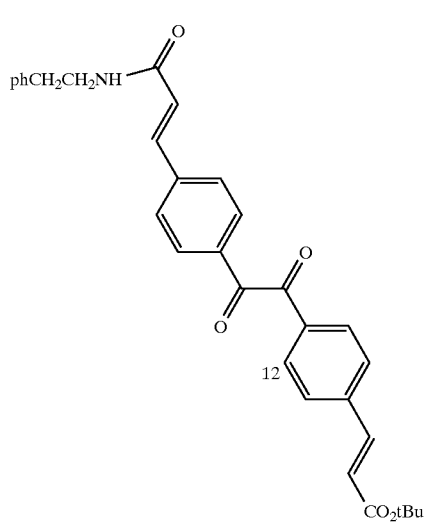

To a solution of 10 (1 equiv) in dichloromethane was added octylamine (1 equiv), EDCI (1.3 equiv) and 4-dimethylaminopyridine (0.5 equiv) at 23° C. The solution was stirred overnight, diluted with ethyl acetate, washed with 1N HCl and saturated sodium bicarbonate and dried over sodium sulfate. The residue was purified by flash chromatography (ethyl acetate-hexane eluant) and the solvent was removed in vacuo to yield compound 11. $^1$H NMR of 11 (400 MHz, CDCl$_3$) δ 0.9 (t, 3H), 1.25 (s br, 10H), 1.5 (s, 9H), 1.55 (s br, 2H), 3.35 (dd, H), 5.6 (t br, 1H), 6.44 9d, 1H), 6.48 (d, 1H), 7.58 (m, 6H), 7.92 (d, 4H).

Same procedure as compound 11. $^1$H NMR of 12 (400 MHz, CDCl$_3$) δ 1.5 (s, 9H), 2.83 (t, 2H), 3.62 (dt, 2H), 5.82 (t br, 1H), 6.4 (m, 2H), 7.18 (m, 5H), 7.6 (m, 6H), 7.9 (m, 4H).

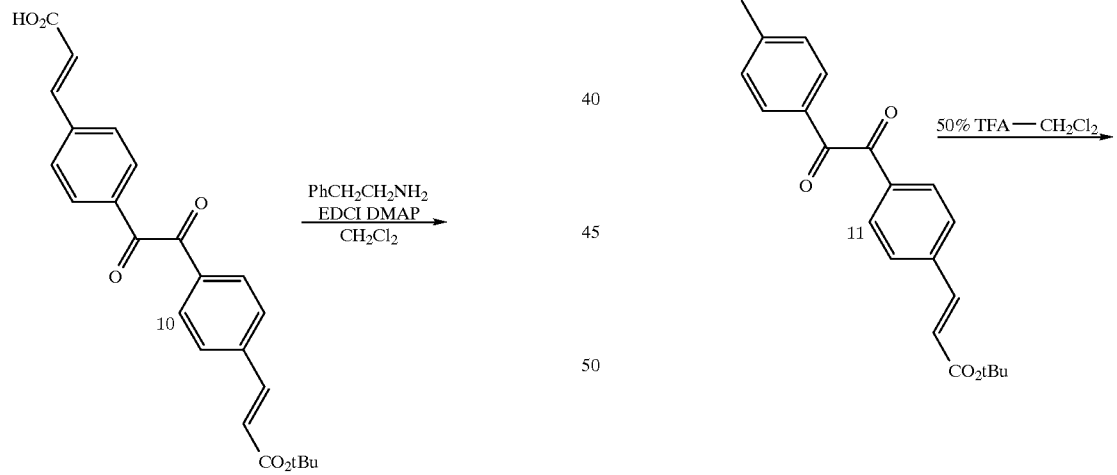

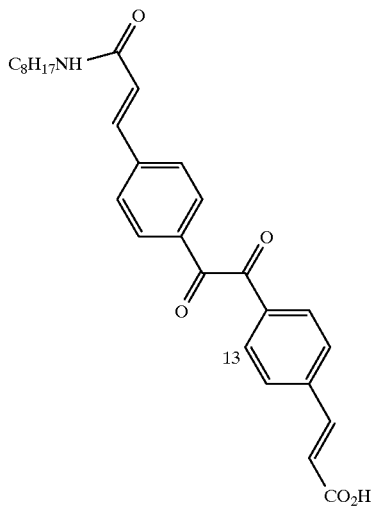

Method 2

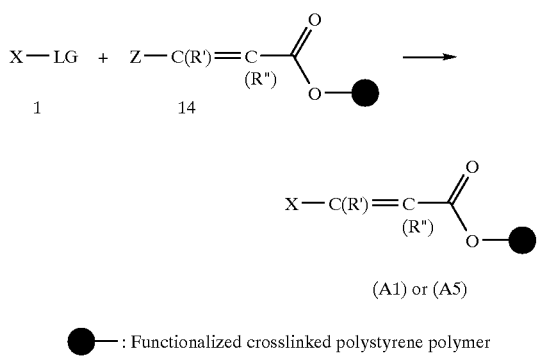

● — : Functionalized crosslinked polystyrene polymer

By allowing a compound of formula (1) as defined above to react with polymer bound compound of formula (14) wherein Z, R' and R" are defined as above in method 1.

These reactions may be carried out on functionalized cross linked polystyrene polymers such as Merrifield resin, Wang resin, Rink resin, "TENTAGEL™" which is a polyethylene-polystyrene polymer resin, in a solvent such as dimethylformamide (DMF), tetrahydrofuran (THF), or toluene, in the presence of a catalyst (e.g. Pd(OAc)$_2$, Pd(PPh$_3$)$_4$, Pd$_2$dba$_3$), a ligand (e.g. Ph$_3$P, Ph$_3$As, (o-tolyl)$_3$P) and a base (e.g. K$_2$CO$_3$, CsCO$_3$, Et$_3$N) at temperatures ranging from 23° C. to 130° C., for 1 to 60 hours.

Examples

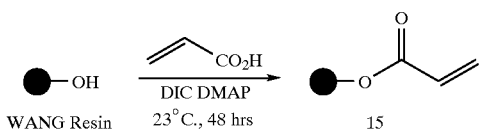

For leading references see: a) Mathias (*Synthesis* 1979, 561). b) Sarantakis et al (*Biochem. Biophys. Res. Commun.* 1976, 73, 336). c) Hudson et al (*Peptide Chemistry* 1985 (Kiso, Y., ed.), 1986, Protein Research Foundation, Osaka.). d) Wang (*J. Am. Chem. Soc.* 1973, 95, 1328). e) Lu et al (*J. Org. Chem.* 1981, 46, 3433.) e) Morphy et al (*Tetrahedron Letters* 1996, 37, 3209). e) Yedidia et al (*Can. J. Chem.* 1980, 58, 1144).

To 10 g (11.2 mmol, 1 equiv) of Wang resin in 80 mL of dry dichloromethane was added 33.6 mmol (3 equiv) of diisopropylcarbodiimide and the mixture was sonnicated under N$_2$ for 2 hours (final bath temperature was 40° C.). Freshly distilled acrylic acid (33.6 mmol, 3 equiv) and 4-dimethylaminopyridine (11.2 mmol, 1 equiv) were added and the mixture was magnetically stirred for 16 hours at ambient temperature. The resin was filtered and thoroughly washed with dichloromethane (500 mL), methanol (500 mL), dimethylformamide (500 mL), dichloromethane (500 mL) and methanol (500 mL) and dried in vacuo (0.1 mmHg) for 24 hours. The coupling was repeated and resin 15 was filtered, washed and dried as above, and used directly in the next step.

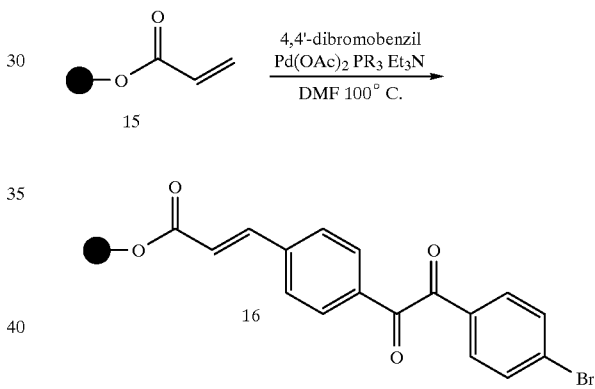

To 8.2 g of acrylate Wang resin 15 was added 10.4 g (28.3 mmol) of 4,4'-dibromobenzil, 437 mg of palladium (II) acetate (1.95 mmol), 1.25 g of tri-o-tolylphosphine (4.11 mmol), 95 mL of dimethylformamide followed by 3.3 mL (23.7 mmol) of triethylamine. The mixture was placed in a 100° C. preheated bath and stirred magnetically at 200 rpm for 2 hours. The resin was filtered hot and washed thoroughly with hot dimethylformamide (500 mL), hot acetic acid (500 mL), methanol (500 mL), dichloromethane (500 mL), dimethylformamide (500 mL), dichloromethane (500 mL) and methanol (500 mL) and dried in vacuo (0.1 mmHg) for 24 hours. The linker was cleaved from the resin with a solution of 20% trifluoroacetic acid in dichloromethane for 20 min at ambient temperature. $^1$H NMR for monobromo-monoacid linker (400 MHz, d$_6$-DMSO) δ 6.7 (d, 2H), 7.6 (d, 2H), 7.8 (s, 4H), 7.9 (s, 4H).

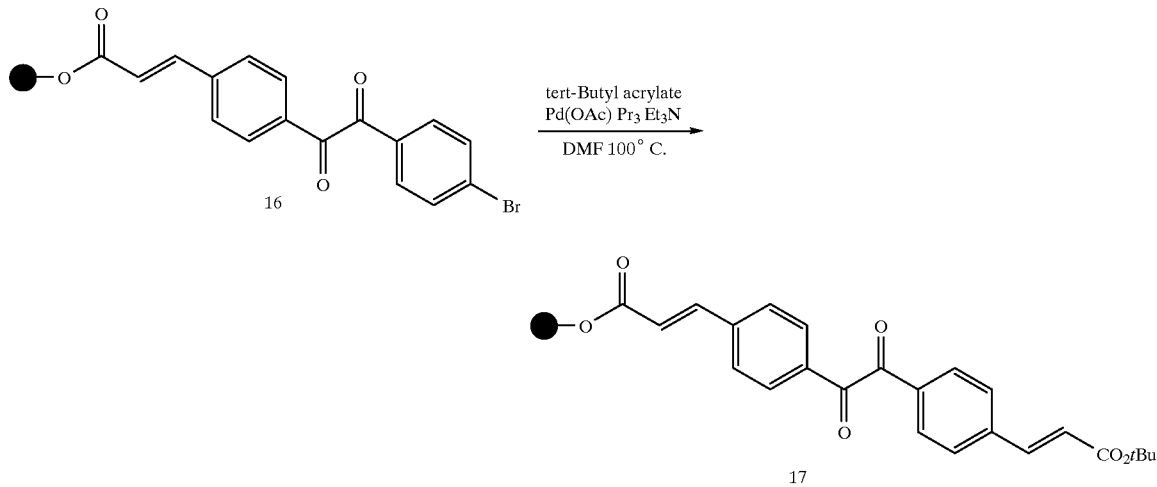

To 10.2 g resin 16 was added 5.41 mL (37 mmol) of tert-butylacrylate, 132 mg of palladium (II) acetate (0.592 mmol), 0.360 g of tri-o-tolylphosphine (1.18 mmol), 31 mL of dimethylformamide followed by 1 mL (7.4 mmol) of triethylamine. The mixture was placed in a 100° C. preheated bath and stirred magnetically at 200 rpm for 18 hours. The resin was filtered hot and washed thoroughly with hot dimethylformamide (500 mL), hot acetic acid (500 mL), methanol (500 mL), dichloromethane (500 mL), dimethylformamide (500 mL), dichloromethane (500 mL) and methanol (500 mL) and dried in vacuo (0.1 mmHg) for 24 hours. The linker was cleaved from the resin with a solution of 20% trifluoroacetic acid in dichloromethane for 20 min at ambient temperature. $^1$H NMR for diacid linker (400 MHz, $d_6$-DMSO) δ 6.7 (d, 2H), 7.6 (d, 2H), 7.9 (s, 8H).

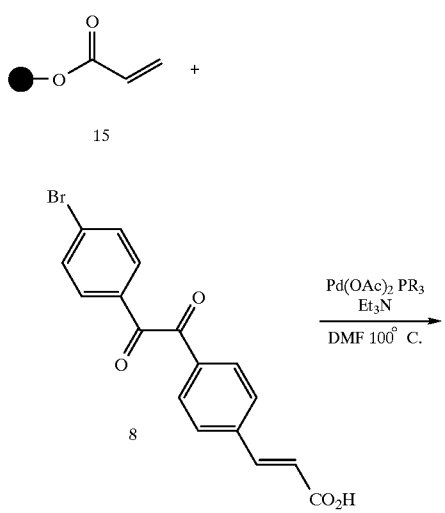

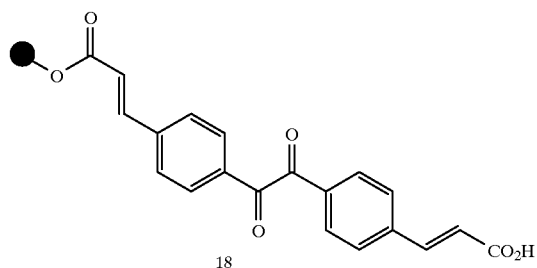

-continued

To 1 g of acrylate resin 15 was added 1.02 g (2.8 mmol) of mono-bromo-mono-tert-butylacrylate benzil (8), 0.044 g of palladium (II) acetate (0.19 mmol), 0.130 g of tri-o-tolylphosphine (0.41 mmol), 10 mL of dimethylformamide followed by a solution of 0.76 mL (5.7 mmol) of triethylamine in 10 mL of dimethylformamide. The mixture was placed in a 100° C. preheated bath and stirred magnetically at 200 rpm for 2 hours. The resin was filtered hot and washed thoroughly with hot dimethylformamide (50 mL), water (50 mL), 10% sodium bicarbonate (50 mL), 10% aqueous acetic acid (50 mL), water (50 mL), methanol (50 mL), dichloromethane (50 mL), methanol (50 mL), dichloromethane (50 mL) and dried in vacuo (0.1 mmHg) for 24 hours. The linker was cleaved from the resin with a solution of 20% trifluoroacetic acid in dichloromethane for 20 min at ambient temperature. $^1$H NMR for diacid linker (400 MHz, $d_6$-DMSO) δ 6.7 (d, 2H), 7.6 (d, 2H), 7.9 (s, 8H).

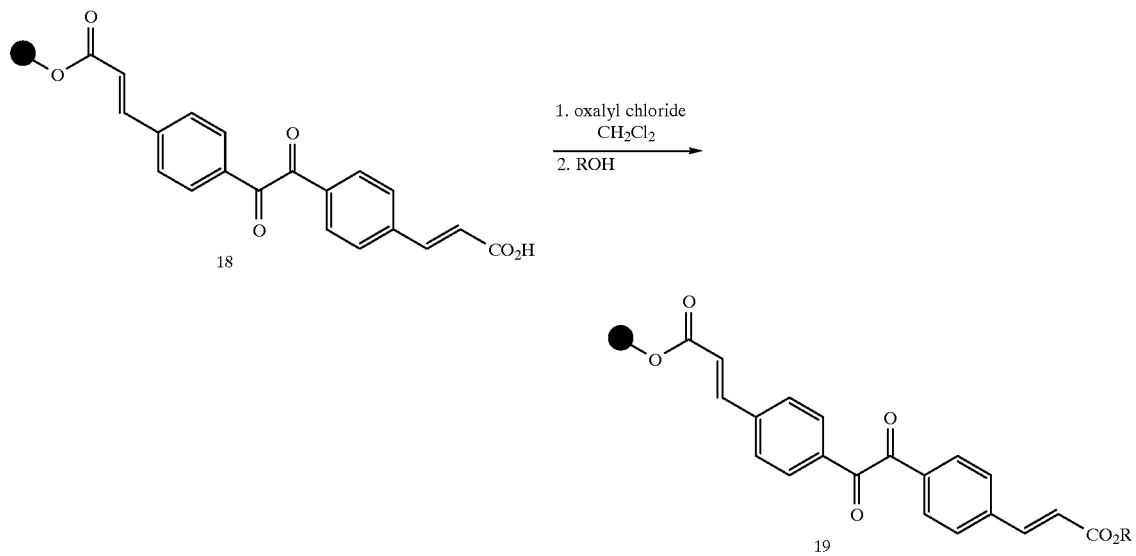

Resin 18 was treated with a 1.0M solution of oxalyl chloride in dichloromethane in the presence of a catalytic amount of dimethylformamide for 1 hour and filtered. The resin was subsequently treated with a dichloromethane solution containing the alcohol (ROH), pyridine and 4-dimethylaminopyridine for 20 hours at 23° C. to yield the monoester resin 19.

Resin 18 was treated with a 1.0M solution of oxalyl chloride in dichloromethane in the presence of a catalytic amount of dimethylformamide for 1 hour and filtered. The resin was subsequently treated with a dichloromethane solution containing the aromatic amine ($ArN(R_1)H$), pyridine and 4-dimethylaminopyridine for 20 hours at 23° C. to yield the monoamide resin 20.

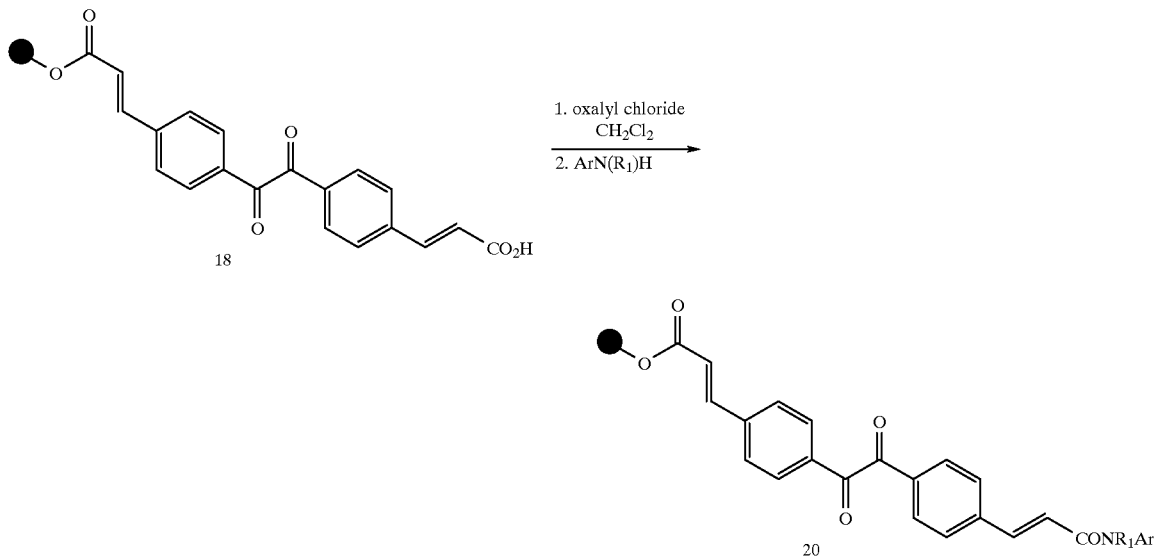

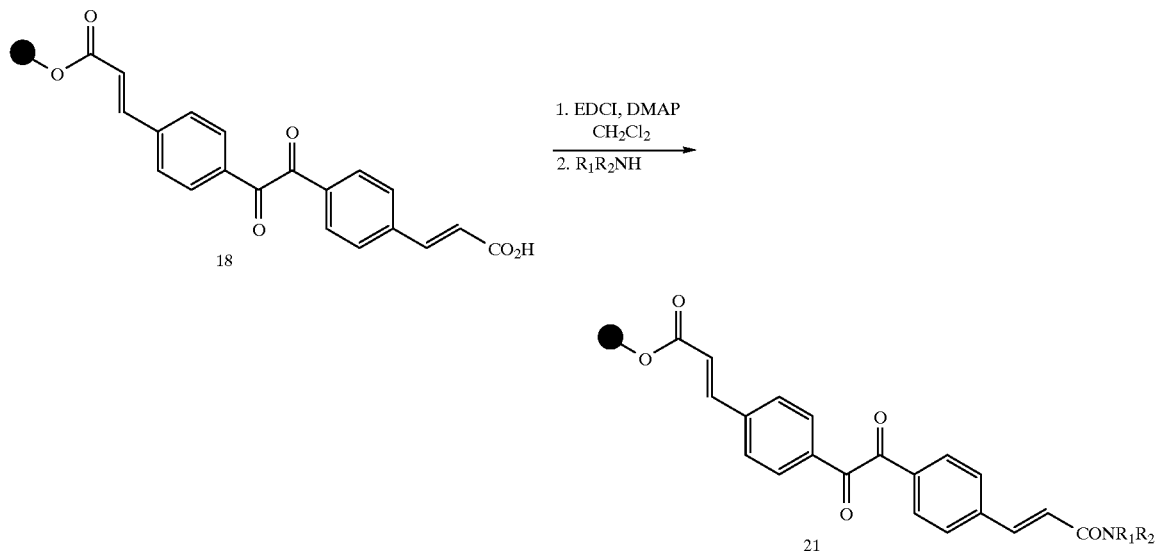

Resin 18 was treated with a dichloromethane solution containing the amine ($R_1R_2NH$), EDCI and 4-dimethylaminopyridine for 20 hours at 23° C. to yield the monoamide resin 21.

General Methods for the Synthesis of Compounds (A2) and (A10)

Method 1

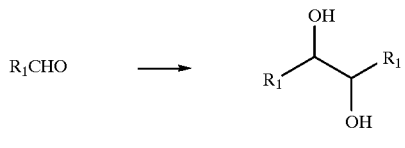

(A10)-1

By allowing an aldehyde ($R_1CHO$) wherein $R_1$ is defined as above in formula (A10) to react with itself.

These reactions may be carried out in a solvent or combination of solvents such as tetrahydrofuran (THF), dichloromethane ($CH_2Cl_2$), in the presence of a catalyst (e.g. $TiCl_3$), and a base (e.g. pyridine) at temperatures ranging from −78° C. to 23° C., for 1 to 60 hours.

Examples

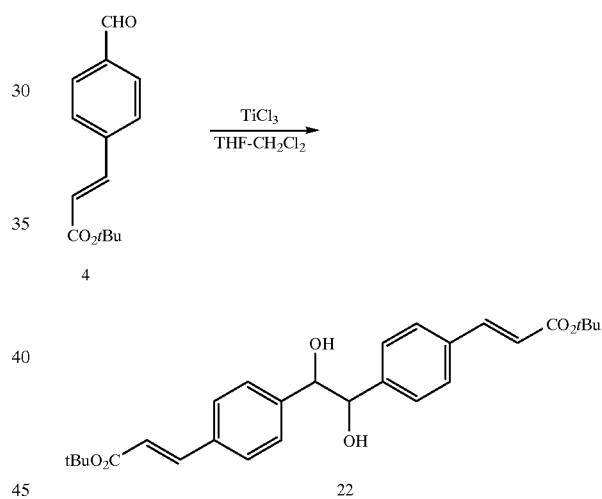

Prepared according to Araneo et al (*Tetrahedron Lett.* 1994, 35, 2213). The reaction was stirred for 4 hrs at 23° C. $^1$H NMR of 22 (400 MHz, $CDCl_3$) δ1.55 (s, 18H), 4.65 (s, 2H), 6.27 (d, 2H), 7.05 (d, 4H), 7.31 (d, 4H), 7.5 (d, 2H).

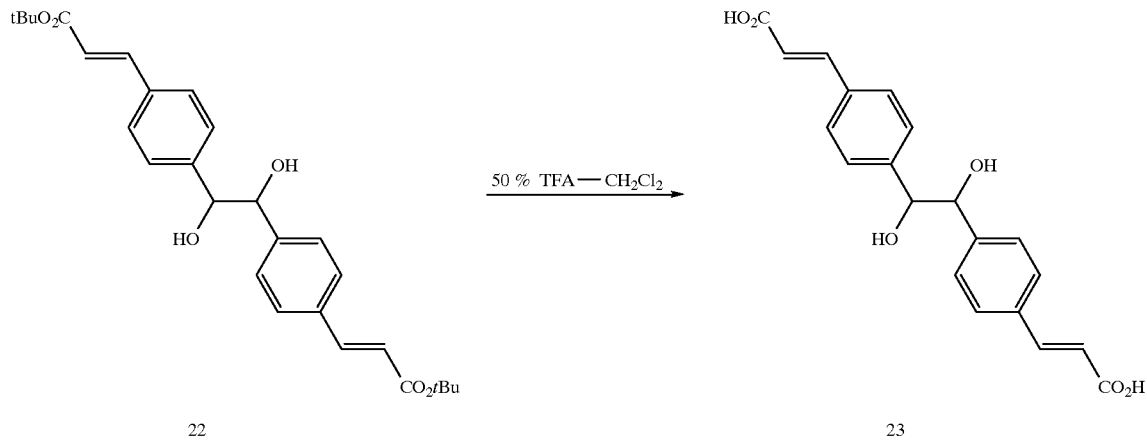

¹H NMR of 23 (400 MHz, CD₃OD) δ 4.65 (s, 2H), 6.4 (d, 2H), 7.15 (d, 4H), 7.4 (d, 4H), 7.6 (d, 2H). MS ESI (neg ion) for [M–H]⁻: 353 (calculated 354).

Method 2

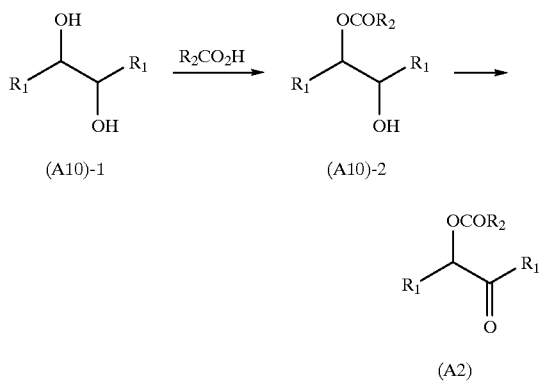

By allowing a compound of formula (A10)-1 prepared as above to react with a acid chloride ($R_2CO_2H$) and by subsequently oxidizing (A10)-2 wherein $R_1$ and $R_2$ are defined as in formula (A2).

The first step in this reaction may be carried out in a solvent such as tetrahydrofuran (THF), dichloromethane ($CH_2Cl_2$), in the presence of diisopropyl carbodiimide (DIC) and a base (e.g. 4-dimethylaminopyridine) at temperatures ranging from 0° C. to 23° C., for 1 to 60 hours. The second step in this reaction may be carried out in a solvent such as dichloromethane ($CH_2Cl_2$), in the presence of an oxidizing reagent (e.g. tetrapropylammonium perruthenate (VII) (TPAP)) and activated 4 Å molecular sieves at temperatures ranging from 0° C. to 23° C., for 1 to 60 hours.

Examples

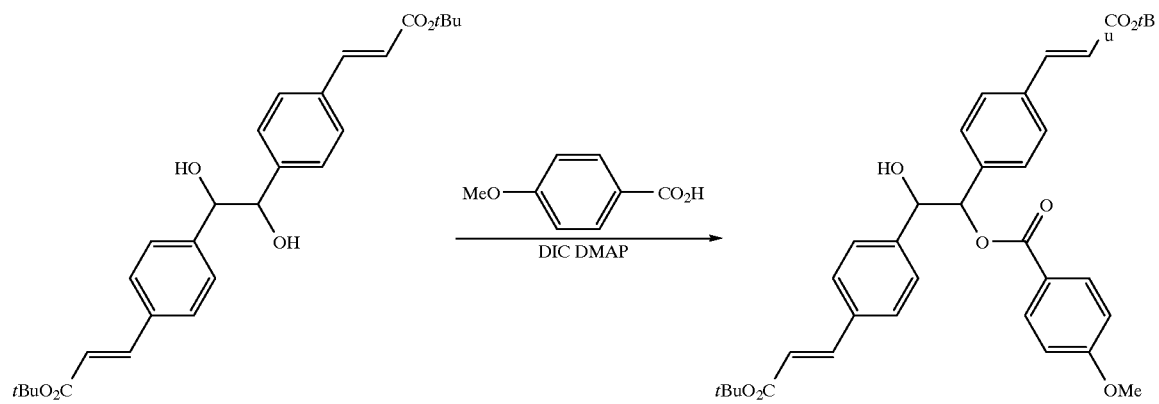

To 50 mg of diol 22 (1 equiv) in 1 mL of dichloromethane was added diisopropyl carbodiimide (0.4 equiv) and the reaction was stirred for 1 hour at 23° C. To the solution was added 4-dimethylaminopyridine (0.1 equiv) followed by paramethoxybenzoic acid (0.4 equiv) in 5 mL of tetrahydrofuran and the mixture was stirred for an additional 3 hours at 23° C. The reaction was diluted with ethyl acetate and washed with 1N HCl, saturated sodium bicarbonate and the organic layer was dried over sodium sulfate. The crude mixture was separated using radial chromatography (ethyl acetate-hexane eluent). $^1$H NMR of 24 (400 MHz, CDCl$_3$) δ 1.55 (s, 18H), 3.8 (s, 3H), 5.05 (d, 1H), 6.0 (d, 1H), 6.25 (d, 1H), 6.3 (d, 1H), 6.9 (d, 2H), 7.1 (d, 4H), 7.32 (m, 4H), 7.45 (d, 1H), 7.48 (d, 1H), 8.0 (d, 1H).

$^1$H NMR of 25 (400 MHz, CD$_3$OD) δ 3.82 (s, 3H), 5.08 (d, 1H), 6.02 (d, 1H), 6.4 (d, 2H), 6.9 (d, 2H), 7.22 (d, 4H), 7.42 (d, 4H), 7.6 (d, 2H), 8.03 (d, 2H). MS ESI (neg ion) for [M−H]$^-$: 487 (calculated 488).

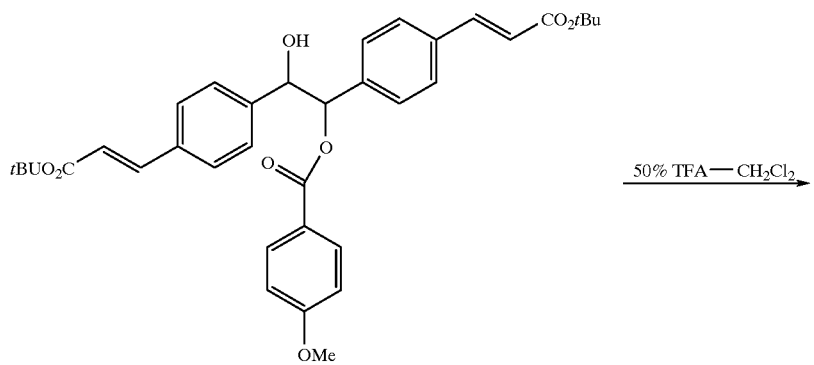

24

50% TFA—CH$_2$Cl$_2$

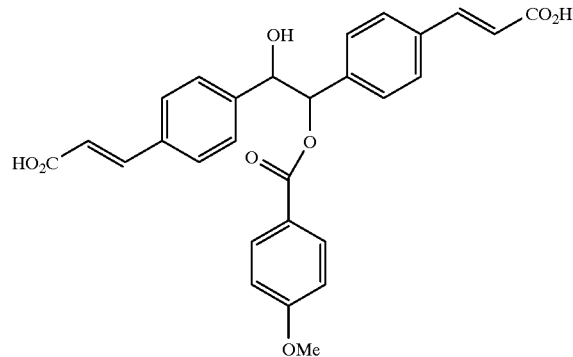

25

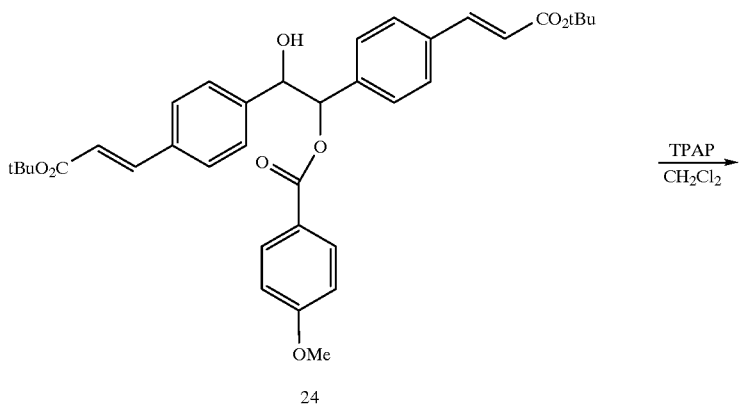
24
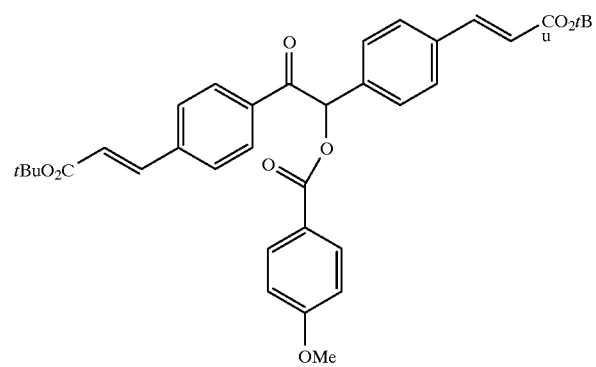
26
Hydroxyester 24 (1 equiv) was oxidized to ketoester 26 at 23° C. in CH$_2$Cl$_2$, in the presence of catalytic amount of TPAP (0.1 equiv), N-methylmorpholine oxide (2 equiv) and 4 Å activated powdered molecular sieves (500 mg/mol of substrate). $^1$H NMR of 26 (400 MHz, CDCl$_3$) δ 1.55 (s, 18H), 3.8 (s, 3H), 6.25 (d, 1H), 6.29 (d, 1H), 6.9 (d, 2H), 7.0 (s, 1H), 7.5 (m, 10H), 7.95 (d, 1H), 8.02 (d, 1H).
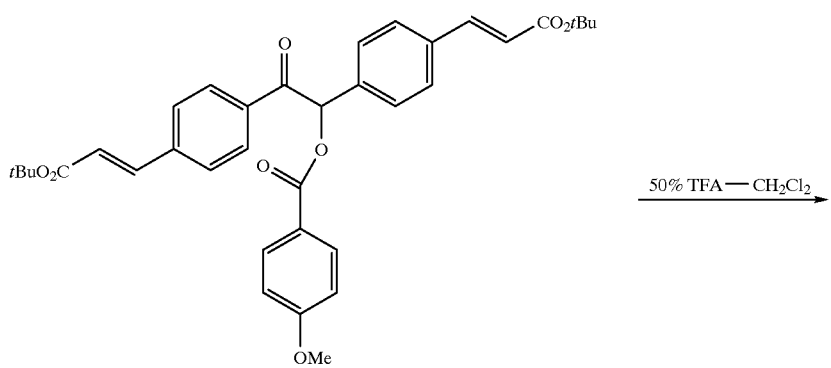
26

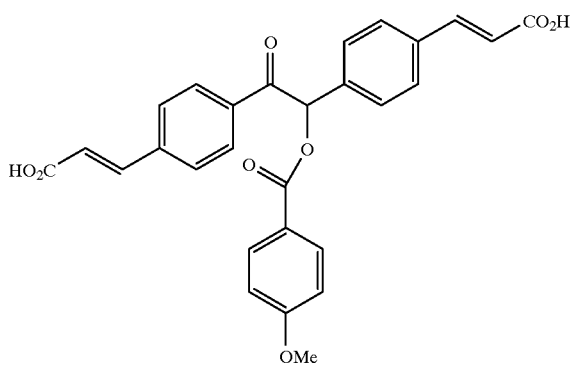

27

$^1$H NMR of 27 (400 MHz, CD$_3$OD) δ 3.82 (s, 3H), 6.45 (d, 1H), 6.55 (d, 1H), 6.95 (d, 2H), 7.18 (s, 1H), 7.65 (m, 10H), 8.0 (d, 1H), 8.08 (d, 1H).

Method 3

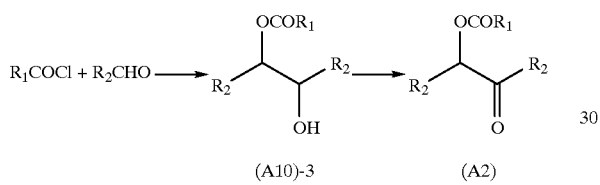

By allowing an acid chloride (R$_1$COCl) to react with an aldehyde (R$_2$CHO) wherein R$_1$, R$_2$ are defined as above in formula (A2) and by subsequently oxidizing (A10)-3.

The first step in this reaction may be carried out in a solvent or a combination of solvents such as tetrahydrofuran (THF), dichloromethane (CH$_2$Cl$_2$), in the presence of a catalyst (e.g. TiCl$_3$), and a base (e.g. pyridine) at temperatures ranging from −78° C. to 23° C., for 1 to 60 hours. The second step in this reaction may be carried out in a solvent such as dichloromethane (CH$_2$Cl$_2$), in the presence of an oxidizing reagent (e.g. tetrapropylammonium perruthenate (VII) (TPAP)) and activated 4 Å molecular sieves at temperatures ranging from 0° C. to 23° C., for 1 to 60 hours.

Examples

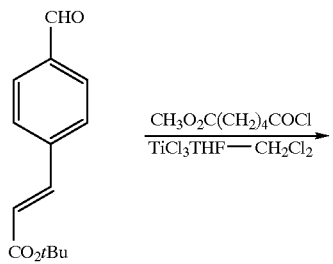

28

Prepared according to Araneo et al (*Tetrahedron Lett.* 1994, 35, 2213). The reaction was stirred for 4 hrs at 23° C., the crude mixture was separated by flash chromatography (ethyl acetate in hexane eluent) to yield hydroxyester 28. $^1$H NMR of 28 (400 MHz, CDCl$_3$) δ 1.55 (s, 18H), 1.6 (m, 4H), 2.2–2.4 (m, 4H), 3.6 (s, 3H), 4.9 (d, 1H), 5.85 (d, 1H), 6.25 (d, 1H), 6.3 (d, 1H), 7.07 (m, 4H), 7.3 (m, 4H), 7.45 (m, 2H).

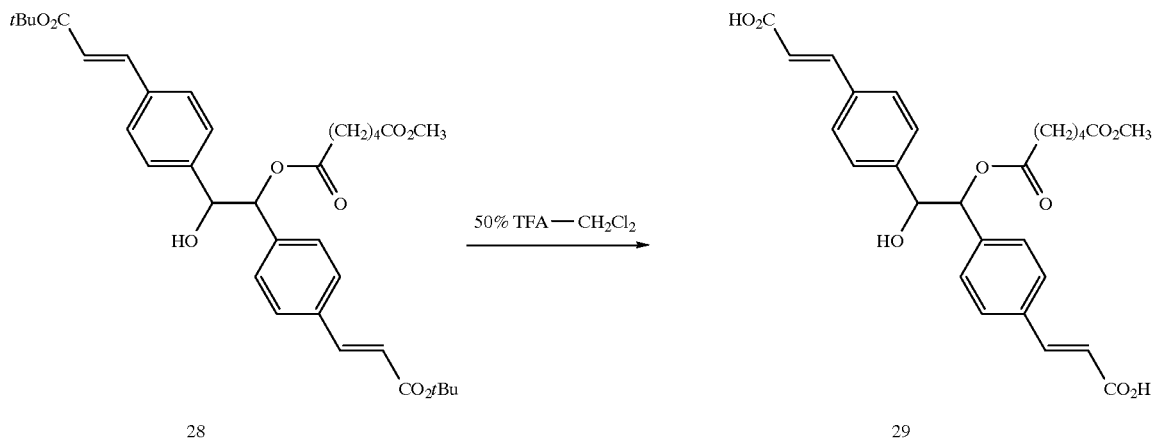

28

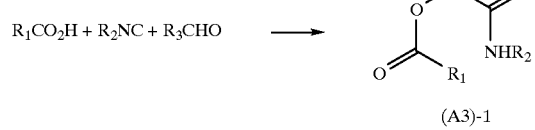

29

¹H NMR of 29 (400 MHz, CD₃OD) δ 1.5 (m, 4H), 2.3 (m, 2H), 2.4 (m, 2H), 3.6 (s, 3H), 4.95 (d, 1H), 5.85 (d, 1H), 6.4 (d, 2H), 7.2 (m, 4H), 7.42 (d, 4H), 7.6 (d, 2H). MS ESI (neg ion) for [M-H]⁻: 495 (calculated 496).

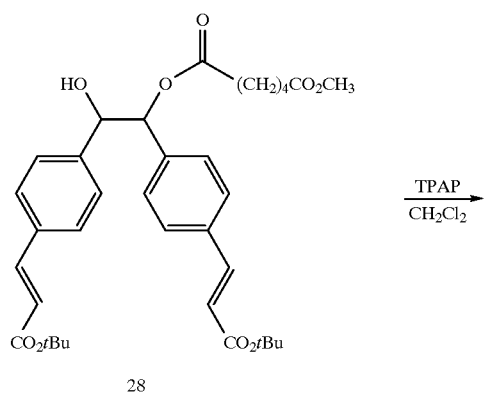

28

TPAP
————→
CH₂Cl₂

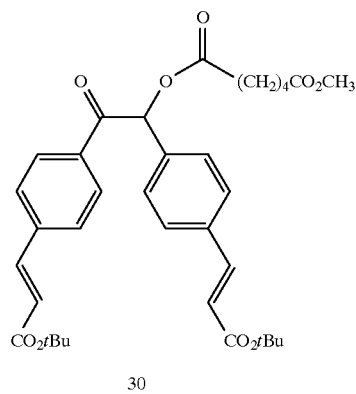

30

Hydroxyester 28 was oxidized to ketoester 30 as above. ¹H NMR of 30 (400 MHz, CDCl₃) δ 1.55 (s, 18H), 1.65 (s br, 4H), 2.3 (m, 2H), 2.5 (m, 2H), 3.6 (s, 3H), 6.3 (d, 1H), 6.35 (d, 1H), 6.78 (s, 1H), 7.4–7.6 (m, 8H), 7.9 (d, 2H).

General Method for the Synthesis of Compounds (A3)

Method 1

R₁CO₂H + R₂NC + R₃CHO ———→

(A3)-1

By allowing a carboxylic acid (R₁CO₂H) to react with an isocyanide (R₂NC) and an aldehyde (R₃CHO) wherein R₁, R₂, and R₃ are defined as above in formula (A3).

These reactions may be carried out in a solvent or a combination of solvents such as dichloromethane (CH₂Cl₂), chloroform (CHCl₃), methanol (MeOH), tetrahydrofuran (THF) or acetonitrile (CH₃CN), in the presence or absence of a catalyst (e.g. ZnCl₂, MgBr₂) at temperatures ranging from −78° C. to 80° C., for 1 to 60 hours.

Examples

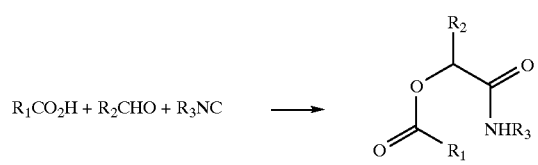

31

Prepared according to Passerini (*Gazz. Chim. Ital.* 1926, 56, 826).

A solution of the carboxylic acid, aldehyde and isocyanide in a given solvent selected from tetrahydrofuran, acetonitrile, ethyl ether or chloroform was stirred between 0° and 25° C. for 1 to 3 days. The solution was diluted with ethyl acetate, washed with saturated sodium bicarbonate and dried over sodium sulfate. The solvent was removed in vacuo and the residue was purified by silica gel chromatography.

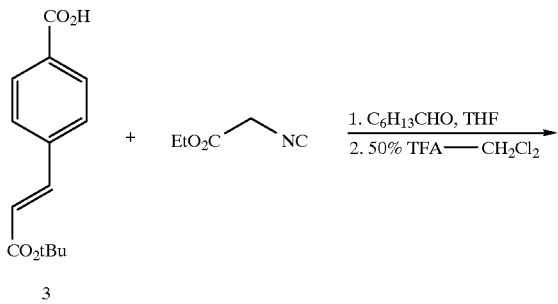

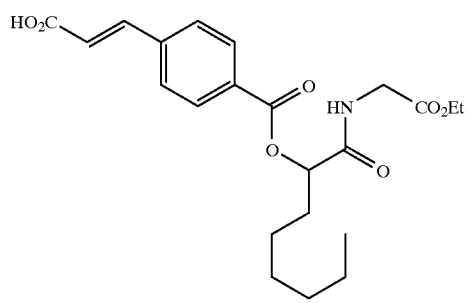

$^1$H NMR of 32 (400 MHz, $d_6$-acetone) δ 0.8 (t, 3H), 1.1–1.6 (m, 9H), 1.97 (m, 1H), 3.9 (m, 2H), 4.1 (m, 2H), 5.3 (t, 1H), 6.62 (d, 1H), 7.7 (d, 1H), 7.8 (d, 2H), 8.05 (d, 2H).

Method 2

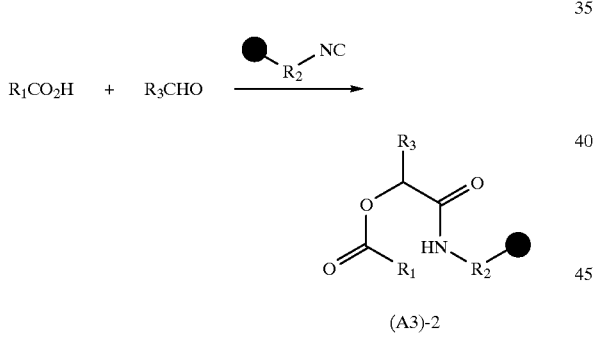

●— : Functionalized crosslinked polystyrene polymer

By allowing a carboxylic acid ($R_1CO_2H$) and an aldehyde ($R_3CHO$) to react with a polymer bound isocyanide ($R_2NC$) wherein $R_1$, $R_2$, and $R_3$ are defined as above in formula (A3).

These reactions may be carried out on functionalized cross linked polystyrene [] polymers such as Merrifield resin, Wang resin, Rink resin, "TENTAGEL™" which is a polyethylene-polystyrene polymer resin, in a solvent or a combination of solvents such as dichloromethane ($CH_2Cl_2$), chloroform ($CHCl_3$), methanol (MeOH), tetrahydrofuran (THF), acetonitrile ($CH_3CN$), in the presence or absence of a catalyst (e.g. $ZnCl_2$, $MgBr_2$) at temperatures ranging from −78° C. to 80° C., for 1 to 60 hours. The product maybe released from the polymer by conditions known to those skilled in the art.

Examples

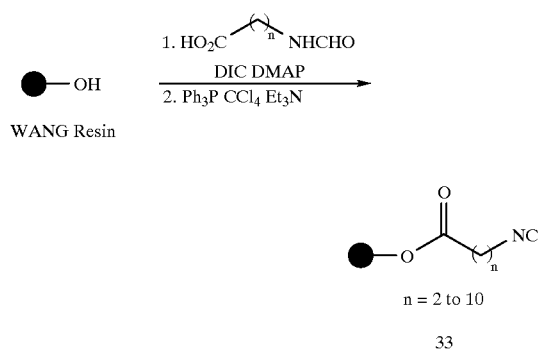

Prepared according to Zhang et al (*Tetrahedron Letters* 1996, 37, 751).

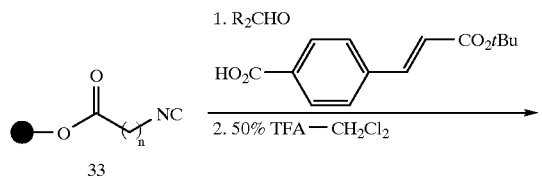

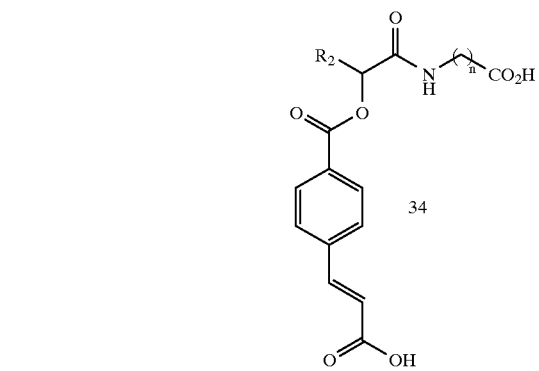

34

A solution of the carboxylic acid 3 in tetrahydrofuran was added to a mixture of the aldehyde and isocyanide resin 33 in tetrahydrofuran or acetonitrile. The mixture was stirred at 25° C. or 60° C. for 1 to 3 days. The resin was filtered and washed with dichloromethane and methanol and dried. Compounds 34 were isolated after treatment of the resin with a solution of 50% trifluoroacetic acid in dichloromethane for 1 hour at 23° C. and removal of the solvent in vacuo.

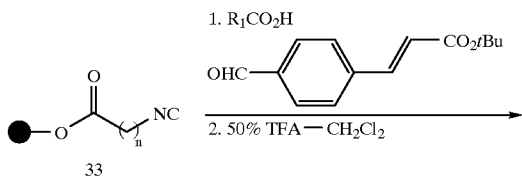

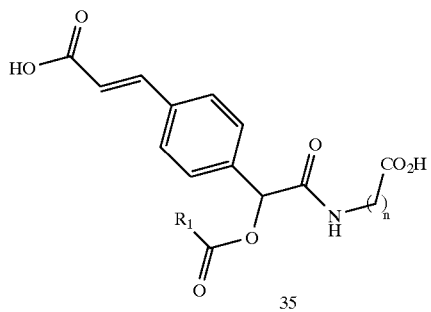

35

A solution of the carboxylic acid in tetrahydrofuran was added to a mixture of the aldehyde 4 and isocyanide resin 33 in tetrahydrofuran or acetonitrile. The mixture was stirred at 25° C. or 60° C. for 1 to 3 days. The resin was filtered and washed with dichloromethane and methanol and dried. Compounds 35 were isolated after treatment of the resin with a solution of 50% trifluoroacetic acid in dichloromethane for 1 hour at 23° C. and removal of the solvent in vacuo.

TABLE 1

34

| Compound | $R_2$ | n | MWt (Calculated) | [M-H]⁻ (Found) |
|---|---|---|---|---|
| 36 | 4-Br-C₆H₄ | 2 | 475; 477 | 474; 476 |
| 37 | 4-Br-C₆H₄ | 5 | 519 | 518 |
| 38 | $C_6H_{14}CHO$ | 2 | 405 | 404 |
| 39 | $C_6H_{14}CHO$ | 5 | 447 | 446 |
| 40 | $C_9H_{20}CHO$ | 2 | 447 | 446 |
| 41 | $C_9H_{20}CHO$ | 5 | 489 | 488 |

TABLE 2

35

| Compound | $R_1$ | n | MWt (Calculated) | [M-H]⁻ (Found) |
|---|---|---|---|---|
| 42 | 4-MeO-C₆H₄ | 2 | 427 | 426 |
| 43 | 4-MeO-C₆H₄ | 5 | 469 | 468 |

TABLE 2-continued

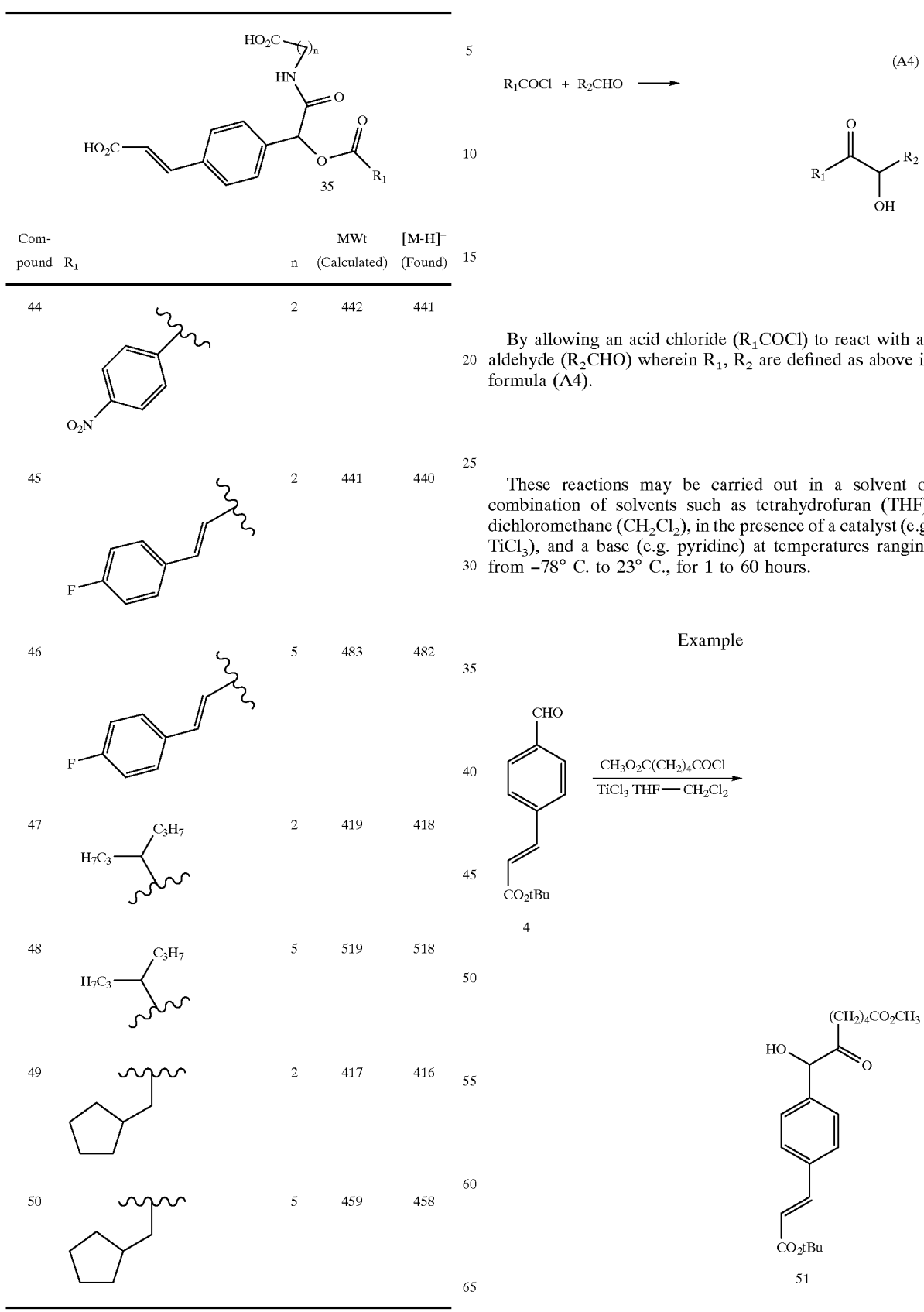

| Compound | R₁ | n | MWt (Calculated) | [M-H]⁻ (Found) |
|---|---|---|---|---|
| 44 | 4-O₂N-C₆H₄-CH₂- | 2 | 442 | 441 |
| 45 | (E)-4-F-C₆H₄-CH=CH- | 2 | 441 | 440 |
| 46 | (E)-4-F-C₆H₄-CH=CH- | 5 | 483 | 482 |
| 47 | (C₃H₇)₂CH- | 2 | 419 | 418 |
| 48 | (C₃H₇)₂CH- | 5 | 519 | 518 |
| 49 | cyclopentyl-CH₂- | 2 | 417 | 416 |
| 50 | cyclopentyl-CH₂- | 5 | 459 | 458 |

General Method for the Synthesis of Compounds (A4)

$$R_1COCl + R_2CHO \longrightarrow$$

(A4)

By allowing an acid chloride ($R_1COCl$) to react with an aldehyde ($R_2CHO$) wherein $R_1$, $R_2$ are defined as above in formula (A4).

These reactions may be carried out in a solvent or combination of solvents such as tetrahydrofuran (THF), dichloromethane ($CH_2Cl_2$), in the presence of a catalyst (e.g. $TiCl_3$), and a base (e.g. pyridine) at temperatures ranging from −78° C. to 23° C., for 1 to 60 hours.

Example

Prepared according to Araneo et al (*Tetrahedron Lett.* 1994, 35, 2213). $^1$H NMR of 51 (400 MHz, CDCl$_3$) δ 1.45 (s, 9H), 1.5 (m, 4H), 2.1–2.3 (m, 4H), 3.6 (s, 3H), 4.6 (s, 1H), 6.25 (d, 1H), 6.97 (d, 2H), 7.25 (d, 2H), 7.5 (d, 1H).

General Methods for the Synthesis of Compounds (A6)

Method 1

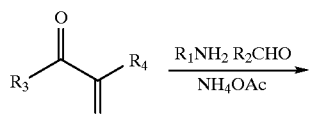

(A5)-1

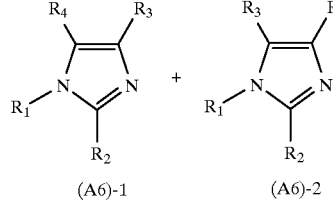

(A6)-1    (A6)-2

By allowing a compound of formula (A5) to react with an aldehyde (R$_2$CHO), a primary amine (R$_1$NH$_2$) and ammonium acetate wherein R$_1$, R$_2$, R$_3$ and R$_4$ are defined as above in formula (A6).

These reactions may be carried out in a solvent such as acetic acid (AcOH) at temperatures ranging from 23° C. to 120° C., for 1 to 60 hours.

Examples

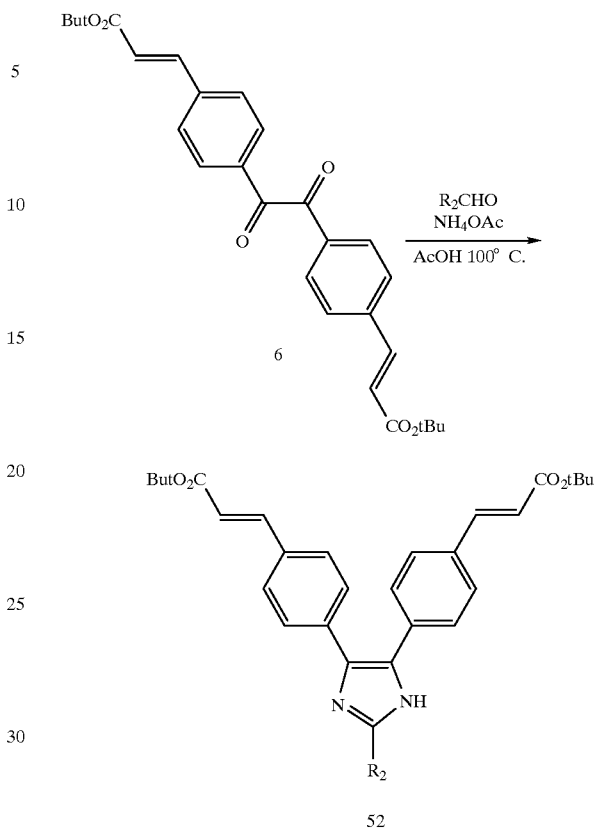

Prepared according to Krieg et al (*Z Naturforsch teil* 1967, 22b, 132).

To 47 mg of 6 (0.1 mmol, 1.0 equiv), R$_2$CHO (0.1 mmol, 1.0 equiv) in 1 mL of acetic acid was added 231 mg of ammonium acetate (3.0 mmol, 30 equiv) in 0.5 mL of acetic acid and the mixture was placed in 100° C. preheated oil bath for 1 hour. The solution was then poured into ether and washed with saturated sodium bicarbonate. The organic layer was dried over sodium sulfate, filtered and concentrated in vacuo to yield the desired imidazoles 52 which were purified by preparative thin layer chromatography with ethyl acetate-hexane or methanol-dichloromethane as eluent.

TABLE 3

52 →(50% TFA—CH$_2$Cl$_2$, 23° C. 1h)→ 53

| Entry | R$_2$ | MWt. (Calc.) | MWt. (Obs.) | Entry | R$_2$ | MWt. (Calc.) | MWt. (Obs.) |
|---|---|---|---|---|---|---|---|
| 54 | 4-(HO$_2$C)C$_6$H$_4$– | 480 | 479 | 61 | 3-F-C$_6$H$_4$– | —* | —* |
| 55 | H | —* | —* | 62 | 5-Br-thien-2-yl | 521 | 522 |
| 56 | 6-NO$_2$-benzo[1,3]dioxol-5-yl | 525 | 526 | 63 | quinolin-2-yl | 487 | 488 |
| 57 | 2-NO$_2$-C$_6$H$_4$– | 481 | 482 | 64 | 6-(MeO$_2$C)-1H-indol-2-yl | 533 | 534 |
| 58 | 4-MeO-C$_6$H$_4$– | —* | —* | 65 | 3,5-F$_2$-C$_6$H$_3$– | —* | —* |
| 59 | 2-NO$_2$-3-MeO-C$_6$H$_3$– (with Me) | 511 | 512 | 66 | 3,4-F$_2$-C$_6$H$_3$– | —* | —* |

TABLE 3-continued
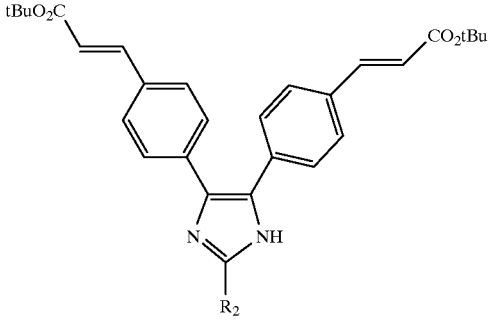
| Entry | R₂ | MWt. (Calc.) | MWt. (Obs.) | Entry | R₂ | MWt. (Calc.) | MWt. (Obs.) |
|---|---|---|---|---|---|---|---|
| 60 | 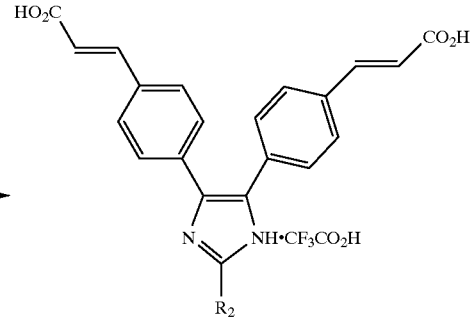 | —* | —* | 67 | 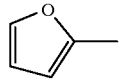 | —* | —* |
| 68 | 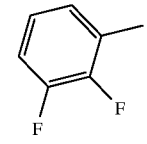 | —* | —* | 79 | 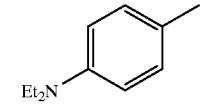 | —* | —* |
| 69 | 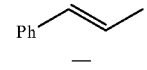 | 482 | 483 | 80 | 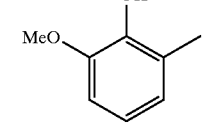 | 560 | 561 |
| 70 | 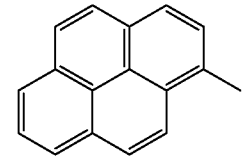 | 442 | 441 | 81 | 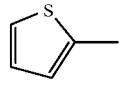 | 536 | 537 |
| 71 | 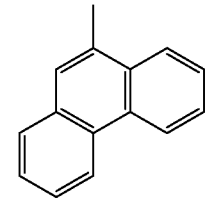 | 494 | 495 | 82 | 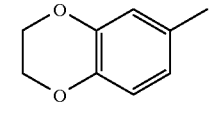 | —* | —* |
| 72 | 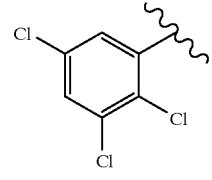 | 526 | 527 | 83 | 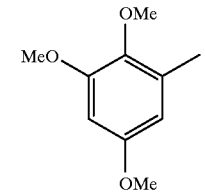 | —* | —* |

TABLE 3-continued

[Structures of compounds 52 and 53 shown: compound 52 with tBuO₂C and CO₂tBu groups on distyryl-diphenyl-imidazole with R₂ substituent, converted via 50% TFA—CH₂Cl₂, 23° C., 1h to compound 53 with HO₂C and CO₂H groups and NH·CF₃CO₂H salt]

| Entry | R₂ | MWt. (Calc.) | MWt. (Obs.) | Entry | R₂ | MWt. (Calc.) | MWt. (Obs.) |
|---|---|---|---|---|---|---|---|
| 73 | 4-NC-C₆H₄- | —* | —* | 84 | pentafluorophenyl | 526 | 527 |
| 74 | 1-methyl-3-indolyl | 489 | 490 | 85 | 3,4-methylenedioxyphenyl | 480 | 481 |
| 75 | Ph | 436 | 435 | 86 | 2,3-dimethyl-4-methoxyphenyl | 494 | 495 |
| 76 | 2,5-difluoro-methylphenyl | —* | —* | 87 | 4-benzyloxyphenyl | 542 | 543 |
| 77 | n-C₅H₁₁ | —* | —* | 88 | 1,1,4,4-tetramethyl-1,2,3,4-tetrahydronaphth-6-yl | 561 | 562 |
| 78 | 2-fluoro-methylphenyl | 454 | 455 | 89 | 5-indanyl | 476 | 477 |

TABLE 3-continued

[Reaction scheme: Compound 52 (di-tert-butyl ester bis-cinnamate imidazole with R₂ substituent) converted with 50% TFA—CH₂Cl₂ at 23°C, 1h to compound 53 (bis-carboxylic acid with NH·CF₃CO₂H)]

52 → 53

| Entry | R₂ | MWt. (Calc.) | MWt. (Obs.) | Entry | R₂ | MWt. (Calc.) | MWt. (Obs.) |
|---|---|---|---|---|---|---|---|
| | | | | 90 | 4-(AcHN)-phenyl | 493 | 494 |

*"—": data not available.

54 (400 MHz, CDCl₃—CD₃OD 10:1) δ 6.23(d, 2H), 7.3–7.48(m, 10H), 7.88(d, 2H), 8.02(d, 2H).
55 (400 MHz, CD₃OD) δ 6.5(d, 2H), 7.52(d, 4H), 7.7(m, 6H), 9.1(s, 1H).
56 (400 MHz, CD₃OD) δ 6.3(s, 2H), 6.52(d, 2H), 7.4–7.9(m, 12H).
57 (400 MHz, CD₃OD) δ 6.52(d, 2H), 7.50–8.36(m, 14H).
58 (400 MHz, CDCl₃—CD₃OD 10:1) δ 3.7(s, 3H), 6.3(d, 2H), 6.85(d, 2H), 7.4(m, 8H), 7.5(d, 2H), 7.85(d, 2H).
59 (400 MHz, CD₃OD) δ 3.98(s, 3H), 6.52(d, 2H), 7.50–7.76(m, 13H).
60 (400 MHz, CDCl₃—CD₃OD 10:1) δ 6.3(d, 2H), 6.5(br s, 1H), 6.85(d, 2H), 7.3–7.6(m, 12H).
61 di-tert-butyl ester(400 MHz, CDCl₃—CD₃OD 6:1) δ 1.4(s, 18H), 6.2(d, 2H), 6.9(t, 1H), 7.2–7.42(m, 11H), 7.58(d, 1H), 7.62(d, 1H).
62 (400 MHz, CD₃OD) δ 6.50(d, 2H), 7.30–8.70(m, 12H).
63 (400 MHz, CD₃OD) δ 6.54(d, 2H), 7.46–8.60(m, 16H).
64 (400 MHz, CD₃OD) δ 3.90(s, 3H), 6.50(d, 2H), 7.50–8.30(m, 13H).
65 di-tert-butyl ester (400 MHz, CDCl₃—CD₃OD 6:1) δ 1.4(s, 18H), 6.2(d, 2H), 6.65(t, 1H), 7.3–7.5(m, 12H).
66 di-tert-butyl ester (400 MHz, CDCl₃—CD₃OD 6:1) δ 1.4(s, 18H), 6.2(dd, 2H), 7.1(q, 1H), 7.3–7.5(m, 10H), 7.6(br d, 1H), 7.7(dd, 1H).
67 di-tert-butyl ester (400 MHz, CDCl₃—CD₃OD 6:1) δ 1.4(s, 18H), 6.2(d, 2H), 7.1(t, 2H), 7.3–7.5(m, 10H), 7.75(m, 1H).
68 (400 MHz, CD₃OD) δ 1.2(t, 6H), 3.48(q, 4H), 6.52(d, 2H), 7.3–8.02(m, 15H).
69 (400 MHz, CD₃OD) δ 3.96(s, 3H), 6.52(d, 2H), 7.04–7.70(m, 13H).
70 (400 MHz, CD₃OD) δ 6.46(d, 2H), 7.14(d, 1H), 7.50–7.80(m, 12H).
71 (400 MHz, CD₃OD) δ 4.32(m, 4H), 6.52(d, 2H), 7.1–7.7(m, 13H).
72 (400 MHz, CD₃OD) δ 3.90–4.02(3s, 9H), 6.50(d, 2H), 6.90–7.80(m, 12H).
73 (400 MHz, CD₃OD) δ 6.5(d, 2H), 7.55(d, 4H), 7.65(m, 6H), 7.95(d, 2H), 8.15(d, 2H).
74 (400 MHz, CD₃OD) δ 3.95(s, 3H), 6.56(d, 2H), 6.9–7.82(m, 14H).
75 (400 MHz, CDCl₃—CD₃OD 10:1) δ 6.34(d, 2H), 7.3–7.4(m, 11H), 7.52(d, 2H), 8.92(d, 2H).
76 di-tert-butyl ester (400 MHz, CDCl₃—CD₃OD 6:1) δ 1.4(s, 18H), 6.2(br d, 2H), 6.9(m, 1H), 7.05(m, 1H), 7.3–7.5(m, 10H).
77 (400 MHz, CDCl₃—CD₃OD 6:1) δ 0.9(m, 5H), 1.3(m, 2H), 1.7(m, 2H), 2.9(t, 2H), 6.35(d, 2H), 7.3–7.6(m, 10H).
78 (400 MHz, CD₃OD) δ 6.50(d, 2H), 7.40–7.9(m, 14H).
79 di-tert-butyl ester (400 MHz, CDCl₃) δ 1.4(s, 18H), 6.3(d, 2H), 7.1(d, 2H), 7.22(d, 1H), 7.34(t, 2H), 7.4–7.7(m, 14H), 7.9(d, 2H).
80 (400 MHz, CD₃OD) δ 6.54(d, 2H), 7.6–8.0(m, 19H).
81 (400 MHz, CD₃OD) δ 6.54(d, 2H), 7.6–8.90(m, 19H).
82 (400 MHz, CD₃OD) δ 6.50(d, 2H), 7.58–8.0(m, 14H).
83 (400 MHz, CD₃OD) δ 3.96(s, 3H), 6.52(d, 2H), 7.36–7.90(m, 13H).
84 (400 MHz, CD₃OD) δ 6.50(d, 2H), 7.55–7.70(m, 10H).
85 (400 MHz, CD₃OD) δ 6.12(s, 2H), 6.56(d, 2H), 7.10–7.60(m, 13H).
86 (400 MHz, CD₃OD) δ 2.20(s, 3H), 2.40(s, 3H), 3.90(s, 3H), 6.52(d, 2H), 7.10–7.70(m, 12H).
87 (400 MHz, CD₃OD) δ 5.20(s, 2H), 6.56(d, 2H), 7.22–7.98(m, 19H).
88 (400 MHz, CD₃OD) δ 1.52(2s, 12H), 1.74(s, 4H), 2.42(s, 3H), 6.52(d, 2H), 7.40–7.68(m, 13H).
89 (400 MHz, CD₃OD) δ 1.12(t, 2H), 3.0(m, 4H), 6.56(d, 2H), 7.52–7.62(m, 13H).
90 (400 MHz, CD₃OD) δ 2.14(s, 3H), 6.54(d, 2H), 7.58–8.0(m, 14H).

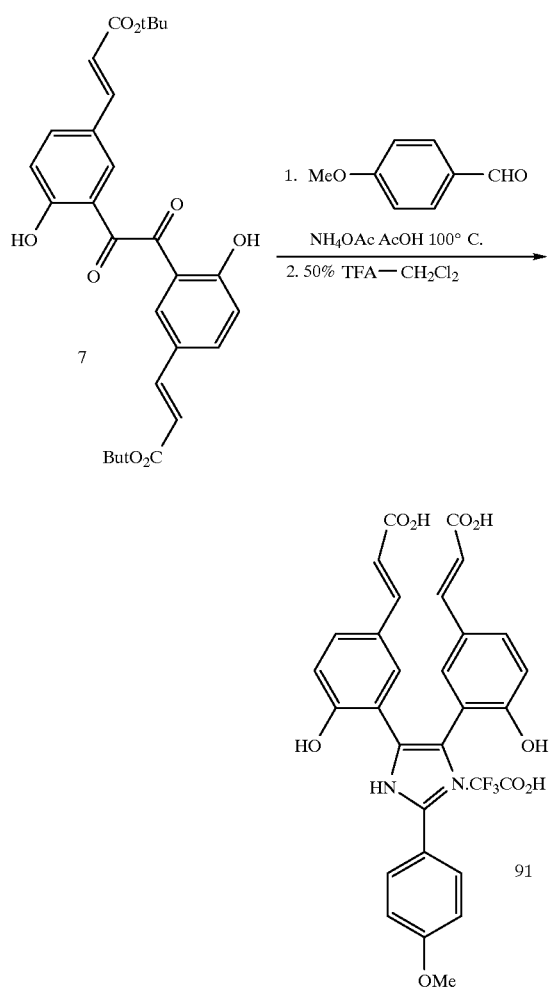
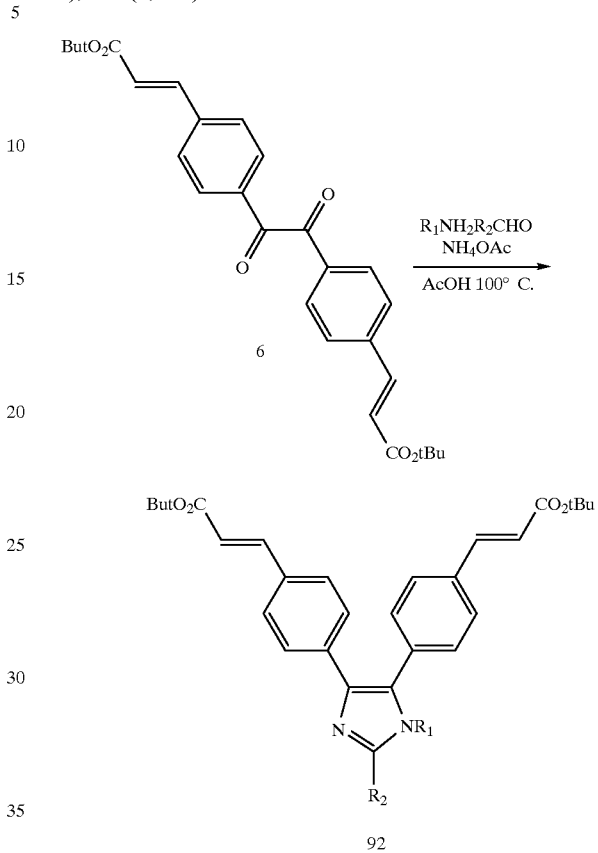
Prepared according to Krieg et al (*Z Naturforsch teil* 1967, 22b, 132). $^1$H NMR of 91 (400 MHz, CD$_3$OD) δ 3.9 (s,3H), 6.2 (d, 2H), 6.95 (d, 2H), 7.2 (d, 2H), 7.4–7.6 (m, 6H), 7.9 (d, 2H).
Prepared according to Krieg et al (*Z Naturforsch teil* 1967, 22b, 132).
TABLE 4
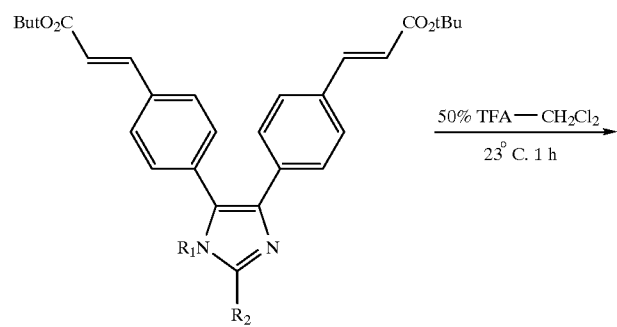

TABLE 4-continued
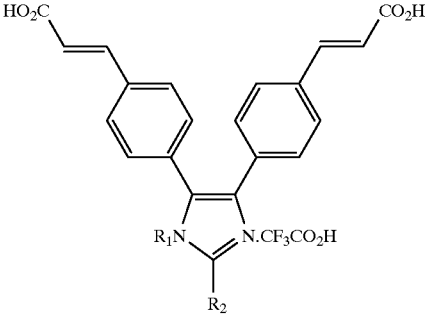
93
| Entry | R₁ | R₂ | MWt (Calc.) | MWt (Obs.) |
|---|---|---|---|---|
| 94 | n-C₄H₉ | H | 416 | 415 |
| 95 | n-C₄H₉ | 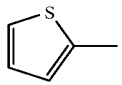 | 498 | 497 |
| 96 | Ph | 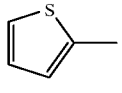 | 518 | 517 |
| 97 | n-C₄H₉ | 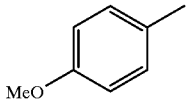 | 522 | 521 |
| 98 | Ph | 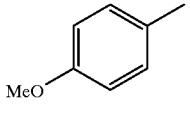 | 542 | 541 |
| 99 | Ph | H | 436 | 435 |
| 100 | 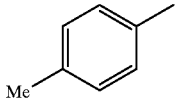 | (4-Me-C₆H₄) | 582 | 581 |
94(400MHz, CD₃OD)δ 0.8(t, 3H), 1.22(m, 2H), 1.62(m, 2H), 4.10(t, 2H), 6.42(d, 1H), 6.58(d, 1H), 7.32–7.80(m, 10H), 9.18(s, 1H).
95(400MHz, CD₃OD)δ 0.64(t, 3H), 1.04(m, 2H), 1.58(m, 2H), 4.20(t, 2H), 6.42(d, 1H), 6.62(d, 1H), 7.42–8.0(m, 13H).
96(400MHz, CD₃OD)δ 6.42(2d, 2H), 7.12–7.68(m, 18H).
97(400MHZ, CD₃OD)δ 0.6(t, 3H), 1.0(m, 2H), 1.38(m, 2H), 4.12(t, 2H), 3.84(s, 3H), 6.42(d, 1H), 6.62(d, 1H), 7.22–7.8(m, 13H).
98(400MHz, CD₃OD)δ 3.80(s, 3H), 6.44(2d, 2H), 6.94–7.68(m, 19H).
99(400MHz, CD₃OD)δ 6.44(2d, 2H), 7.20–7.60(m, 15H), 9.2(s, 1H).
100(400MHz, CD₃OD)δ 1.22(s, 9H), 2.40(s, 3H), 6.36–6.44(2d, 2H), 7.26–7.60(m, 18H).

Method 2

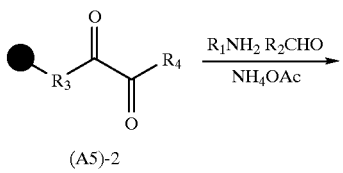

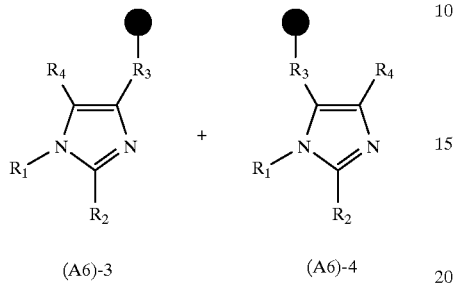

By allowing a polymer bound compound of formula (A5)-2 to react with an aldehyde ($R_2$CHO), a primary amine ($R_1NH_2$) and ammonium acetate wherein $R_1$, $R_2$, $R_3$ and $R_4$ are defined as above in formula (A6).

These reactions may be carried out on functionalized cross linked polystyrene polymers such as Merrifield resin, Wang resin, Rink resin, "TENTAGEL™" which is a polyethylene-polystyrene polymer resin, in a solvent such as acetic acid (AcOH) at temperatures ranging from 23° C. to 120° C., for 1 to 60 hours. The product maybe released from the polymer using conditions known to 5 those skilled in the art.

Examples

To resin 17 were added excess $NH_4OAc$ and $R_2CHO$ and acetic acid and the mixture was heated at 100° C. for 15 hours, cooled to 23° C. and washed with methanol and dichloromethane and dried under vacuum. The trifluoroacetate salts of imidazoles 101 were isolated following treatment of the resin with a solution of 20% trifluoroacetic acid in dichloromethane for 20 minutes at 23° C.

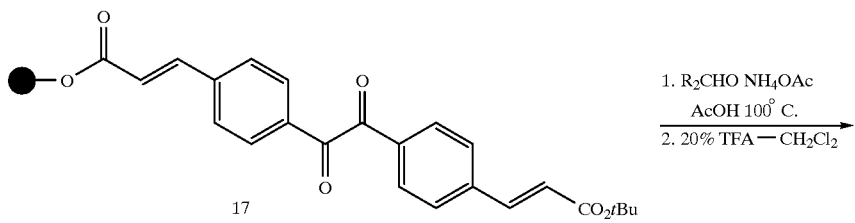

17

1. $R_2CHO$ $NH_4OAc$
   AcOH 100° C.
2. 20% TFA — $CH_2Cl_2$

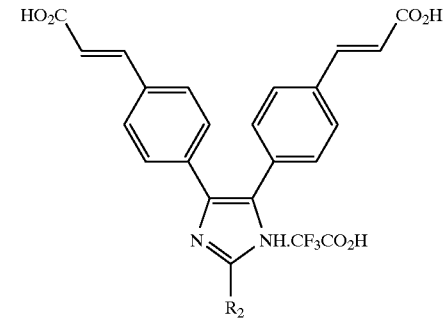

101

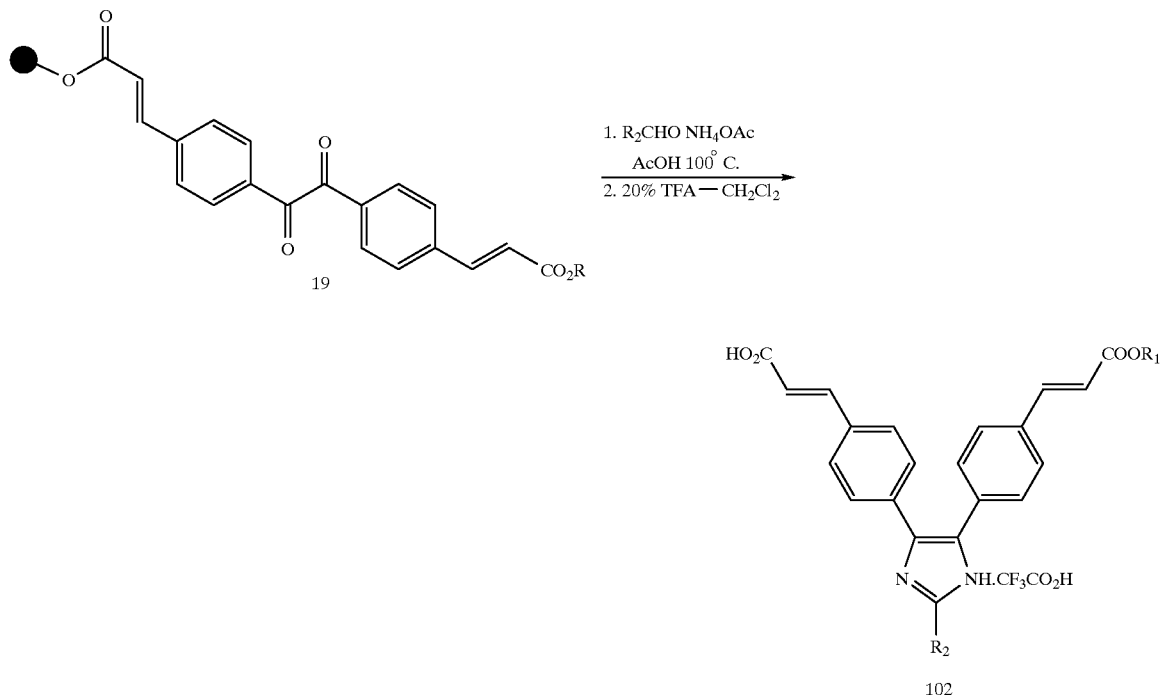
Same procedure as imidazoles 101.
TABLE 5
| Entry | R₁ | R₂ | MWt. (Calc.) | MWt. (Obs.) |
|---|---|---|---|---|
| 103 | Me | 2-nitro-methylphenyl | 495 | 496 |
| 104 | 4-fluorophenyl | 2-nitro-3-methyl-methoxyphenyl | 620 | 621 |
| 105 | 3-methoxyphenyl | 2-nitro-methylphenyl | 602 | 603 |
| 106 | 3-methylphenyl | 2-nitro-methylphenyl | 586 | 587 |

TABLE 5-continued
| Entry | R₁ | R₂ | MWt. (Calc.) | MWt. (Obs.) |
|---|---|---|---|---|
| 107 | 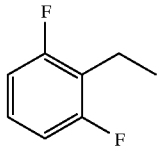 | 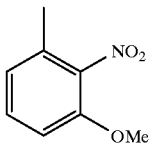 | 638 | 639 |
| 108 | 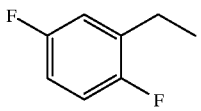 | 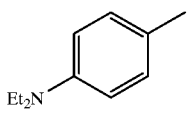 | 634 | 635 |
| 109 | 2-propyl | 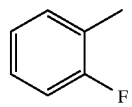 | 496 | 497 |
| 110 | 2-propyl | 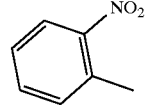 | 523 | 524 |
| 111 | 2-propyl | 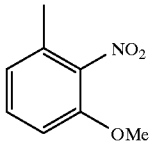 | 553 | 554 |
| 112 | 2-indanyl | 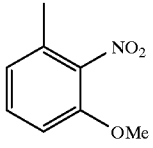 | 627 | 628 |
| 113 | 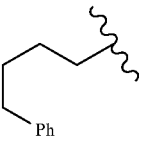 | 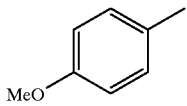 | 626 | 627 |

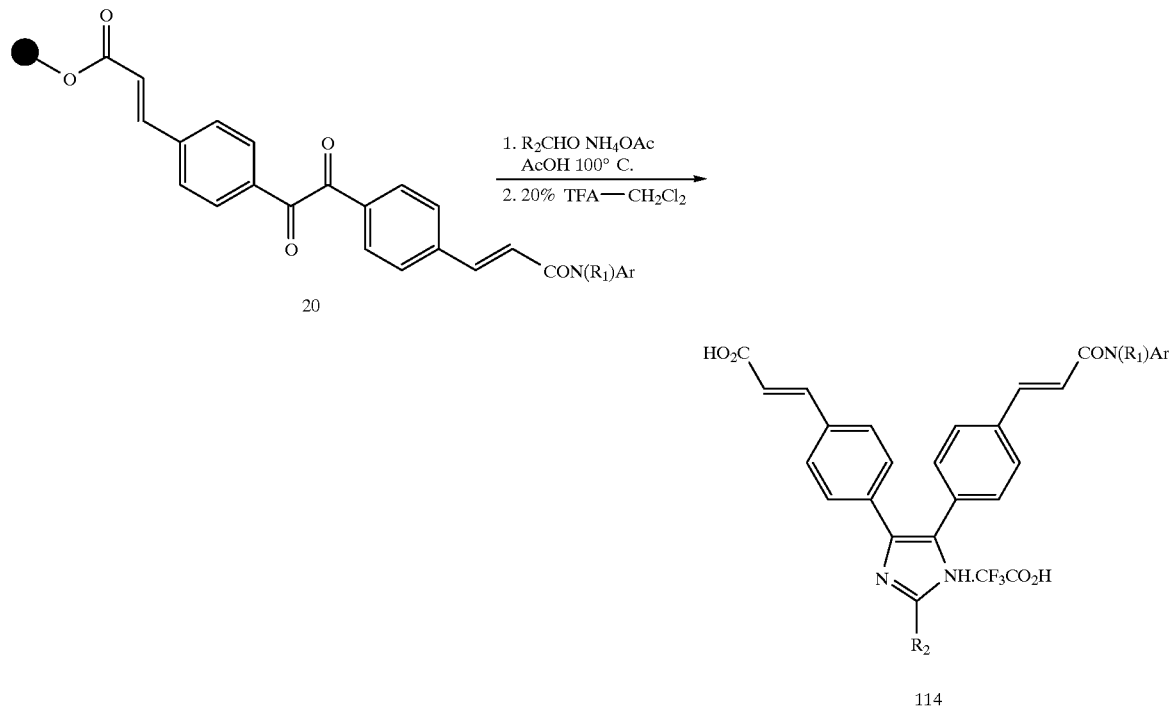
Same procedure as imidazoles 101.
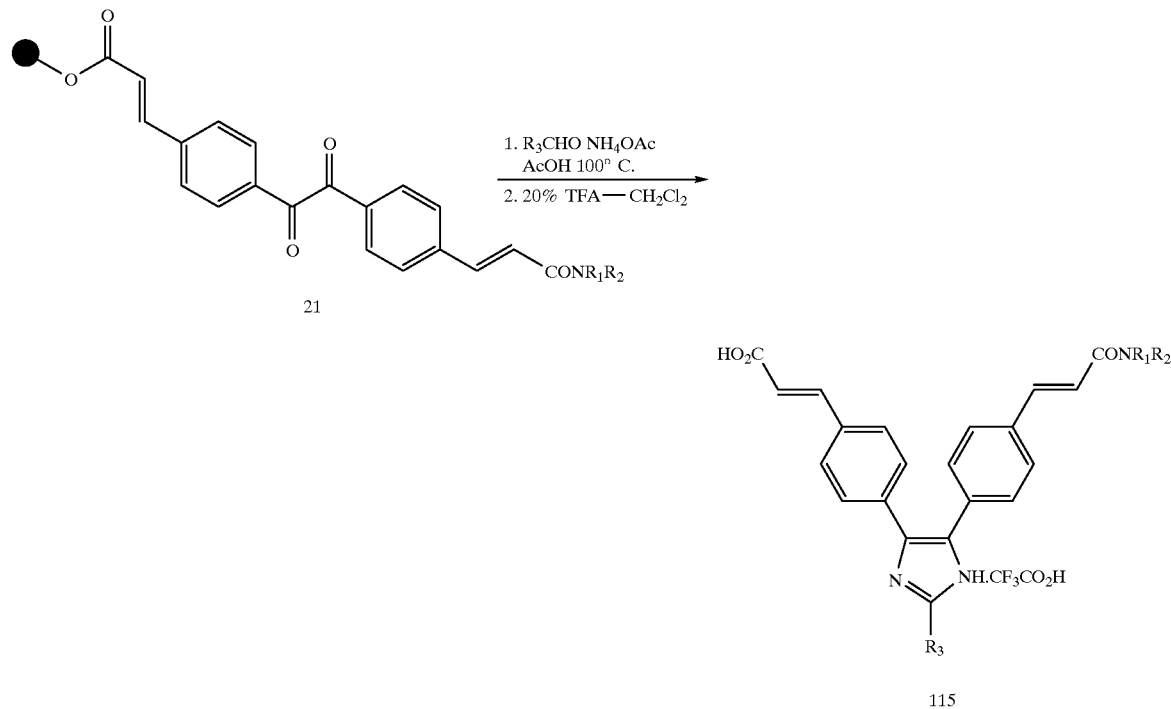
Same procedure as imidazoles 101.

TABLE 6

| Entry | R₁ | R₂ | MWt. (Calc.) | MWt. (OBs.) |
|---|---|---|---|---|
| 116 | 2-fluorophenyl | 4-methoxyphenyl | 559 | 560 |
| 117 | cyclohexylethyl | 4-methoxyphenyl | 562 | 563 |
| 118 | 3-(piperidin-1-yl)propyl | 5-bromothiophen-2-yl | 633 | 634 |
| 119 | 4-phenylbutyl | 2-methoxy-6-nitrophenyl (3-methyl-2-nitro-...) | 642 | 643 |
| 120 | (tetrahydrofuran-2-yl)methyl | 4-(diethylamino)phenyl | 592 | 593 |
| 121 | (tetrahydrofuran-2-yl)methyl | 2,3-dihydrobenzo[1,4]dioxin-6-yl | 579 | 580 |
| 122 | n-propyl | 4-methoxyphenyl | 508 | 509 |
| 123 | n-propyl | 5-bromothiophen-2-yl | 562,564 | 563,565 |

TABLE 6-continued
| Entry | R₁ | R₂ | MWt. (Calc.) | MWt. (OBs.) |
|---|---|---|---|---|
| 124 | n-butyl | 2,5-difluoro-methylphenyl | 528 | 529 |
| 125 | n-heptyl | 2-nitro-methylphenyl | 579 | 580 |
| 126 | n-octyl | 3-fluoro-methylphenyl | 566 | 567 |
| 127 | n-octyl | 4-(diethylamino)-methylphenyl | 619 | 620 |
| 128 | -(CH₂)₃Ph | methyl-benzodioxane | 612 | 613 |
Method 3
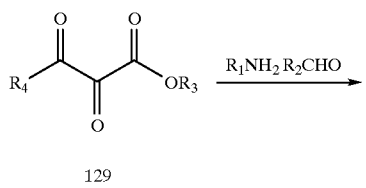
129
$\xrightarrow{R_1NH_2 \ R_2CHO}$
-continued
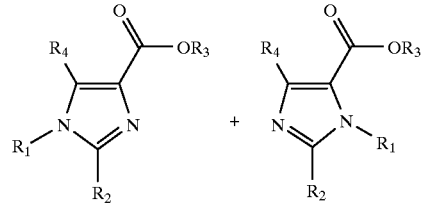
(A6)-5     (A6)-6

By allowing a compound of formula (129) (*J. Org. Chem.*, 1995, 60, 8231; *J. Org. Chem.*, 1993, 58, 4785) to react with an aldehyde (R$_2$CHO), a primary amine (R$_1$NH$_2$) and ammonium acetate wherein R$_1$, R$_2$, R$_3$ and R$_4$ are defined as above in formula (A6).

These reactions may be carried out in a solvent such as acetic acid (AcOH) at temperatures ranging from 23° C. to 120° C., for 1 to 60 hours.

Examples

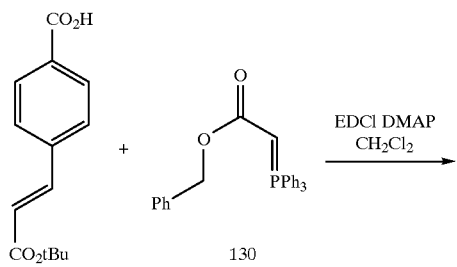

Prepared according to Wasserman et al (*J. Org. Chem.*, 1995, 60, 8231; *J. Org. Chem.*, 1993, 58, 4785). Benzyl (triphenylphosphoranylidene) acetate (130) was purchased from Aldrich chemical company and used directly. $^1$H NMR of 131 (400 MHz, CDCl$_3$) δ 1.5 (s, 9H), 4.62 (s, 2H), 6.3 (d, 1H), 6.62 (d, 2H), 7.05 (t, 2H), 7.1 (t, 1H), 7.38–7.8 (m, 20H). TLC: R$_f$=0.5 (30% ethyl acetate-hexane).

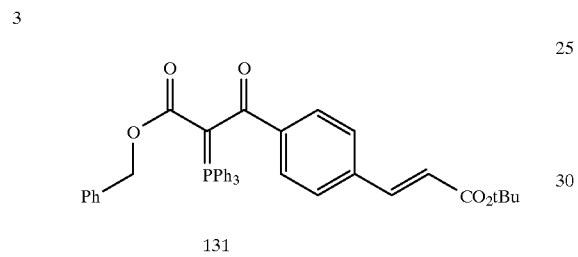

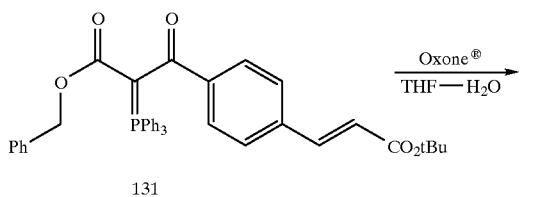

Prepared according to Wasserman et al (*J. Org. Chem.*, 1995, 60, 8231; *J. Org. Chem.*, 1993, 58, 4785). $^1$H NMR of 132 (400 MHz, CDCl$_3$) δ 1.5 (s, 9H), 5.1 (s, 2H), 5.15 (br s, 2H, 2 x H—O), 6.4 (d, 1H), 6.95 (d, 2H), 7.1 (t, 2H), 7.18 (t, 1H), 7.4 (d, 2H), 7.5 (d, 1H), 7.9 (d, 2H). TLC: R$_f$=0.7 (30% ethyl acetate-hexane).

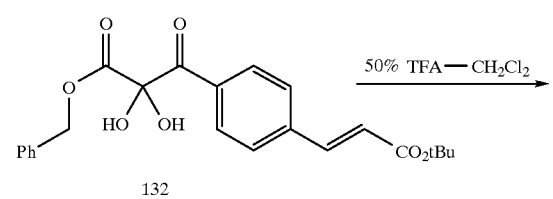

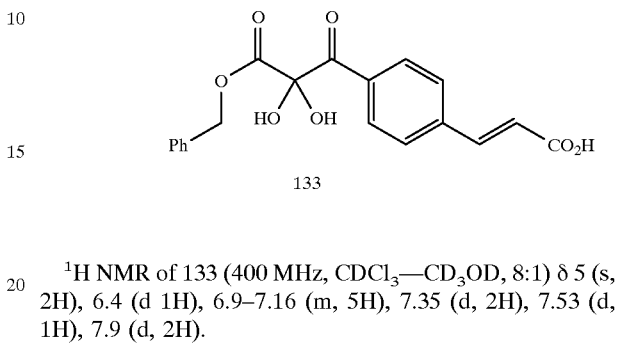

$^1$H NMR of 133 (400 MHz, CDCl$_3$—CD$_3$OD, 8:1) δ 5 (s, 2H), 6.4 (d 1H), 6.9–7.16 (m, 5H), 7.35 (d, 2H), 7.53 (d, 1H), 7.9 (d, 2H).

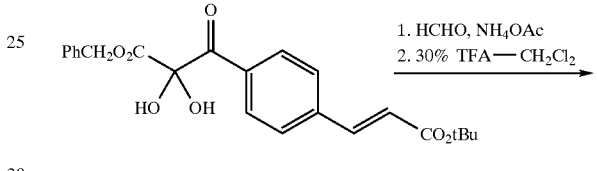

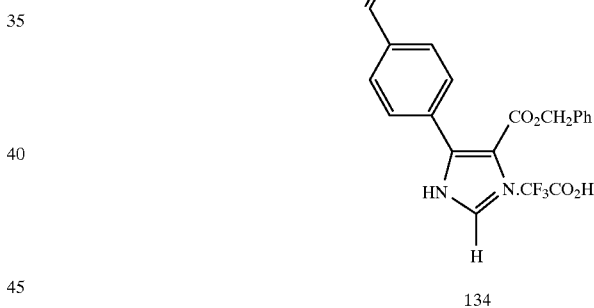

Prepared according to Brackeen et al (*Tetrahedron Letters* 1994, 35, 1635). For other approaches to imidazole-4-carboxylates see: a) Nunami et al (*J. Org. Chem.* 1994, 59, 7635). b) Heindel et al (*Tetrahedron Letters* 1971, 1439). $^1$H NMR of 134 (400 MHz, 8:1 CDCl$_3$—CD$_3$OD) δ 5.2 (s, 2H), 6.4 (d, 1H), 7.25 (br s, 5H), 7.5 (d, 2H), 7.6 (d, 1H), 7.7 (d, 2H), 8.3 (s, 1H).

Method 4

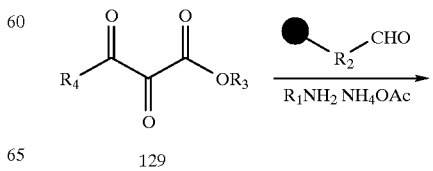

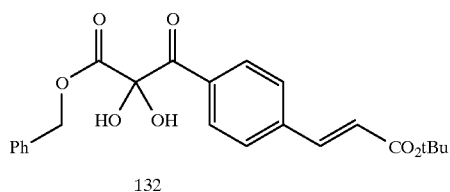

79
-continued

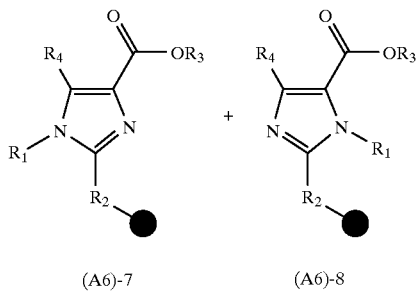

(A6)-7    (A6)-8

By allowing a compound of formula (129) to react with a polymer bound aldehyde ($R_1CHO$), a primary amine ($R_2NH_2$) and ammonium acetate wherein $R_1$, $R_2$, $R_3$ and $R_4$ are defined as above in formula (A6).

This reaction may be carried out on functionalized cross linked polystyrene polymers such as Merrifield resin, Wang resin, Rink resin, Tentagel™ resin, in a solvent such as acetic acid (AcOH) at temperatures ranging from 23° C. to 120° C., for 1 to 60 hours. The product maybe released from the polymer using conditions known to those skilled in the art.

Examples

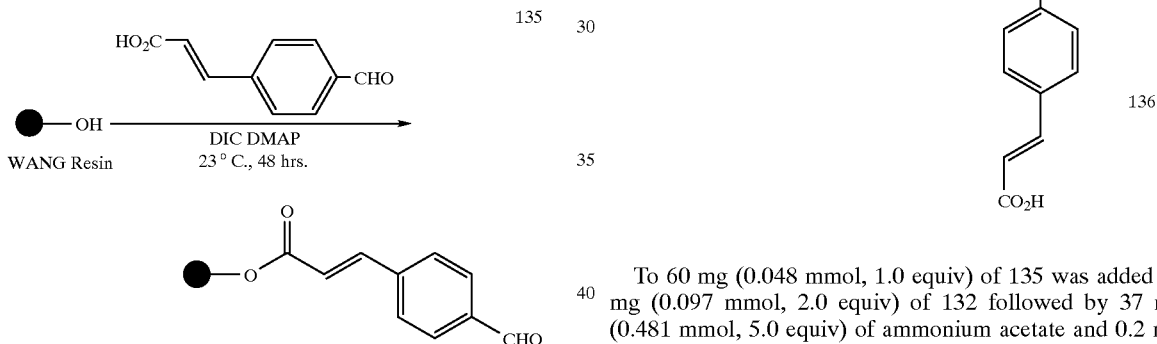

For leading references see: a) Mathias (*Synthesis*, 1979, 561). b) Sarantakis et al (*Biochem. Biophys. Res. Commun.* 1976, 73, 336). c) Hudson et al (*Peptide Chemistry* 1985 (Kiso, Y., ed.), 1986, Protein Research Foundation, Osaka.). d) Wang (*J. Am. Chem. Soc.* 1973, 95, 1328). e) Lu et al (*J. Org. Chem.* 1981, 46, 3433). To 6 mmol (1 equiv) of Wang resin in 130 mL of dry dimethylformamide was added 18 mmol (3 equiv) of diisopropylcarbodiimide and the mixture was sonnicated for 4 hours (final bath temperature was 37° C.). 4-Formylcinnamic acid (18 mmol, 3 equiv) and 4-dimethylaminopyridine (6 mmol, 1 equiv) were added and the mixture was magnetically stirred for 48 hours at ambient temperature. The resin was filtered and thoroughly washed with dimethylforamide (500 mL), methanol (500 mL), dichloromethane (500 mL) and methanol (500 mL) and dried in vacuo (0.1 mmHg) for 24 hours. A coupling yield of 80% was established by cleaving 100 mg of the resin with a solution of 20% trifluoroacetic acid in dichloromethane for 20 min at ambient temperature.

80

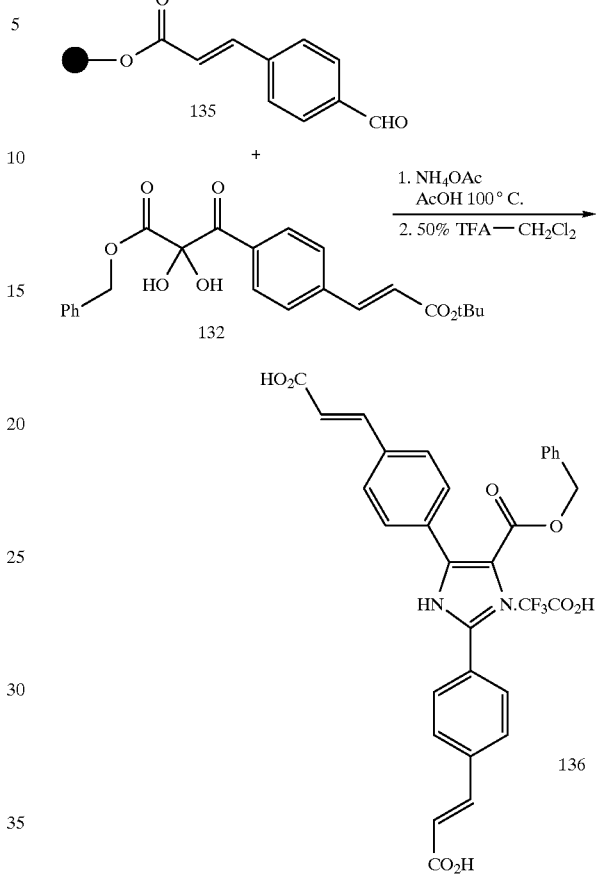

To 60 mg (0.048 mmol, 1.0 equiv) of 135 was added 40 mg (0.097 mmol, 2.0 equiv) of 132 followed by 37 mg (0.481 mmol, 5.0 equiv) of ammonium acetate and 0.2 mL of acetic acid. The mixture was heated to 100° C. for 15 hours, filtered, washed with dimethylformamide, dichloromethane, methanol and dichloromethane. The crude product was isolated by treatment of the polymer with a solution of 50% trifluoroacetic acid in dichloromethane for 1 hour at 23° C. The solvent was removed and the residue was purified by preparative thin layer chromatography (20% methanol-dichloromethane eluent). $^1$H NMR of 136 (400 MHz, $CD_3OD$) δ 5.15 (s, 2H), 6.48 (d, 1H), 6.55 (d, 1H), 7.25 (br s, 4H), 7.5–7.8 (m, 9H), 8.1 (d, 1H). MS (ESI negative ion) [M–H]⁻: 493;

Method 5

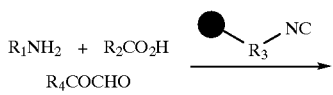

81

-continued

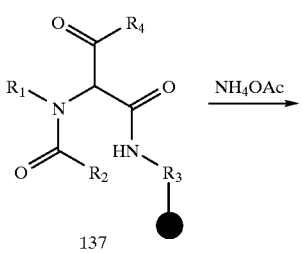

137

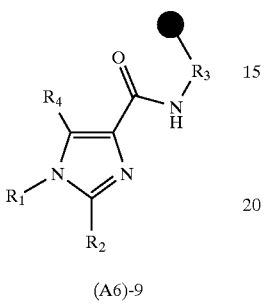

(A6)-9

By allowing a primary amine (R₁NH₂), a carboxylic acid (R₂CO₂H) and a ketoaldehyde (R₄COCHO) to react with a polymer bound isocyanide (R₃NC) and by subsequently cyclizing compound 137 with ammonium acetate wherein $R_1$, $R_2$, $R_3$ and $R_4$ are defined as above in formula (A6).

The first step in this reaction may be carried out on functionalized cross linked polystyrene resins such as Merrifield resin, Wang resin, Rink resin, "TENTAGEL™" which is a polyethylene-polystyrene polymer resin, in a solvent or a combination of solvents such as dichloromethane (CH₂Cl₂), chloroform (CHCl₃), methanol (MeOH), tetrahydrofuran (THF) or acetonitrile (CH₃CN), in the presence or absence of a catalyst (e.g. ZnCl₂, MgBr₂) at temperatures ranging from −78° C. to 80° C., for 1 to 60 hours. The second step in this reaction may be carried out in a solvent such as acetic acid (AcOH) at temperatures ranging from 23° C. to 120° C., for 1 to 60 hours.

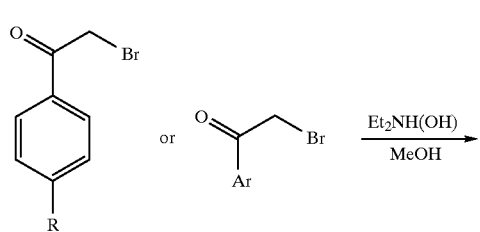

138

Ar = 2-naphthyl, 3,4-dichlorophenyl, 2,5-dimethoxyphenyl, and

82

-continued

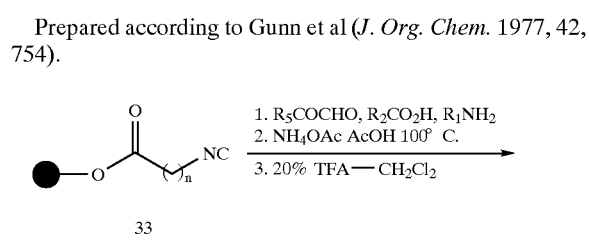

R = CH₃, CF₃, NO₂, CH₃O, CF₃O, F, Cl, Br, Ph

Prepared according to Gunn et al (*J. Org. Chem.* 1977, 42, 754).

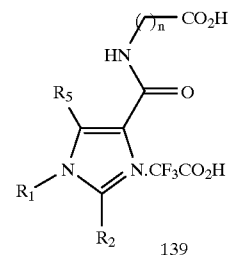

33

1. R₅COCHO, R₂CO₂H, R₁NH₂
2. NH₄OAc AcOH 100° C.
3. 20% TFA—CH₂Cl₂

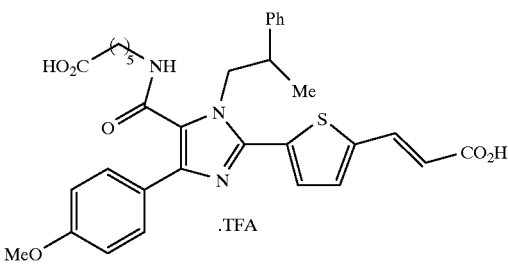

139

Prepared according to Zhang et al (*Tetrahedron Letters* 1996, 37, 751).

140

Prepared according to Zhang et al (*Tetrahedron Letters* 1996, 37, 751). ¹H NMR of mono tert-butyl ester of 140 (400 MHz, CDCl₃) δ 1.1 (m,2H), 1.2 (d,3H), 1.3 (m,2H), 1.5 (s,9H), 1.56 (m,2H), 2.2 (m,2H), 2.9 (m,1H), 3.1 (m,1H), 3.2 (m,1H), 3.8 (s,3H), 4.6 (m,2H), 6.1 (d,1H), 6.9 (t,4H), 7.1 (m,5H), 7.4 (d, 2H), 7.6 (d,1H).

Method 6

83

-continued

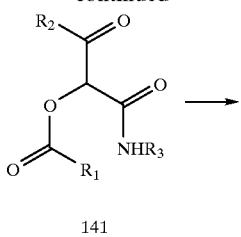

141

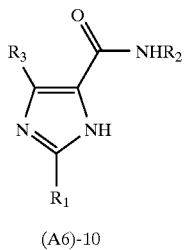

(A6)-10

By allowing a carboxylic acid ($R_1CO_2H$) to react with an isocyanide ($R_3NC$) and a ketoaldehyde ($R_2COCHO$) and by allowing compound 141 to cyclize in the presence of ammonium acetate, wherein $R_1$, $R_2$, and $R_3$ are defined as above in formula (A6).

The first step in this reaction reaction may be carried out in a solvent or a combination of solvents such as dichloromethane ($CH_2Cl_2$), chloroform ($CHCl_3$), methanol (MeOH), tetrahydrofuran (THF), acetonitrile ($CH_3CN$), in the presence or absence of a catalyst (e.g. $ZnCl_2$, $MgBr_2$) at temperatures ranging from −78° C. to 80° C., for 1 to 60 hours. The second step in this reaction may be carried out in a solvent such as acetic acid (AcOH) at temperatures ranging from 23° C. to 120° C., for 1 to 60 hours.

Examples

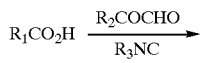

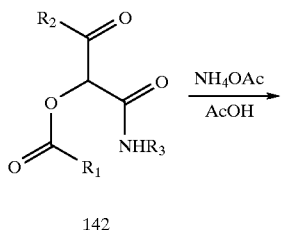

142

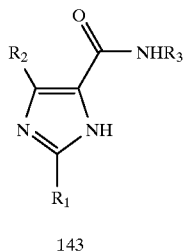

143

84

Prepared according to Bossio et al (*Liebigs Ann. Chem.* 1991, 1107).

To an ethyl ether mixture of the carboxylic acid and ketoaldehyde at 0° C. was added dropwise an ethyl ether solution of the isocyanide. The mixture was warned to 25° C. and stirred for 2 hours to 3 days. The solution was diluted with ethyl acetate, washed with saturated sodium bicarbonate and dried over sodium sulfate. The solvent was removed in vacuo and the residue was purified by silica gel chromatography to yield α-Acyloxy-β-ketoamide 142.

A solution of the α-Acyloxy-β-ketoamide 142 (1 equiv) and ammonium acetate (30 equiv) in acetic acid was heated at 100° C. for 2 to 15 hours. The reaction was cooled to 23° C., diluted with ethyl acetate, washed with saturated sodium bicarbonate and dried over sodium sulfate. Solvent was removed in vacuo and the crude mixture was sepaprated by silica gel chromatography to provide imidazole 143.

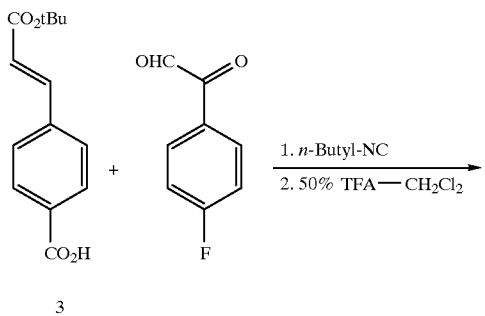

144

$^1$H NMR of 144 (400 MHz, $d_6$-acetone) δ 0.85 (t, 3H), 1.2–1.6 (m, 4H), 3.3 (m, 2H), 6.55 (s, 1H), 6.62 (d, 1H), 7.3 (t, 2H), 7.7 (d, 1H), 7.82 (d, 2H), 8.1 (d, 2H), 8.25 (dd, 2H).

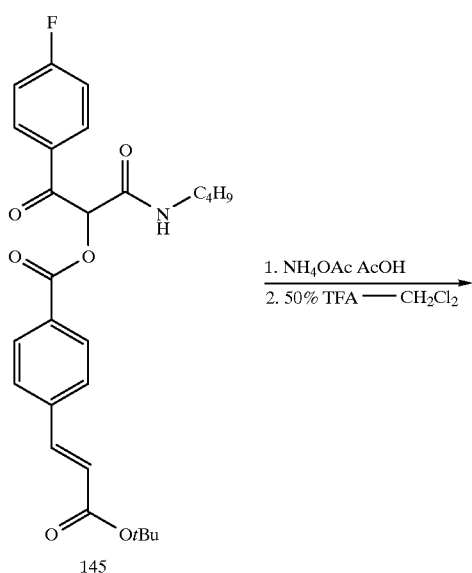

145

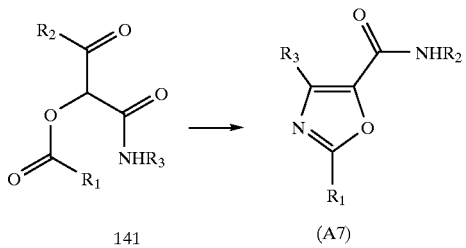

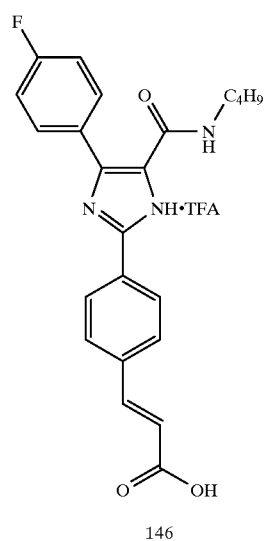

146

¹H NMR of 146 (400 MHz, d₆-acetone) δ 0.9 (t, 3H), 1.4 (m, 2H), 1.6 (m, 2H), 3.35 (m, 2H), 6.58 (d, 1H), 7.12 (t, 2H), 7.65 (d, 1H), 7.78 (d, 2H), 8.1 (s br, 1H), 8.05 (m, 1H), 8.2 (d, 2H).

General Method for the Synthesis of Compounds (A7)

$R_1CO_2H + R_2COCHO + R_3NC \longrightarrow$

-continued

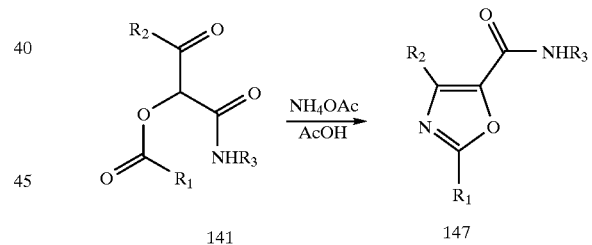

141      (A7)

By allowing a carboxylic acid ($R_1CO_2H$) to react with an isocyanide ($R_3NC$) and a ketoaldehyde ($R_2COCHO$) wherein $R_1$, $R_2$, and $R_3$ are defined as above in formula (A7) and by allowing compound 141 to cyclize in the presence of ammonium acetate.

The first step in this reaction reaction may be carried out in a solvent or a combination of solvents such as dichloromethane ($CH_2Cl_2$), chloroform ($CHCl_3$), methanol (MeOH), tetrahydrofuran (THF), acetonitrile ($CH_3CN$), in the presence or absence of a catalyst (e.g. $ZnCl_2$, $MgBr_2$) at temperatures ranging from −78° C. to 80° C., for 1 to 60 hours. The second step in this reaction may be carried out in a solvent such as acetic acid (AcOH) at temperatures ranging from 23° C. to 120° C., for 1 to 60 hours.

Examples

Prepared according to Bossio et al (*Liebigs Ann. Chem.* 1991, 1107).

A solution of the α-Acyloxy-β-ketoamide 141 (1 equiv) and ammonium acetate (2 equiv) in acetic acid was heated at 100° C. for 2 to 15 hours. The reaction was cooled to 23° C., diluted with ethyl acetate, washed with saturated sodium bicarbonate and dried over sodium sulfate. Solvent was removed in vacuo and the crude oxazole 147 was purified by silica gel chromatography.

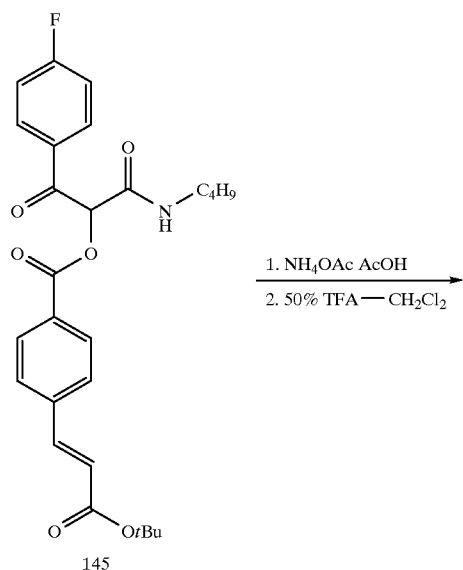

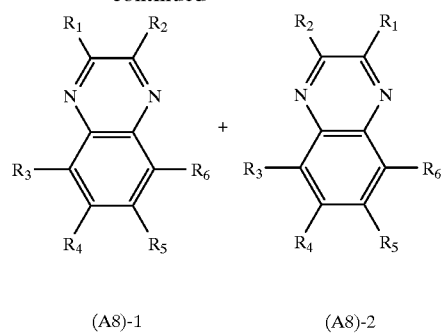

By allowing a compound of formula (A5) to react with compound of formula (149) wherein $R_1$, $R_2$, $R_3$, $R_4$, $R_5$, and $R_6$ are defined as above in formula (A8).

These reactions may be carried out in a solvent or a combination of solvents such as dioxane or acetic acid (AcOH) at temperatures ranging from 23° C. to 120° C., for 1 to 60 hours.

Examples

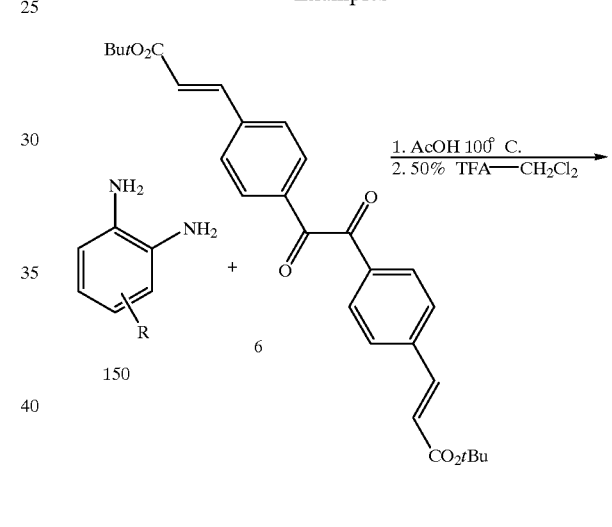

$^1$H NMR of 148 (400 MHz, $d_6$-acetone) δ 0.9 (t, 3H), 1.4 (m, 2H), 1.6 (m, 2H), 3.42 (m, 2H), 6.63 (d, 1H), 7.2 (t, 2H), 7.7 (d, 1H), 7.9 (d, 2H), 8.18 (s br, 1H), 8.25 (d, 2H), 8.6 (m, 1H).

General Methods for the Synthesis of Compounds (A8) and (A9)

Method 1

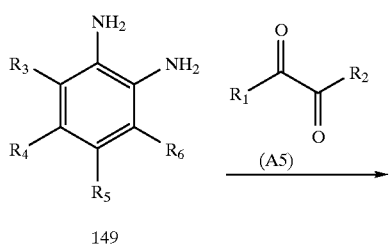

A solution of 0.1 mmol of diamine 150 and 0.1 mmol of 6 in 1.2 mL of 1,4-dioxane-acetic acid (5:1) was heated at 100° C. Upon completion of the reaction as judged by thin layer chromatography, ethyl acetate was added and the organic layer was washed with water, 0.5M citric acid, 10% sodium bicarbonate and dried over sodium sulfate. The compounds were purified using silica gel chromatography.

TABLE 7

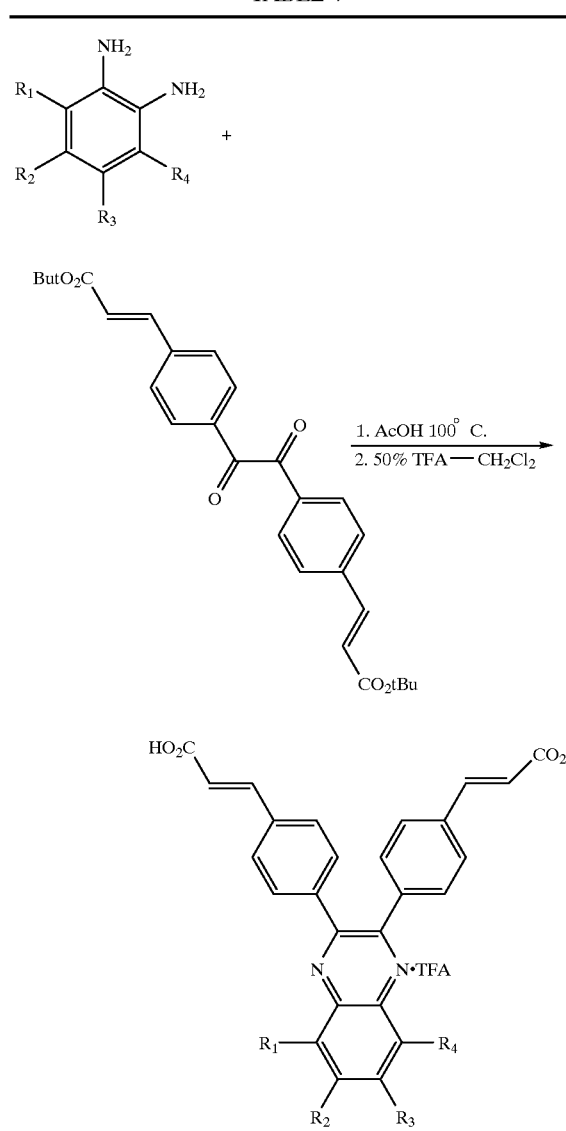

| Compound | $R_1$ | $R_2$ | $R_3$ | $R_4$ |
|---|---|---|---|---|
| 152 | H | H | $NO_2$ | H |
| 153 | H | Cl | Cl | H |
| 154 | H | H | $CH_3$ | H |
| 155 | H | H | $CO_2H$ | H |
| 156 | H | H | $CO_2Me$ | H |
| 157 | H | H | H | H |

152(400MHz, $CD_3OD$)δ 6.5(d, 2H), 7.3(s, 1H), 7.4–7.8(m, 10H), 7.9(s, 1H), 8.05(d, 1H). MS ESI (pos ion) for [M+H]$^+$: 468(calculated 467).
153(400MHz, $CD_3OD$)δ 6.48(d, 2H), 7.5(dd, 8H), 7.6(d, 2H), 8.24(s, 2H). MS ESI (pos ion) for [M+H]$^+$: 491, 492(calculated 490, 491).
154(400MHz, $CD_3OD$)δ 3.3(s, 3H), 6.5(d, 2H), 7.59(s, 8H), 7.62(d, 2H), 8.3(d, 1H), 8.55(d, 1H), 8.95(s, 1H). MS ESI (pos ion) for [M+H]$^+$: 437(calculated 436).
155(400MHz, $d_6$-DMSO)δ 6.56(d, 2H), 7.5(m, 6H), 7.65(d, 4H), 8.2(d, 1H), 8.3(d, 1H), 8.6(s, 1H). MS ESI (neg ion) for [M–H]$^-$: 465(calculated 466).
156(400MHz, $CD_3OD$)δ 6.56(d, 2H), 7.5(s br, 8H), 7.65(d, 2H), 8.2(d, 1H), 8.3(d, 1H), 8.7(s, 1H). MS ESI (neg ion) for [M–H]$^-$: 479(calculated 480).
157(400MHz, $d_6$-DMSO)δ 6.52(d, 2H), 7.54–8.16(m, 14H).

Method 2

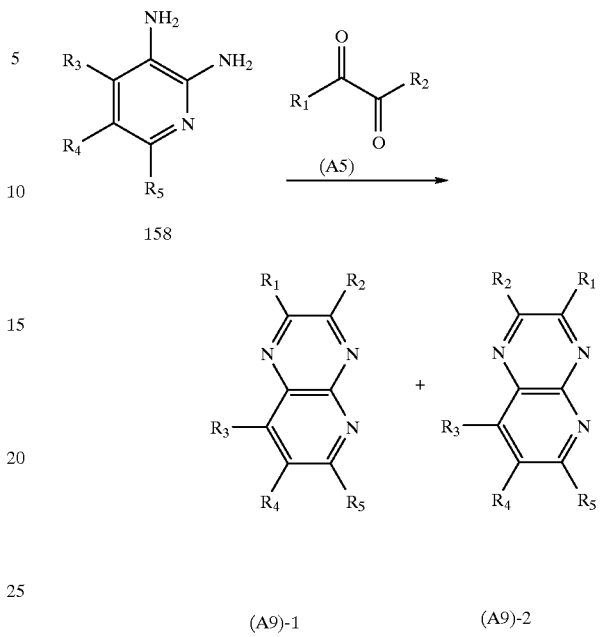

By allowing a compound of formula (A5) to react with compound of formula (158) wherein $R_1$, $R_2$, $R_3$, $R_4$, $R_5$ are defined as above in formula (A9).

These reactions may be carried out in a solvent or a combination of solvents such as dioxane or acetic acid (AcOH) at temperatures ranging from 23° C. to 120° C., for 1 to 60 hours.

Examples

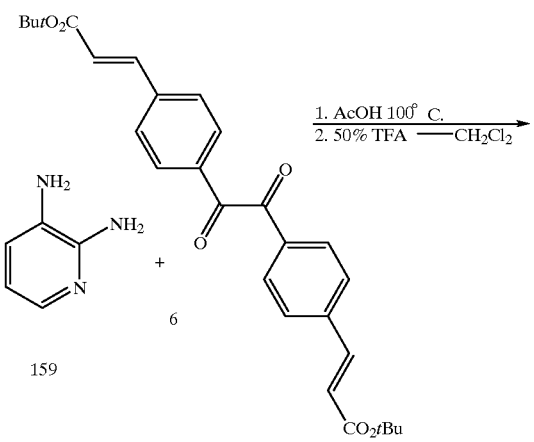

-continued

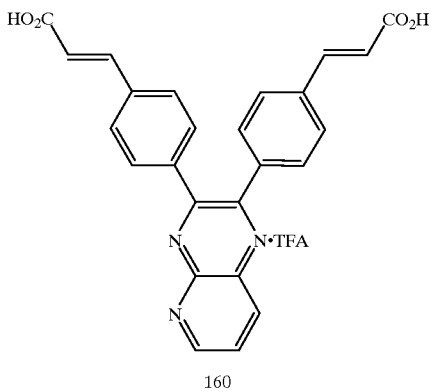

160

¹H NMR of 160 (400 MHz, CD₃OD) δ 6.5 (d, 2H), 7.5–7.7 (m, 12H), 7.95 (m, 1H), 8.65 (d, 1H), 9.15 (s, 1H). MS ESI (pos ion) for [M+H]⁺: 424 (calculated 423).

General Method for the Synthesis of Compounds (A10)

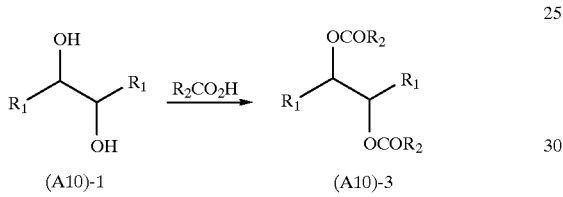

By allowing a compound of formula (A10)-1 prepared as above to react with a carboxylic acid (R₂CO₂H) wherein R₁ and R₂ are defined as above in formula (A10).

These reactions may be carried out in a solvent such as tetrahydrofuran (THF), dichloromethane (CH₂Cl₂), in the presence of diisopropyl carbodiimide (DIC) and a base (e.g. 4,4-dimethylaminopyridine) at temperatures ranging from 0° C. to 23° C., for 1 to 60 hours.

To 50 mg of diol 22 in 1 mL of dichloromethane was added diisopropyl carbodiimide (2.2 equiv) and the reaction was stirred for 1 hour at 23° C. To the solution was added 4,4-dimethylaminopyridine (0.2 equiv) followed by paramethoxybenzoic acid (2.2 equiv) in 5 mL of tetrahydrofuran and the mixture was stirred for an additional 3 hours at 23° C. The reaction was diluted with ethyl acetate and washed with 1N HCl, saturated sodium bicarbonate and the organic layer was dried over sodium sulfate. The crude mixture was purified using radial chromatography (ethyl acetate-hexane eluent). ¹H NMR of 161 (400 MHz, CDCl₃) δ 1.5 (s, 18H), 3.8 (s, 6H), 6.25 (d, 2H), 6.32 (s, 2H), 6.85 (d, 4H), 7.18 (d, 4H), 7.31 (d, 4H), 7.45 (d, 2H), 7.95 (d, 4H).

Examples

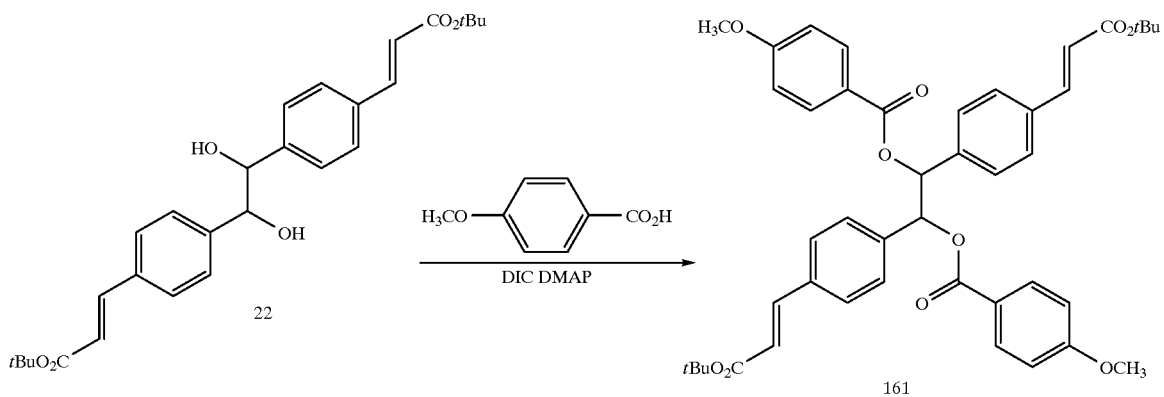

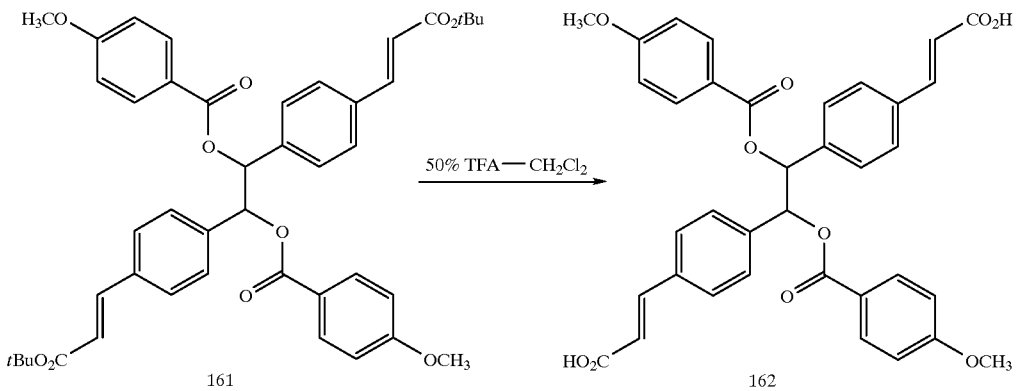

¹H NMR of 162 (400 MHz, CD₃OD) δ 3.8 (s, 6H), 6.4 (m, 4H), 6.95 (d, 4H), 7.38 (d, 4H), 7.5 (d, 4H), 7.6 (d, 2H), 7.95 (d, 4H). MS ESI (neg ion) for [M–H]⁻: 621 (calculated 622).

General Method for the Synthesis of Compounds (A11)

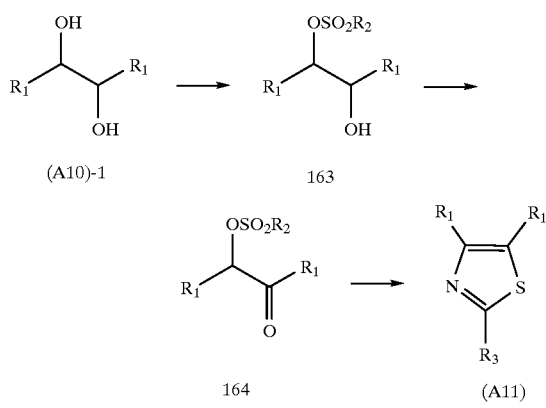

By allowing a compound of formula (A10)-1 prepared as above to react with a sulfonyl chloride ($R_2SO_2Cl$), and subsequently by oxidizing intermediate 163 and by allowing intermediate 164 to react with a thioamide ($R_3C(S)NH_2$) wherein $R_1$, $R_2$ and $R_3$ are defined as above in formula (A11).

The first step in this sequence of reactions may be carried out in a solvent such as tetrahydrofuran (THF), dichloromethane ($CH_2Cl_2$), in the presence of a base (e.g. 4,4-dimethylaminopyridine, triethylamine, triisopropylamine) and a sulfonyl chloride (e.g. tosyl chloride, mesyl chloride), at temperatures ranging from −20° C. to 23° C., for 1 to 60 hours. The second step in this sequence of reactions may be carried out in a solvent such as dichloromethane ($CH_2Cl_2$), in the presence of an oxidizing reagent (e.g. tetrapropylammonium perruthenate (VII) (TPAP)) and activated 4 Å molecular sieves at temperatures ranging from 0° C. to 23° C., for 1 to 60 hours. The third step in this sequence of reactions may be carried out in a solvent such as acetic acid, toluene, dioxane at temperatures ranging from 0° C. to 120° C., for 1 to 60 hours.

Examples

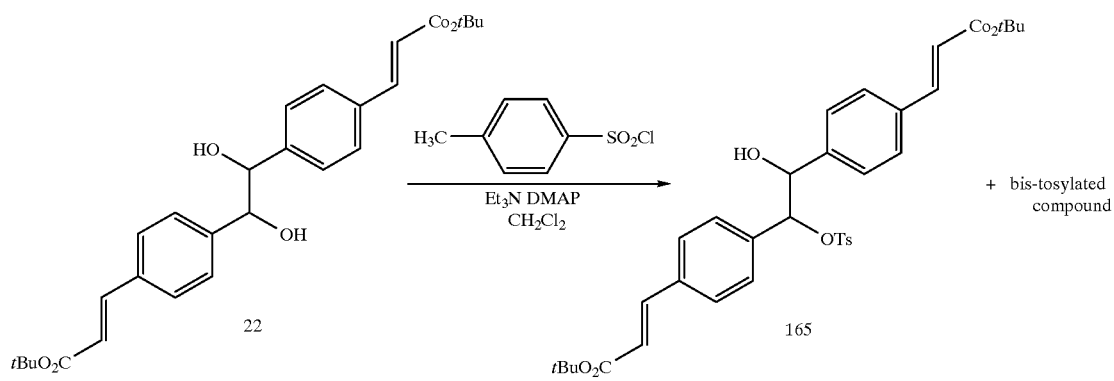

To 50 mg of diol 22 in 1 mL of dichloromethane was added Tosyl chloride (42.5 mg), 4,4-dimethylaminopyridine (6 mg), triethylamine (95 μl), and the reaction was stirred for 12 hours at 23° C. The volatiles were removed in vacuo and the crude mixture (containing 165, the bis-tosylated compound and the corresponding epoxide) was separated by flash chromatography (ethyl acetate-hexane eluent) to give a mixture of 165 and the corresponding bis-tosylated compound (27 mg total).

chromatography (ethyl acetate-hexane eluent) to give 3.9 mg of 166 and 16 mg of the corresponding bis-tosylate. $^1$H NMR of 166 (400 MHz, d$_6$-acetone) δ 1.5 (d, 18H), 2.4 (s, 3H), 6.4 (d, 1H), 6.5 (d, 1H), 6.95 (s, 1H), 7.35 (d, 2H), 7.42 (d, 2H), 7.5 (d, 1H), 7.6 (m, 3H), 7.7 (dd, 4H), 8 (d, 2H).

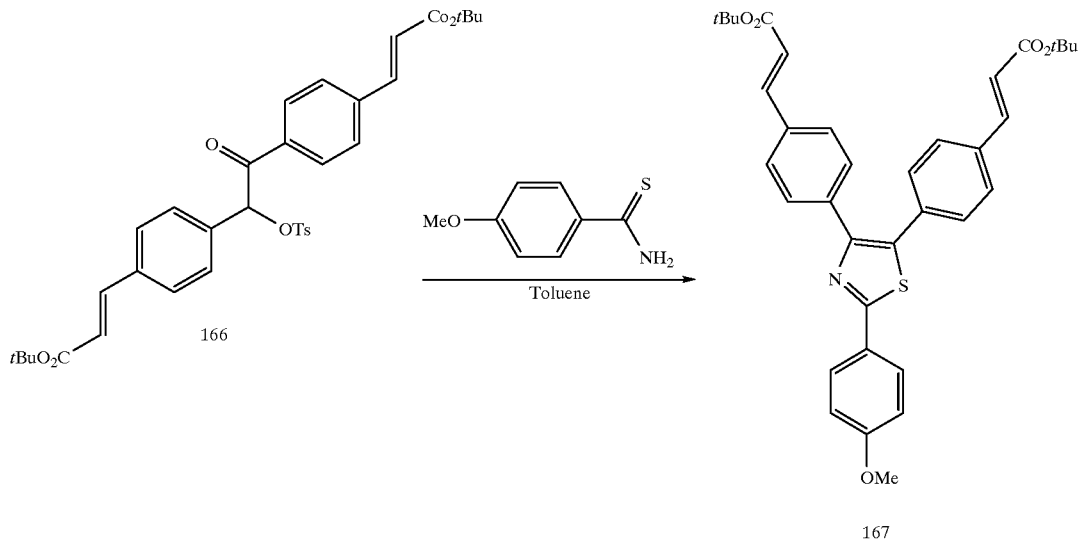

To 3.9 mg of 166 was added 3 mg of para-methoxythiobenzamide and 0.5 ml of toluene and the reaction was heated at 65° C. for 12 hours. The solvent was removed in vacuo and the crude mixture was purified by flash chromatography (ethyl acetate-hexane eluent) to give 1.8 mg of 167. $^1$NMR of 167 (400 MHz, CDCl$_3$) δ 1.5 (d, 18H), 3.8 (s, 3H), 6.3 (dd, 2H), 6.9 (d, 2H), 7.35 (d, 2H), 7.4 (m, 4H), 7.55 (m, 4H), 7.9 (d, 2H).

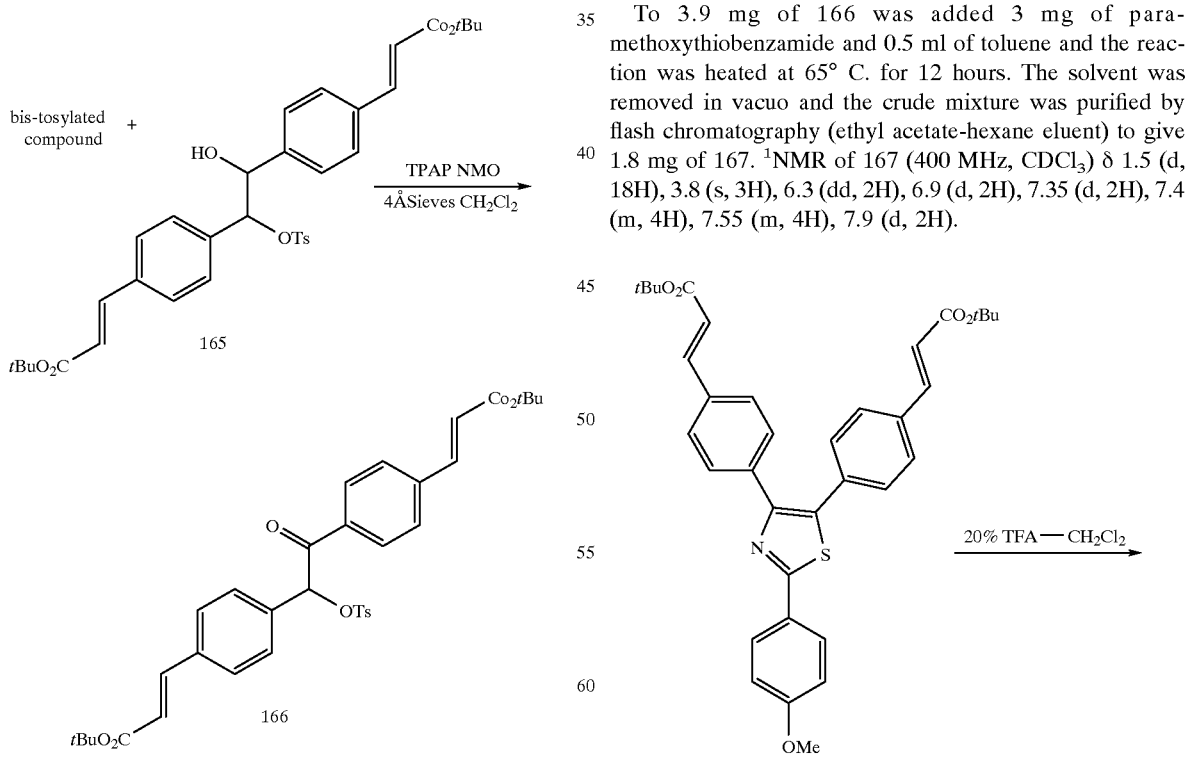

The mixture consisting of 165 and the corresponding bis-tosylated compound was oxidized as described above for compound 24. The crude mixture was purified by flash -continued

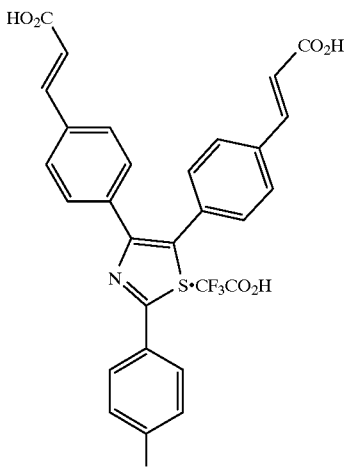

168

¹H NMR of 168 (400 MHz, CD₃OD) δ 3.8 (s, 3H), 6.45 (dd, 2H), 7.0 (d, 2H), 7.4 (d, 2H), 7.5–7.7 (m, 8H), 7.9 (d, 2H).

BIOLOGICAL PROTOCOLS

PTP-1B Gene Cloning and Protein Purification

The following procedure was conducted for recombinant production and purification of protein tyrosine phosphatase PTP-1B, for use as a substrate in PTPase inhibition assays.

A. Production of a PTP-1B cDNA

A human placental cDNA library was synthesized in a 50 ul reaction containing 1 ug human placental poly(A)⁺ mRNA (Clontech, Palo Alto, Calif.), 4 ul random hexamer primers, 8 ul of 10 mM dNTPs (Pharmacia, Piscataway N.J.), 1 ul (200 U/ul) Moloney murine leukemia virus reverse transcriptase (Gibco-BRL, Canada), 0.5 ul (26 U/ul) RNAsin™ which is a ribonuclease inhibitor (Promega, Madison Wis.), and 12 ul 5× buffer (Gibco-BRL). The synthesis reaction was incubated at 37° C. for one hour and then heat inactivated at 95° C. for five minutes.

A PTP-1B cDNA was amplified, using polymerase chain reaction (PCR), from the cDNAs synthesized as described above. More particularly, based on the published sequence of PTB-1B, two PCR primers were synthesized to amplify a portion of the PTP-1B coding sequence known to encode a 321 amino acid fragment containing the PTP-1B catalytic domain and having PTPase activity. See Hoppe et al., *Eur. J. Biochem.*, 223:1069–77 (1994); Barford, D., et al., *J. Molec. Biol.*, 239:726–730 (1994); Chernoff et al., *Proc. Natl. Acad. Sci. USA*, 87:2735–2739 (1990); Charbonneau et al. *Proc. Natl. Acad. Sci. USA*, 86:5252–5256 (1989). The primers had the following respective sequences:
PTP-1B-A(5') (SEQ ID NO: 1)
   5'CGCACTGGATCCTCATGGAGATGGAAAAGG 3'
PTP-1B-B(3') (SEQ ID NO: 2)
   5'CTCCCTGAATTCCTAATTGTGTGGCTCCAGG 3'
The first primer, which hybridizes to the non-coding strand, corresponds to the 5' portion of the PTP-1B coding sequence and encodes a BamH I restriction site upstream of the initiation codon, to facilitate cloning. The second primer, which hybridizes to the coding strand, corresponds to the 3' portion of the PTB-1B fragment of interest, and encodes a stop codon and an EcoR I restriction site downstream from the stop codon.

A 100 μl PCR reaction mixture containing approx. 1 ug of the human placental cDNA library, 0.2 mM of each dNTP, 30 uM of each primer, 1× Amplitaq DNA polymerase buffer (Perkin-Elmer, Norwalk Conn.), and 5 units Amplitaq DNA polymerase (Perkin-Elmer) was denatured at 94° C. for 5 minutes and then subjected to 25 cycles of amplification as follows: 1) 94° C. denaturation for 1 minute; 2) 55° C. annealing for 1 minute; and 3) 72° C. primer extension for 1 minute.

The PCR reaction product (992 bp) was digested with BamH I and EcoR I (New England Biolabs, Beverly Mass.) to yield a 975 bp product encoding the 321 amino acid PTP-1B protein fragment, and having "sticky ends" to facilitate cloning.

B. Production of a PTP-1B expression vector.

The 975 bp PTP-1B partial cDNA was purified by agarose gel electrophoresis and ligated into a BamH I/EcoR I-digested pGEX-3X plasmid vector (Pharmacia, Piscataway, N.J.). The pGEX vector is designed to produce a fusion of glutathione-S-transferase (GST) to a protein encoded by another DNA fragment inserted into the vector's cloning site. Complete sequencing of the insert of the resultant plasmid, designated pGEX-3X-PTP-1B, confirmed the identity of the PTP-1B cDNA, and insertion in the proper orientation and reading frame.

C. Expression and Purification of GST/PTP1B fusion protein.

*E. coli* strain DH5α (Gibco-BRL) was transformed with plasmid pGEX-3X-PTP-1B following the supplier's transformation protocol and grown at 37° C. with vigorous shaking in Luria-Bertani broth supplemented with 100 ug/ml ampicillin. When the cultures reached an O.D.$_{600}$ of 0.7–1, production of the GST/PTP-1B fusion protein was induced with 0.1 mM IPTG (Isopropyl b-D-Thiogalactoside). After 3 additional hours of culturing at 37° C., the bacteria were pelleted by centrifugation.

The bacterial pellet was resuspended in 10× (w/v) lysis buffer consisting of 12.5 mM HEPES, 2 mM EDTA, pH 7.0, 15 mM b-mercaptoethanol (bME) and 1 mM PMSF. The lysate was sonicated (on ice) until slight clearing was observed (approx. three min.) and then centrifuged at 10,000 revolutions per minute (RPM) for 10 min. The supernatant was diluted 1:4 with buffer A (25 mM HEPES, pH 7.0, and 15 mM bME).

Primary purification was achieved using a 5 ml Hi-Trap pre-packed Q column (Pharmacia). After loading the diluted supernatant onto the column, the column was washed with 10 bed volumes of buffer A. The GST/PTP-1B fusion protein was then eluted using a linear gradient of Buffer A and Buffer B (buffer A+1 M NaCl). Eluted fractions containing protein were identified by SDS-PAGE and Coomassie Blue staining (Pharmacia PhastSystem), and fractions containing PTP-1B activity were identified using the PTP-1B activity assay described below. Elution of the fusion protein occurred at about 30% Buffer B.

Fractions containing PTPase activity were pooled, diluted 1:4 with NET buffer (20 mM Tris, pH 8.8, 100 mM NaCl, 1 mM EDTA and 15 mM bME), and loaded onto a 10 ml GST-Sepharose 4B column (Pharmacia). After loading, the column was washed first with 3 bed volumes of NET buffer+1% NP40 (Sigma Chemical Co., St. Louis, Mo.), then with NET buffer until O.D. at 280 nm was basal. The GST/PTP-1B fusion protein was eluted from the column using 10 mM glutathione in 33 mM Tris, pH 8.0. Elution of proteins was monitored at O.D.$_{280}$ and fractions were assayed for activity and run on SDS-PAGE as described above. PTP-1B fusion protein eluted after approx. 4–5 minutes (flow rate 1 ml/min.).

The GST/PTP-1B-containing fractions from the GST-Sepharose 4B purification were pooled, concentrated into a final storage buffer (0.2 M NaCl, 25 mM HEPES, 1 mM EDTA, and 5 mM DTT, pH 7.0) using a 1 ml Hi-Trap Q column (pre-packed, Pharmacia), and stored at −80° C. (final concentration of 0.52 mg/ml). The foregoing procedure yielded approximately 5 mg of PTP-1B fusion protein per 500 ml of cultured cells, purified to substantial homogeneity as assessed by SDS-PAGE.

Assay of PTP-1B Activity

PTP-1B enzymatic activity of samples was assayed in microtiter plates as follows.

The protein concentration of the PTP-1B enzyme preparation was determined using the Bio-Rad Protein Assay kit (Bio-Rad, Hercules Calif.). An aliquot from each sample was taken and diluted to 2 mg protein/ml using activity assay buffer (100 mM Sodium Acetate, pH 6.0, 1 mM EDTA, 0.1% TX-100 (International Biotechnologies, Inc.) and 15 mM bME) to form a PTP-1B stock solution.

A 100 ul reaction mixture was prepared containing 10 ul of the PTP-1B stock solution, 10 ul of 9 mM p-nitrophenylphosphate ((pNPP), Sigma Chemical Co., St. Louis Mo.), and 80 ul of activity assay buffer (100 mM sodium acetate, pH 6.0, 1 mM EDTA, 0.1% Triton X-100, 15 mM bME). Reactions were mixed gently and incubated at 37° C. for 60 minutes. Enzymatic cleavage of phosphate from pNPP (a tyrosine phosphate analog) is marked by a colorimetric change in this substrate. See, e.g., Imbert et al., *Biochem J.*, 297:163–173 (1994); Ghosh and Miller, *Biochem. Biophys. Res. Comm.*, 194:36–44 (1993); Zanke et al., *Eur. J. Immunol.*, 22:235–39 (1992).

Reactions were stopped by addition of 10 ul of a 0.5 M NaOH/50% EtOH solution. To determine the enzymatic activity, absorbance readings of the reactions were measured at 405 nm using a Molecular Devices Thermomax Plate Reader (Menlo Park Calif.).

CD45 Gene Cloning and Protein Purification

The following procedure was conducted for recombinant production and purification of protein tyrosine phosphatase CD45, for use as a substrate in PTPase inhibition assays.

A. Production of a CD45 cDNA, and production of a CD45 expression vector.

A human cDNA library was synthesized from RNA isolated from the human Jurkat cell line, as described above for PTP-1B CD45 cDNA was amplified, using polymerase chain reaction (PCR), from the cDNAs synthesized above. Two PCR primers were synthesized to amplify the coding sequence of CD45. The primers had the following respective sequences:

CD45 (5') (SEQ ID NO: 3)
  5'CTACATCCCGGGATGTCCTGCAATTTAGATG3'
CD45 (3') (SEQ ID NO: 4)
  5'CATTTATGTCCCGGGCTATGAACCTTGAT3'

The first primer corresponds to the 5' portion of the CD45 coding sequence and encodes a Sma I restriction site upstream of the initiation codon, to facilitate cloning. The second primer corresponds to the 3' portion of the CD45 sequence, and encodes a stop codon and a Sma I restriction site downstream from the stop codon.

The PCR reaction product (2127 bp) was digested with Sma I (New England Biolabs, Beverly Mass.) to yield a 2110 bp product. The pET24C plasmid vector (Novagen, Inc., Madison Wis.) was digested with the BamH I restriction enzyme, and the "sticky" ends were filled using T4 DNA polymerase according to the manufacturer's instructions (New England Biolabs, Beverly Mass.); the resulting plasmid DNA was ligated to Sma I-digested CD45 PCR product. The pET24C vector is designed to produce high levels of the protein encoded by cDNA inserted into the vector's cloning site (CD45), in bacterial hosts. Complete sequencing of the insert of the resultant plasmid, designated pET24C-CD45, confirmed the identity of the CD45 cDNA, and insertion in the proper orientation and reading frame.

C. Expression and Purification of CD45 protein.

*E. coli* strain DH5α (Gibco-BRL) was transformed with pET24C-CD45 following the supplier's transformation protocol, plated onto Luria-Bertani agar plates supplemented with 30 ug/ml kanamycin and grown overnight at 37° C. A single 30 bacterial colony was transferred into 50 mls Luria-Bertani broth supplemented with 30 ug/ml kanamycin and grown overnight with vigorous shaking. This overnight culture was split into two equal parts, and added to 2L Luria-Bertani broth supplemented with 50 ug/ml kanamycin. When the cultures reached an $O.D._{600}$ of 1, production of the recombinant CD45 protein was induced with 0.1 mM IPTG (Isopropyl b-D-Thiogalactoside). After 5 additional hours of culturing at 37° C., the bacteria were pelleted by centrifugation.

The bacterial pellet (approximately 5 grams) was resuspended in 10× (w/v) lysis buffer consisting of 12.5 mM HEPES, 2 mM EDTA, pH 7.0, 15 mM bME and 1 mM PMSF. The lysate was sonicated (on ice) until slight clearing was observed (approx. three min.) and then centrifuged at 10,000 revolutions per minute (RPM) for 10 min. The supernatant was filtered through 1 mm Wattman filter paper, and 9.7 grams (i.e., 194 grams/L) of ammonium sulfate were added to the solution on ice to precipitate soluble proteins. After a 1 hour incubation on ice, the lysate was spun at 10,000 RPM for 30 min. at 4 C.; supernatant was removed, and an additional 7.6 grams (i.e., 151 grams/L) of ammonium sulfate were added. The resulting pellet was resuspended in 3 mls of buffer B (33 mM imidazole-HCl pH 8.0, 2mM EDTA, 10 mM bME, 0.002% PMSF) and stored on ice. After another 1 hour incubation on ice, the spin supernatant with ammonium sulfate was spun again at 10,000 RPM for 30 mins at 4 C. The resulting pellet from the second centrifugation was resuspended in 2 mls of buffer B. The two pellet solutions were pooled and dialyzed overnight against buffer B.

Secondary purification was achieved using a Mono-Q column. (Pharmacia). After loading the diluted supernatant onto the column, the column was washed with 10 bed volumes of buffer B. The recombinant CD45 protein was then eluted using a linear gradient of Buffer B and Buffer C (buffer B+1 M NaCl). Eluted fractions containing protein were identified by SDS-PAGE and Coomassie Blue staining (Pharmacia PhastSystem), and fractions containing CD45 activity were identified using the CD45 activity assay described below.

The CD45-containing fractions from the MonoQ column purification were pooled and stored at 4 C.

Assay of CD45 Activity

CD45 enzymatic activity of samples was assayed in microtiter plates as follows.

A 100 ul reaction mixture was prepared containing 10 ul of the CD45 stock solution, 10 ul of 9.3 mM p-nitrophenylphosphate ((pNPP), Sigma Chemical Co., St. Louis Mo.), and 80 ul of activity assay buffer (100 mM sodium acetate, pH 6.0, 1 mM EDTA, 0.1% Triton X-100, 15 mM bME). Reactions were mixed gently and incubated at 37° C. for 60 minutes. Reactions were stopped by addition of 10 ul of a 0.5 M NaOH/50% EtOH solution. To determine the enzymatic activity, absorbance readings of the reactions were measured at 405 nm using a Molecular Devices Thermomax Plate Reader (Menlo Park Calif.).

In vitro PTPase Inhibition Assay

The ability of the compounds of the present invention, such as the cinnamic acid derivative compounds of Example 2, to inhibit the PTPase activity of PTP-1B, CD45, PTP-1C, and PTPα was determined using modifications of the PTP-1B and CD45 activity assays described in Examples 3 and 4.

First, 0.001 mmol of the cinnamic acid derivative (or other PTPase inhibitor compound) was dissolved in 100 ul of DMSO to create a 10 mM stock solution. The 10 mM stock solution was used to add varying concentrations (100 uM, 33 uM, 10 uM, 3 uM, 1 uM, 0.3 uM, 0.1 uM, 0.03 uM, 0.01 uM or 0.003 uM) of the inhibitor compound to a series of otherwise identical PTPase activity assay reactions (100 ul final volume in microtiter wells). Thus, each 100 ul reaction contained 10 ul PTPase enzyme stock solution (final phosphatase concentration of approximately 20 ng/well), 70 ul activity assay buffer, 10 ul pNPP stock solution (final pNPP concentration of 0.9 mM for PTP-1B assay, 0.93 mM for CD45 assay, 0.5 mM for PTPα assay, and 8 mM for PTP-1C assay), and 10 ul of the diluted inhibitor compound in DMSO. Assay buffers contained: for CD45 and PTP-1B assays, 100 mM sodium acetate at pH 6.0, 1 mM EDTA, 0.1% Triton X-100, and 15 mM bME; for PTP-1C assays, 100 mM sodium acetate at pH 5.5, 0.1% BSA, and 15 mM bME; for PTPα assays, 100 mM sodium acetate at pH 5.25, 0.1% BSA, and 15 mM bME. Purified phosphatase was added to the reaction mixtures to begin the reactions; the reactions were incubated at 37 C. for 60 min. (for PTP-1B and CD45 assays) or at 27 C. for 60 min. (for PTP-1C and PTPα assays), stopped, and colorimetrically analyzed as described above. As positive and negative controls, reactions were performed containing 10 ul DMSO with no inhibitor compound or containing the known PTPase inhibitors vanadate (final concentration 0.5 mM; for PTP-1B and CD45 assays) or ammonium molybdate (final concentration 1 mM; for PTP-1C and PTPα assays) substituted for the inhibitor compound of the invention.

The concentration of inhibitor compound required to inhibit 50% of the PTPase activity (IC50) was determined as follows. First, absorbance readings from the negative control reactions were treated as a baseline and subtracted from the absorbance readings of the experimental reactions. Then, for each reaction, a percent inhibition was calculated using the following formula:

100×[1−(O.D.$_{405}$ reaction/O.D.$_{405}$ DMSO)]

For each inhibitor compound tested, an IC50 concentration was calculated from a best-fit computer analysis of the calculated percent inhibition for the various dilutions of the compound.

Inhibitor compounds having an IC50 less than 10 uM (and optimally less than 5 uM) for a particular PTPase were scored as highly effective inhibitors of that PTPase enzyme, and are preferred inhibitors of the present invention.

As it will be apparent to those persons skilled in the art, the foregoing biological data is not absolute and will vary according to many factors such as assay condition and the like.

TABLE 8

| Compound | % inhibition of PTP1B at 1 μM | % inhibition of PTPα at 100 μM | % inhibition of PTP1C at 100 μM |
|---|---|---|---|
| 36 | 52 | 0 | 42 |
| 37 | 85 | 63 | 59 |
| 38 | 93 | 71 | 63 |
| 39 | 82 | 47 | 53 |
| 40 | 88 | 82 | 62 |
| 41 | 39 | 20 | 17 |
| 42 | 84 | 92 | 88 |
| 43 | 76 | 82 | 79 |
| 44 | 79 | 87 | 86 |
| 45 | 85 | 85 | 84 |
| 46 | 75 | 73 | 61 |
| 47 | 68 | 48 | 63 |
| 48 | 69 | 3 | 33 |
| 49 | 37 | 0 | 35 |
| 50 | 50 | 37 | 25 |

TABLE 9

IC50 values (in μM) against PTP1B and CD45 for given compounds

| | PTP1B | CD45 | | PTP1B | CD45 | | PTP1B | CD45 |
|---|---|---|---|---|---|---|---|---|
| 9 | 0.37 | 3.9 | 70 | 0.42 | 1.9 | 95 | 2 | 6 |
| 13 | 31 | —* | 71 | 0.43 | 0.53 | 96 | 0.4 | 2.4 |
| 23 | 0.27 | —* | 72 | 0.52 | 5.5 | 97 | 6 | 10 |
| 25 | 0.89 | —* | 73 | 0.62 | 2.8 | 98 | 6 | 10 |
| 27 | 0.5 | —* | 74 | 0.64 | 4.2 | 99 | 1.5 | 7.4 |
| 29 | 0.8 | —* | 75 | 0.68 | 3.4 | 100 | 26 | >100 |
| 32 | 1.8 | —* | 76 | 0.68 | 0.93 | 133 | | —* |
| 54 | 0.072 | 0.73 | 77 | 0.78 | 7.5 | 134 | 3.4 | 20 |
| 55 | 0.1 | 0.56 | 78 | 0.79 | 1.15 | 136 | 0.7 | 8 |
| 56 | 0.135 | 0.94 | 79 | 4.8 | 8.2 | 140 | 1.2 | 20 |
| 57 | 0.25 | 1.0 | 80 | 10 | 20 | 144 | 3 | —* |
| 58 | 0.25 | 0.97 | 81 | 26 | 19 | 146 | 5.9 | —* |
| 59 | 0.25 | 0.35 | 82 | 11.9 | 12.8 | 148 | 9 | —* |
| 60 | 0.29 | 1.0 | 83 | 1.3 | 1.5 | 152 | 0.85 | 1.2 |
| 61 | 0.97 | 0.955 | 84 | 1.2 | 2.7 | 153 | 2.65 | 1.91 |
| 62 | 1.5 | 0.985 | 85 | 1.5 | 1.8 | 154 | 3.83 | 2.45 |
| 63 | 1.7 | 2.4 | 86 | 1.8 | 7.1 | 155 | 1 | 1.3 |
| 64 | 3.0 | 6.4 | 87 | 1.0 | 1.1 | 156 | 1.7 | 1.3 |
| 65 | 1.3 | 1.4 | 88 | 2.65 | 7.8 | 157 | 5.5 | 1.5 |
| 66 | 1.7 | 2.5 | 89 | 13.7 | >100 | 160 | 0.98 | 1.52 |
| 67 | 1.0 | 1.25 | 90 | 0.86 | 1.12 | 162 | 1.8 | —* |
| 68 | 0.3 | 0.865 | 91 | 25.9 | >100 | 168 | 3 | —* |
| 69 | 0.41 | 1.9 | 94 | 0.7 | 7 | | | |

—*: data not available

TABLE 10

| Compound | % inhibition of PTP1B at 1 μM | % inhibition of CD45 at 1 μM |
|---|---|---|
| 103 | 44% | 14% |
| 104 | 24% | 14% |
| 105 | 61% | 18% |
| 106 | 45% | 21% |
| 107 | 25% | 51% |
| 108 | 30% | 62% |
| 109 | —* | 14% |
| 110 | —* | 22% |
| 111 | —* | 18% |
| 112 | —* | 16% |
| 113 | —* | 61% |

—*: data not available

TABLE 11

| Compound | % inhibition of PTP1B at 1 μM | Compound | % inhibition of PTP1B at 1 μM |
|---|---|---|---|
| 116 | 41% | 123 | 85% |
| 117 | 67% | 124 | 83% |
| 118 | 56% | 125 | 93% |
| 119 | 71% | 126 | 59% |
| 120 | 67% | 127 | 79% |
| 121 | 73% | 128 | 80% |
| 122 | 87% | | |

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of Formula (A1) thru (A11) where a basic or acidic group is present in the structure, are also included within the scope of this invention. When an acidic substituent is present, such as —COOH, there can be formed the ammonium, sodium, potassium, calcium salt, and the like, for use as the dosage form. When a basic group is present, such as amino or a basic heteroaryl radical, such as pyridyl, an acidic salt, such as hydrochloride, hydrobromide, acetate, maleate, pamoate, methanesulfonate, p-toluenesulfonate, and the like, can be used as the dosage form.

Also, in the case of the —COOH being present, pharmaceutically acceptable esters can be employed, e.g., methyl, tert-butyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

The term "therapeutically effective amount" shall mean that amount of drug or pharmaceutical agent that will elicit the biological or medical response of a tissue, system, animal, or human that is being sought by a researcher, veterinarian, medical doctor or other clinician. Generally, a daily dose of about 0.5 mg/Kg to 100 mg/Kg body weight in divided doses is suggested to treat PTPase related diseases. Such dosage has to be individualized by the clinician.

The present invention also has the objective of providing suitable topical, oral, and parenteral pharmaceutical formulations for use in the novel methods of treatment of the present invention. The compounds of the present invention may be administered orally as tablets, aqueous or oily suspensions, lozenges, troches, powders, granules, emulsions, capsules, syrups or elixirs. The composition for oral use may contain one or more agents selected from the group of sweetening agents, flavouring agents, colouring agents and preserving agents in order to produce pharmaceutically elegant and palatable preparations. The tablets contain the acting ingredient in admixture with non-toxic pharmaceutically acceptable excipients which are suitable for the manufacture of tablets. These excipients may be, for example, (1) inert diluents, such as calcium carbonate, lactose, calcium phosphate or sodium phosphate; (2) granulating and disintegrating agents, such as corn starch or alginic acid; (3) binding agents, such as starch, gelatin or acacia; and (4) lubricating agents, such as magnesium stearate, stearic acid or talc. These tablets may be uncoated or coated by known techniques to delay disintegration and absorption in the gastrointestinal tract and thereby provide a sustained action over a longer period. For example, a time delay material such as glyceryl monostearate or glyceryl distearate may be employed. Coating may also be performed using techniques described in the U.S. Pat. Nos. 4,256,108; 4,160,452; and 4,265,874 to form osmotic therapeutic tablets for control release.

Formulations for oral use may be in the form of hard gelatin capsules wherein the active ingredient is mixed with an inert solid diluent, for example, calcium carbonate, calcium phosphate or kaolin. They may also be in the form of soft gelatin capsules wherein the active ingredient is mixed with water or an oil medium, such as peanut oil, liquid paraffin or olive oil.

Aqueous suspensions normally contain the active materials in admixture with excipients suitable for the manufacture of aqueous suspension. Such expicients may be: (1) suspending agent such as sodium carboxymethyl cellulose, methyl cellulose, hydroxypropylmethylcellulose, sodium alginate, polyvinylpyrrolidone, gum tragacanth and gum acacia;

(2) dispersing or wetting agents which may be (a) naturally occurring phosphatide such as lecithin; (b) a condensation product of an alkylene oxide with a fatty acid, for example, polyoxyethylene stearate; (c) a condensation product of ethylene oxide with a long chain aliphatic alcohol, for example, heptadecaethylenoxycetanol; (d) a condensation product of ethylene oxide with a partial ester derived from a fatty acid and hexitol such as polyoxyethylene sorbitol monooleate, or (e) a condensation product of ethylene oxide with a partial ester derived from fatty acids and hexitol anhydrides, for example polyoxyethylene sorbitan monooleate.

The pharmaceutical compositions may be in the form of a sterile injectable aqueous or oleagenous suspension. This suspension may be formulated according to known methods using those suitable dispersing or wetting agents and suspending agents which have been mentioned above. The sterile injectable preparation may also a sterile injectable solution or suspension in a non-toxic parenterally-acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed including synthetic mono- or diglycerides. In addition, fatty acids such as oleic acid find use in the preparation of injectables.

Compounds of Formula (A1) thru (A11) may also be administered in the form of suppositories for rectal administration of the drug. These compositions can be prepared by mixing the drug with a suitable non-irritating excipient which is solid at ordinary temperature but liquid at the rectal temperature and will therefore melt in the rectum to release the drug. Such materials are cocoa butter and polyethylene glycols.

The compounds of the present invention may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

For topical use, creams, ointments, jellies, solutions or suspensions, etc., containing the compounds of Formula (A1) thru (A11) are employed.

What is claimed is:
1. A compound with the structure depicted in Formula (A8):

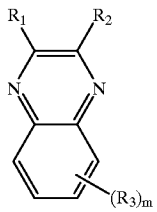
(A8)

wherein at least one of $R_1$ and $R_2$ substituents has the general structure depicted in Formula (B)

X—C(R')=C(R")COOR''' (B)

wherein
(i) R' and R" are independently selected from the group consisting of
hydrogen, halo, cyano, nitro, trihalomethyl, $C_{1-11}$alkyl, optionally substituted aryl$C_{1-11}$alkyl wherein the aryl substituents are independently selected from the group consisting of hydrogen, halo, nitro, cyano, trihalomethyl, hydroxypyronyl, $C_{1-11}$alkyl, aryl$C_{1-11}$alkyl, $C_{0-11}$alkyloxy$C_{0-11}$alkyl, aryl$C_{0-11}$alkyloxy$C_{0-11}$alkyl, $C_{0-11}$alkylthio$C_{0-11}$alkyl, aryl$C_{0-11}$alkylthio$C_{0-11}$alkyl, $C_{0-11}$alkylamino$C_{0-11}$alkyl, aryl$C_{0-11}$alkylamino$C_{0-11}$alkyl, di(aryl$C_{1-11}$alkyl)amino$C_{0-11}$alkyl, $C_{1-11}$alkylcarbonyl$C_{0-11}$alkyl, aryl$C_{1-11}$alkylcarbonyl$C_{0-11}$alkyl, $C_{1-11}$alkylcarboxy$C_{0-11}$alkyl, aryl$C_{1-11}$alkylcarboxy$C_{0-11}$alkyl, $C_{1-11}$alkylcarbonylamino$C_{0-11}$alkyl, aryl$C_{1-11}$alkylcarbonylamino$C_{0-11}$alkyl, —$C_{0-11}$alkylCOOR$_4$, —$C_{0-11}$alkylCONR$_5$R$_6$ wherein $R_4$, $R_5$ and $R_6$ are independently selected from hydrogen, $C_1$–$C_{11}$alkyl, aryl$C_0$–$C_{11}$alkyl, or $R_5$ and $R_6$ are taken together with the nitrogen to which they are attached forming a cyclic system containing 3 to 8 carbon atoms with at least one $C_1$–$C_{11}$alkyl, aryl$C_0$–$C_{11}$alkyl substituent.
(ii) R''' is selected from the group consisting of
(a) hydrogen,
(b) $C_{1-11}$alkyl, substituted $C_{1-11}$alkyl wherein the substituents are independently selected from halo, cyano, nitro, trihalomethyl, carbamoyl, tetrahydrofuryl, pyrrolidinyl, piperidinyl, morpholinyl, piperazinyl, hydroxypyronyl, $C_{0-11}$alkyloxy, aryl$C_{0-11}$alkyloxy, $C_{0-11}$alkylthio, aryl$C_{0-11}$alkylthio, $C_{0-11}$alkylamino, aryl$C_{0-11}$alkylamino, di(aryl$C_{0-11}$alkyl)amino, $C_{1-11}$alkylcarbonyl, aryl$C_{1-11}$alkylcarbonyl, $_{1-11}$alkylcarboxy, aryl$C_{1-11}$alkylcarboxy, $C_{1-11}$alkylcarbonylamino, aryl $C_{1-11}$alkylcarbonylamino, —$C_{0-11}$alkylCOOR$_7$, —$C_{0-11}$alkylCONR$_8$R$_9$ wherein $R_7$, $R_8$ and $R_9$ are independently selected from hydrogen, $C_1$–$C_{11}$alkyl, aryl$C_0$–$C_{11}$alkyl, or $R_8$ and $R_9$ are taken together with the nitrogen to which they are attached forming a cyclic system containing 3 to 8 carbon atoms with at least one $C_1$–$C_{11}$alkyl, aryl$C_0$–$C_{11}$alkyl substituent,
(c) mono-, di- and tri-substituted aryl$C_0$–$C_{11}$alkyl wherein the aryl substituents are defined as above for R' and R",
(iii) X is a mono-, di- or trisubstituted aryl wherein the aryl substituents are defined as above for R' and R", and aryl is selected from phenyl, biphenyl, naphthyl, dihydronaphthyl, tetrahydronaphthyl, indenyl, indanyl, azulenyl, anthryl, phenanthryl, fluorenyl, pyrenyl, thienyl, benzothienyl, isobenzothienyl, 2,3-dihydrobenzothienyl, furyl, pyranyl, benzofuranyl, isobenzofuranyl, 2,3-dihydrobenzofuranyl, pyrrolyl, indolyl, isoindolyl, indolizinyl, indazolyl, imidazolyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, hydroxypyronyl, pyrazolyl, triazolyl, tetrazolyl, thiazolyl, isothiazolyl, benzthiazolyl, oxazolyl, isoxazolyl, benzoxazolyl, oxadiazolyl, or thiadiazolyl, and wherein the remaining of $R_1$ and $R_2$ is independently selected from the group consisting of:
(i) hydrogen;
(ii) $C_{1-11}$alkyl, substituted $C_{1-11}$alkyl wherein the alkyl substituents are defined as above,
(iii) aryl$C_{0-11}$alkyl,
(iv) mono-, di- and tri-substituted aryl$C_0$–$C_{11}$alkyl wherein the aryl substituents are defined as above,
and wherein m is an integer between 0 and 4 and each $R_3$ is independently selected from the group consisting of hydrogen, halo, nitro, cyano, trihalomethyl, hydroxypyronyl, $C_{1-11}$alkyl, $C_{0-11}$alkyloxy$C_{0-11}$alkyl, aryl$C_{0-11}$alkyloxy$C_{0-11}$alkyl, $C_{0-11}$alkylthio$C_{0-11}$alkyl, aryl$C_{0-11}$alkylthio$C_{1-11}$alkyl, $C_{0-11}$alkylamino$C_{0-11}$alkyl, aryl$C_{0-11}$alkylamino$C_{0-11}$alkyl, di(aryl$C_{1-11}$alkyl)amino$C_{0-11}$alkyl, $C_{1-11}$alkylcarbonyl$C_{0-11}$alkyl, $C_{1-11}$alkylcarboxy$C_{0-11}$alkyl, $C_{1-11}$alkylcarbonylamino$C_{0-11}$alkyl, aryl$C_{1-11}$alkylcarbonyl$C_{0-11}$alkyl, aryl$C_{1-11}$alkylcarboxy$C_{0-11}$alkyl, aryl$C_{1-11}$alkylcarbonylamino$C_{0-11}$alkyl, —CH=CHCOOR$_{10}$, —CH=CHCONR$_{11}$R$_{12}$, —$C_{0-11}$alkylCOOR$_{13}$, —$C_{0-11}$alkylCONR$_{14}$R$_{15}$ wherein $R_{10}$ thru $R_{15}$ are independently selected from hydrogen, $C_1$–$C_{11}$alkyl, aryl$C_0$–$C_{11}$alkyl, or $R_{11}$ and $R_{12}$ are taken together with the nitrogen to which they are attached forming a cyclic system containing 3 to 8 carbon atoms with at least one $C_1$–$C_{11}$alkyl, aryl$C_0$–$C_{11}$alkyl substituent, or $R_{14}$ and $R_{15}$ are taken together with the nitrogen to which they are attached forming a cyclic system containing 3 to 8 carbon atoms with at least one $C_1$–$C_{11}$alkyl, aryl$C_0$–$C_{11}$alkyl substituent,
or its pharmaceutically acceptable salts, or esters, thereof.

2. A compound as defined in claim 1 wherein aryl is selected from phenyl, naphthyl, biphenyl, thienyl, furyl, pyridyl, or its pharmaceutically acceptable salts, or esters, thereof.

3. A compound as defined in claim 1 wherein aryl is phenyl, or its pharmaceutically acceptable salts, or esters, thereof.

4. A compound as defined in claim 1 wherein aryl is naphthyl, or its pharmaceutically acceptable salts, or esters, thereof.

5. A compound as defined in claim 1 wherein aryl is biphenyl, or its pharmaceutically acceptable salts, or esters, thereof.

6. A compound as defined in claim 1 wherein aryl is thienyl, or its pharmaceutically acceptable salts, or esters, thereof.

7. A compound as defined in claim 1 wherein aryl is furyl, or its pharmaceutically acceptable salts, or esters, thereof.

8. A compound as defined in claim 1 wherein aryl is pyridyl, or its pharmaceutically acceptable salts, or esters, thereof.

9. A compound with the structure depicted in Formula (A8):

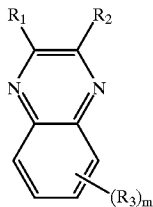

(A8)

wherein $R_1$ is selected from $-COR_{16}$, $-COOR_{17}$, $-CONR_{18}R_{19}$ wherein $R_{16}$ thru $R_{19}$ are independently selected from hydrogen, $C_1-C_{11}$alkyl, substituted $C_{1-11}$alkyl where the alkyl substituents are as defined below, optionally substituted aryl$C_0C_{11}$alkyl where the aryl substituents are as defined below, or $R_{18}$ and $R_{19}$ are taken together with the nitrogen to which they are attached forming a cyclic system containing 3 to 8 carbon atoms with at least one $C_1-C_{11}$alkyl, aryl$C_0-C_{11}$alkyl substituent, and wherein $R_2$ has the general structure depicted in Formula (B)

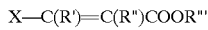

$X-C(R')=C(R'')COOR'''$ (B)

wherein (i) R' and R" are independently selected from the group consisting of
hydrogen, halo, cyano, nitro, trihalomethyl, $C_{1-11}$alkyl, optionally substituted aryl$C_{1-11}$alkyl wherein the aryl substituents are independently selected from the group consisting of hydrogen, halo, nitro, cyano, trihalomethyl, hydroxypyronyl, $C_{1-11}$alkyl, aryl$C_{1-11}$alkyl, $C_{0-11}$alkyloxy$C_{0-11}$alkyl, aryl$C_{0-11}$alkyloxy$C_{0-11}$alkyl, $C_{0-11}$alkylthio$C_{0-11}$alkyl, aryl$C_{0-11}$alkylthio$C_{0-11}$alkyl, $C_{0-11}$alkylamino$C_{0-11}$alkyl, aryl$C_{0-11}$alkylamino$C_{0-11}$alkyl, di(aryl$C_{1-11}$alkyl)amino$C_{0-11}$alkyl, $C_{1-11}$alkylcarbonyl$C_{0-11}$alkyl, aryl$C_{1-11}$alkyl, $C_{1-11}$alkylcarboxy$C_{0-11}$alkyl, aryl$C_{1-11}$alkylcarboxy$C_{0-11}$alkyl, $C_{1-11}$alkylcarbonylamino$C_{0-11}$alkyl, aryl$C_{1-11}$alkylcarbonylamino$C_{0-11}$alkyl, $-C_{0-11}$alkylCOOR$_4$, $-C_{0-11}$alkylCONR$_5R_6$ wherein $R_4$, $R_5$ and $R_6$ are independently selected from hydrogen, $C_1-C_{11}$alkyl, aryl$C_0-C_{11}$alkyl, or $R_5$ and $R_6$ are taken together with the nitrogen to which they are attached forming a cyclic system containing 3 to 8 carbon atoms with at least one $C_1-C_{11}$alkyl, aryl$C_0-C_{11}$alkyl substituent.

(ii) R''' is selected from the group consisting of
(a) hydrogen,
(b) $C_{1-11}$alkyl, substituted $C_{1-11}$alkyl wherein the substituents are independently selected from halo, cyano, nitro, trihalomethyl, carbamoyl, tetrahydrofuryl, pyrrolidinyl, piperidinyl, morpholinyl, piperazinyl, hydroxypyronyl, $C_{0-11}$alkyloxy, aryl$C_{0-11}$alkyloxy, $C_{0-11}$alkylthio, aryl$C_{0-11}$alkylthio, $C_{0-11}$alkylamino, aryl$C_{0-11}$alkylamino, di(aryl$C_{0-11}$alkyl)amino, $C_{1-11}$alkylcarbonyl, aryl$C_{1-11}$alkylcarbonyl, $C_{1-11}$alkylcarboxy, aryl$C_{1-11}$alkylcarboxy, $C_{1-11}$alkylcarbonylamino, aryl$C_{1-11}$alkylcarbonylamino, $-C_{0-11}$alkylCOOR$_7$, $-C_{0-11}$alkylCONR$_8R_9$ wherein $R_7$, $R_8$ and $R_9$ are independently selected from hydrogen, $C_1-C_{11}$alkyl, aryl$C_0-C_{11}$alkyl, or $R_8$ and $R_9$ are taken together with the nitrogen to which they are attached forming a cyclic system containing 3 to 8 carbon atoms with at least one $C_1-C_{11}$alkyl, aryl$C_0-C_{11}$alkyl substituent,
(c) mono-, di- and tri-substituted aryl$C_0-C_{11}$alkyl wherein the aryl substituents are defined as above for R' and R'',
(iii) X is a mono-, di- or trisubstituted aryl wherein the aryl substituents are defined as above for R' and R'', and aryl is selected from phenyl, biphenyl, naphthyl, dihydronaphthyl, tetrahydronaphthyl, indenyl, indanyl, azulenyl, anthryl, phenanthryl, fluorenyl, pyrenyl, thienyl, benzothienyl, isobenzothienyl, 2,3-dihydrobenzothienyl, furyl, pyranyl, benzofuranyl, isobenzothienyl, 2,3-dihydrobenzofuranyl, pyrrolyl, indolyl, isoindolyl, indolizinyl, indazolyl, imidazolyl, benzimidazolyl, pyridyl, pyrazinyl, pyradazinyl, pyrimidinyl, triazinyl, quinolyl, isoquinolyl, 4H-quinolizinyl, cinnolinyl, phthalazinyl, quinazolinyl, quinoxalinyl, 1,8-naphthyridinyl, pteridinyl, carbazolyl, acridinyl, phenazinyl, phenothiazinyl, phenoxazinyl, chromanyl, benzodioxolyl, piperonyl, purinyl, hydroxypyronyl, pyrazolyl, triazolyl, tetrazolyl, thiazolyl, isothiazolyl, benzthiazolyl, oxazolyl, isoxazolyl, benzoxazolyl, oxadiazolyl, or thiadiazolyl, and wherein $R_2$ is selected from the group consisting of:
(i) hydrogen;
(ii) $C_{1-11}$alkyl, substituted $C_{1-11}$alkyl wherein the alkyl substituents are defined as above, (iii) aryl$C_{0-11}$alkyl, (iv) mono-, di- and tri-substituted aryl$C_0-C_{11}$alkyl wherein the aryl substituents are defined as above, and wherein m is an integer between 0 and 4 and each $R_3$ is independently selected from the group consisting of hydrogen, halo, nitro, cyano, trihalomethyl, hydroxypyronyl, $C_{1-11}$alkyl, $C_{0-11}$alkyloxy$C_{0-11}$alkyl, aryl$C_{0-11}$alkyloxy$C_{0-11}$alkyl, $C_{0-11}$alkylthio$C_{0-11}$alkyl, aryl$C_{0-11}$alkylthio$C_{0-11}$alkyl, $C_{0-11}$alkylamino$C_{0-11}$alkyl, aryl$C_{0-11}$alkylamino$C_{0-11}$alkyl, di(aryl$C_{1-11}$alkyl)amino$C_{0-11}$alkyl, $C_{1-11}$alkylcarbonyl$C_{0-11}$alkyl, $C_{1-11}$alkylcarboxy$C_{0-11}$alkyl, $C_{1-11}$alkylcarbonylamino$C_{0-11}$alkyl, aryl$C_{1-11}$alkylcarbonyl$C_{0-11}$alkyl, aryl$C_{1-11}$alkylcarboxy$C_{0-11}$alkyl, aryl$C_{1-11}$alkylcarbonylamino$C_{0-11}$alkyl, $-CH=CHCOOR_{10}$, $-CH=CHCONR_{11}R_{12}$, $-C_{0-11}$alkylCOOR$_{13}$, $-C_{0-11}$alkylCONR$_{14}R_{15}$ wherein $R_{10}$ thru $R_{15}$ are independently selected from hydrogen, $C_1-C_{11}$alkyl, aryl$C_0-C_{11}$alkyl, or $R_{11}$ and $R_{12}$ are taken together with the nitrogen to which they are attached forming a cyclic system containing 3 to 8 carbon atoms with at least one $C_1-C_{11}$alkyl, aryl$C_0-C_{11}$alkyl substituent, or $R_{14}$ and $R_{15}$ are taken together with the nitrogen to which they are attached forming a cyclic system containing 3 to 8 carbon atoms with at least one $C_1-C_{11}$alkyl, aryl$C_0-C_{11}$alkyl substituent,
or its pharmaceutically acceptable salts, or esters, thereof.

10. A compound as defined in claim 9 wherein aryl is selected from phenyl, naphthyl, biphenyl, thienyl, furyl, pyridyl, or its pharmaceutically acceptable salts, or esters, thereof.

11. A compound as defined in claim 9 wherein aryl is phenyl, or its pharmaceutically acceptable salts, or esters, thereof.

12. A compound as defined in claim 9 wherein aryl is naphthyl, or its pharmaceutically acceptable salts, or esters, thereof.

13. A compound as defined in claim 9 wherein aryl is biphenyl, or its pharmaceutically acceptable salts, or esters, thereof.

14. A compound as defined in claim 9 wherein aryl is thienyl, or its pharmaceutically acceptable salts, or esters, thereof.

15. A compound as defined in claim 9 wherein aryl is furyl, or its pharmaceutically acceptable salts, or esters, thereof.

16. A compound as defined in claim 9 wherein aryl is pyridyl, or its pharmaceutically acceptable salts, or esters, thereof.

* * * * *